(12) United States Patent
Burkus et al.

(10) Patent No.: US 6,743,234 B2
(45) Date of Patent: Jun. 1, 2004

(54) METHODS AND INSTRUMENTATION FOR VERTEBRAL INTERBODY FUSION

(75) Inventors: J. Kenneth Burkus, Columbus, GA (US); Eddie F. Ray, III, Collierville, TN (US); James P. Duncan, Southaven, MS (US)

(73) Assignee: SDGI Holdings, Inc., Wilmington, DE (US)

( * ) Notice: Subject to any disclaimer, the term of this patent is extended or adjusted under 35 U.S.C. 154(b) by 144 days.

(21) Appl. No.: 09/965,018

(22) Filed: Sep. 27, 2001

(65) Prior Publication Data

US 2002/0068936 A1 Jun. 6, 2002

Related U.S. Application Data

(63) Continuation-in-part of application No. 09/756,492, filed on Jan. 8, 2001, now Pat. No. 6,648,895, which is a continuation-in-part of application No. 09/498,426, filed on Feb. 4, 2000, now Pat. No. 6,575,981.
(60) Provisional application No. 60/118,793, filed on Feb. 4, 1999.

(51) Int. Cl.[7] ............................................... A61B 17/58
(52) U.S. Cl. ........................................................ 606/90
(58) Field of Search .......................... 606/90, 105, 86; 623/17.11, 17.12, 17.13, 17.14, 17.15, 17.16

(56) References Cited

U.S. PATENT DOCUMENTS

| | | | |
|---|---|---|---|
| 5,015,255 A | 5/1991 | Kuslich | |
| 5,055,104 A | 10/1991 | Ray | |
| 5,431,658 A | 7/1995 | Moskovich | |

(List continued on next page.)

FOREIGN PATENT DOCUMENTS

| | | |
|---|---|---|
| EP | 0 732 093 A2 | 2/1996 |
| EP | 0 880 938 A1 | 12/1998 |
| WO | WO 93/14801 | 8/1993 |
| WO | WO 96/27345 | 9/1996 |
| WO | WO 96/40020 | 12/1996 |

(List continued on next page.)

OTHER PUBLICATIONS

*Surgical Technique Using Bone Dowel Instrumentation for Anterior Approach*, Sofamor Danek The Spine Specialist, 1996.
*Reduced Profile Instrumentation Surgical Technique*, as described by J. Kenneth Burkus and John D. Dorchak, M.D.; Sofamor Danek, ©1999.
*Anterior Instrumentation Surgical Technique*, as described by Scott H. Kitchel, M.D.; Sofamor Danek, ©1999.
*Lumbar Tapered Fusion Device Surgical Technique*, as described by Thomas A. Zdeblick and J. Kenneth Burkus, Sofamor Danek, ©2000.

*Primary Examiner*—Eduardo C. Robert
(74) *Attorney, Agent, or Firm*—Woodard, Emhardt, Moriarty, McNett & Henry LLP

(57) ABSTRACT

Methods and instrumentation particularly adapted for disc space preparation for insertion of implants from an anterior approach to the spine are provided. The instruments include a guide sleeve defining a channel having overlapping cylindrical working channel portions and lateral non-distracting extensions extending from reduced thickness wall portions. The guide sleeve has an overall reduced width configuration. A pair of distractors are provided. A first distractor includes a shaft and distal tip, and the second distractor includes a shaft and distal tip. The first and second distractors can be used with the guide sleeve. Methods using the disclosed instruments are also provided.

19 Claims, 41 Drawing Sheets

U.S. PATENT DOCUMENTS

| | | |
|---|---|---|
| 5,484,437 A | 1/1996 | Michelson |
| 5,489,307 A | 2/1996 | Kuslich et al. |
| 5,505,732 A | 4/1996 | Michelson |
| 5,514,180 A | 5/1996 | Heggeness et al. |
| 5,556,399 A | 9/1996 | Huebner |
| 5,569,205 A | 10/1996 | Hart et al. |
| 5,571,109 A | 11/1996 | Bertagnoli |
| 5,609,636 A | 3/1997 | Kohrs et al. |
| 5,720,748 A | 2/1998 | Kuslich et al. |
| 5,741,253 A | 4/1998 | Michelson |
| 5,759,185 A | 6/1998 | Grinberg |
| 5,766,252 A | 6/1998 | Henry et al. |
| 5,772,661 A | 6/1998 | Michelson |
| 5,785,710 A | 7/1998 | Michelson |
| 5,797,909 A | 8/1998 | Michelson |
| 5,865,834 A | 2/1999 | McGuire |
| 5,865,847 A | 2/1999 | Kohrs et al. |
| 5,885,299 A | 3/1999 | Winslow et al. |
| 5,899,908 A | 5/1999 | Kuslich et al. |
| 5,947,971 A | 9/1999 | Kuslich et al. |
| 5,968,098 A | 10/1999 | Winslow |
| 6,004,326 A | 12/1999 | Castro et al. |
| 6,033,405 A | 3/2000 | Winslow et al. |
| 6,042,582 A | 3/2000 | Ray |
| 6,056,749 A | 5/2000 | Kuslich |
| 6,059,790 A | 5/2000 | Sand et al. |
| 6,063,088 A | 5/2000 | Winslow |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,113,602 A | 9/2000 | Sand |
| 6,120,506 A | 9/2000 | Kohrs et al. |
| 6,123,705 A | 9/2000 | Michelson |
| 6,156,040 A | 12/2000 | Yonemura et al. |
| 6,159,214 A | 12/2000 | Michelson |
| 6,171,339 B1 | 1/2001 | Houfburg et al. |
| 6,174,311 B1 | 1/2001 | Branch et al. |
| 6,210,412 B1 | 4/2001 | Michelson |
| 6,224,595 B1 | 5/2001 | Michelson |
| 6,224,599 B1 | 5/2001 | Baynham et al. |
| 6,224,607 B1 | 5/2001 | Michelson |
| 6,277,122 B1 | 8/2001 | McGahan et al. |
| 6,447,512 B1 | 9/2002 | Landry et al. |
| 6,575,981 B1 * | 6/2003 | Boyd et al. ............... 606/90 |
| 6,582,437 B2 * | 6/2003 | Dorchak et al. ............ 606/90 |
| 6,648,895 B2 * | 11/2003 | Burkus et al. ............ 606/90 |
| 2001/0016741 A1 | 8/2001 | Burkus et al. |

FOREIGN PATENT DOCUMENTS

| | | |
|---|---|---|
| WO | WO 99/09896 | 3/1999 |
| WO | WO 99/09913 | 3/1999 |
| WO | WO 99/52453 | 10/1999 |
| WO | WO 99/59481 | 11/1999 |
| WO | WO 00/041654 | 7/2000 |
| WO | WO 00/041655 | 7/2000 |
| WO | WO 00/45709 | 8/2000 |

* cited by examiner

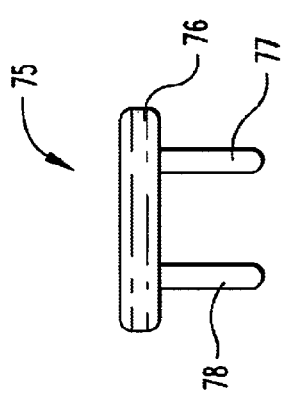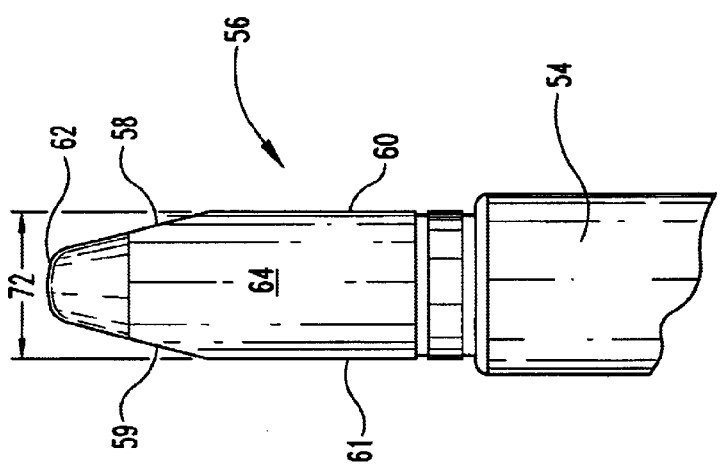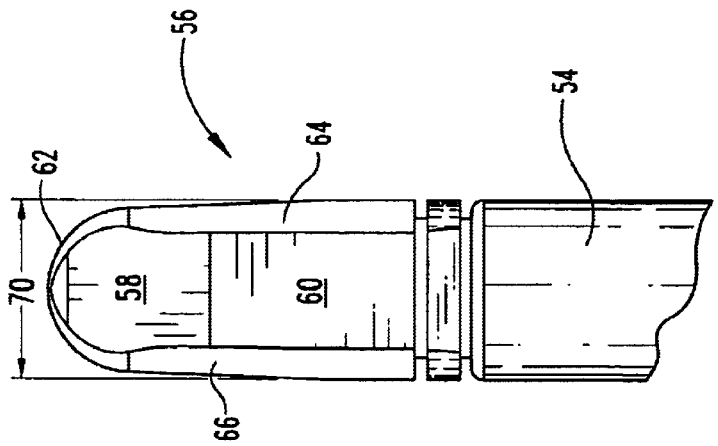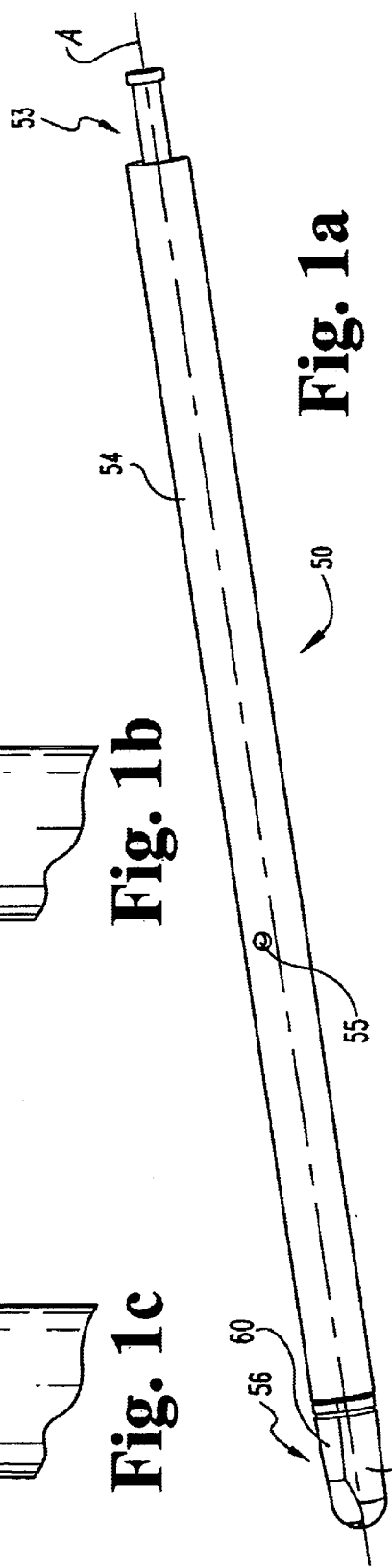

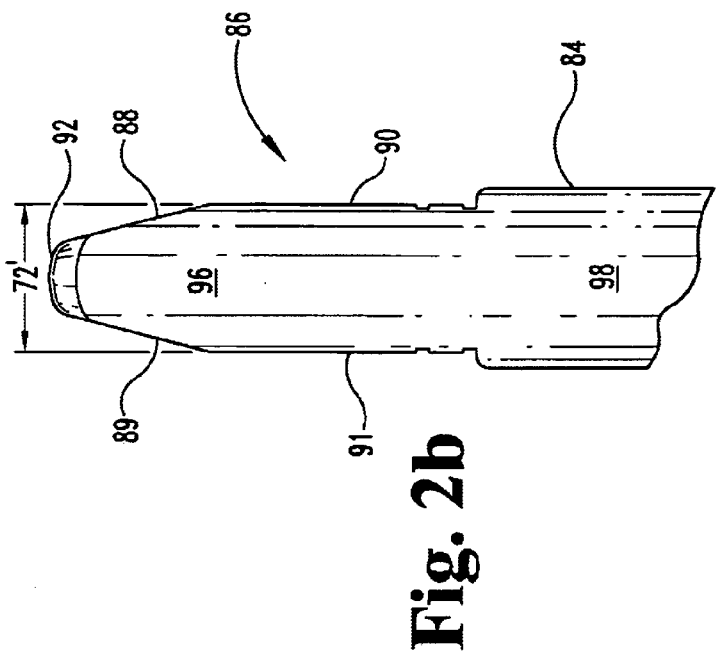
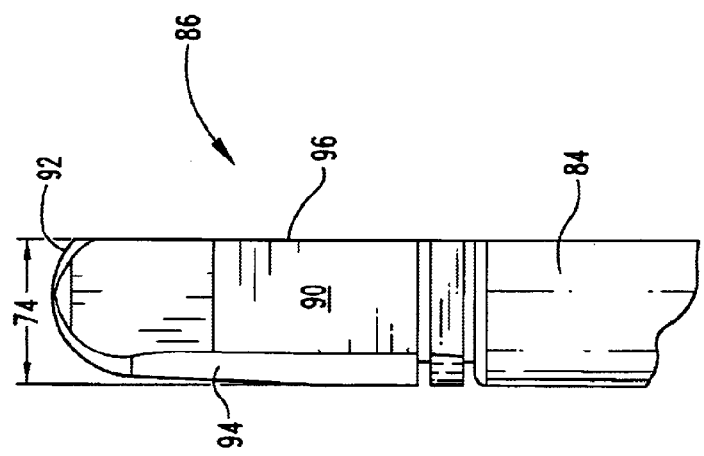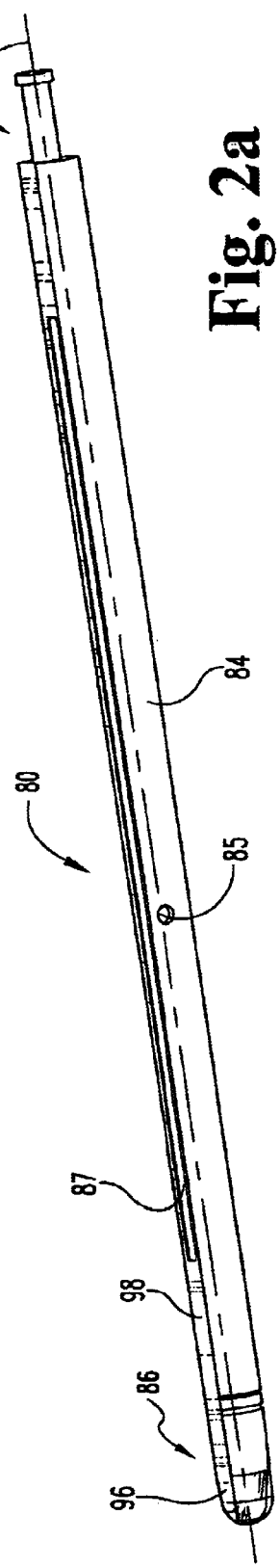

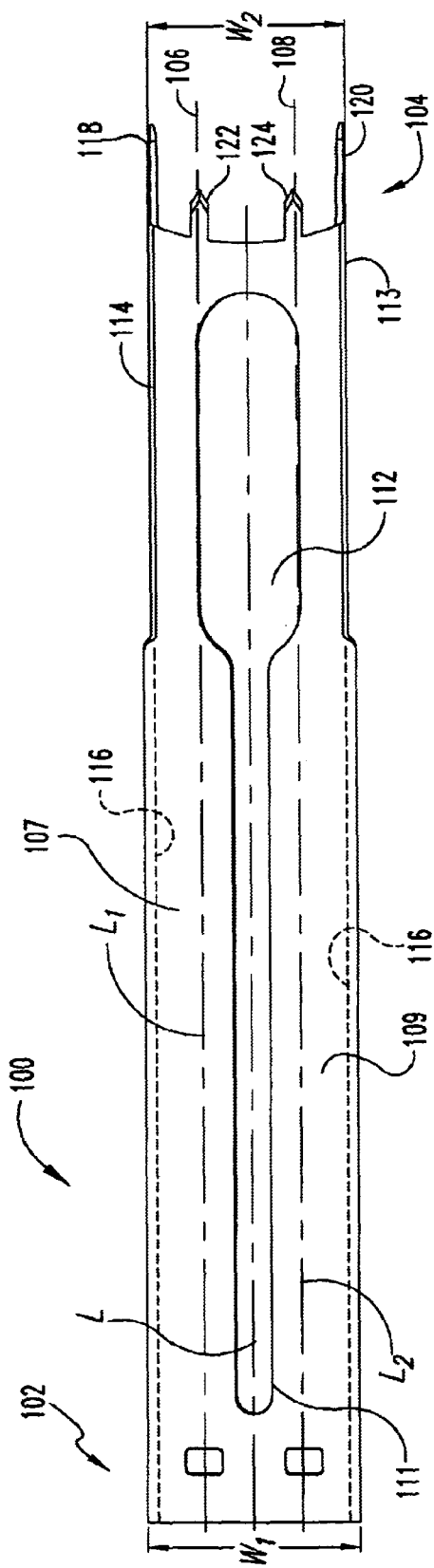
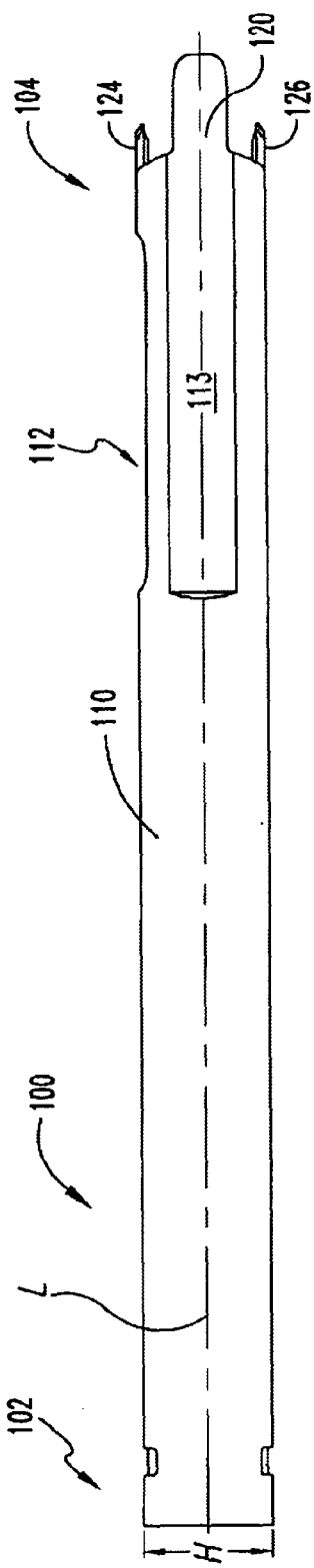
Fig. 4
Fig. 5

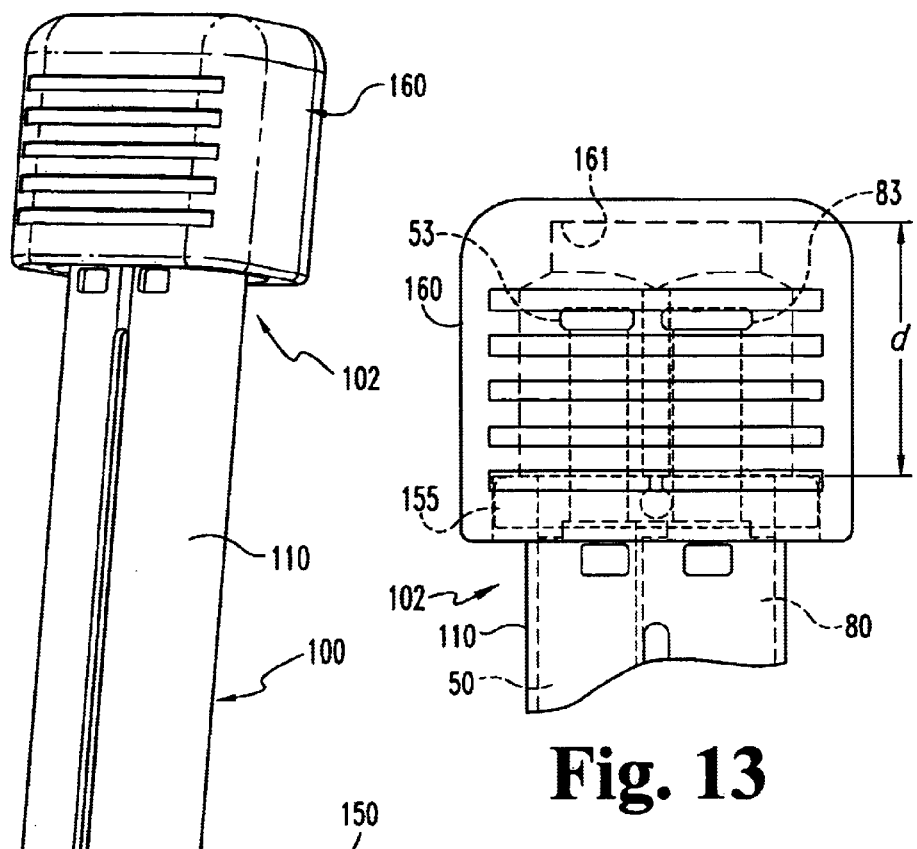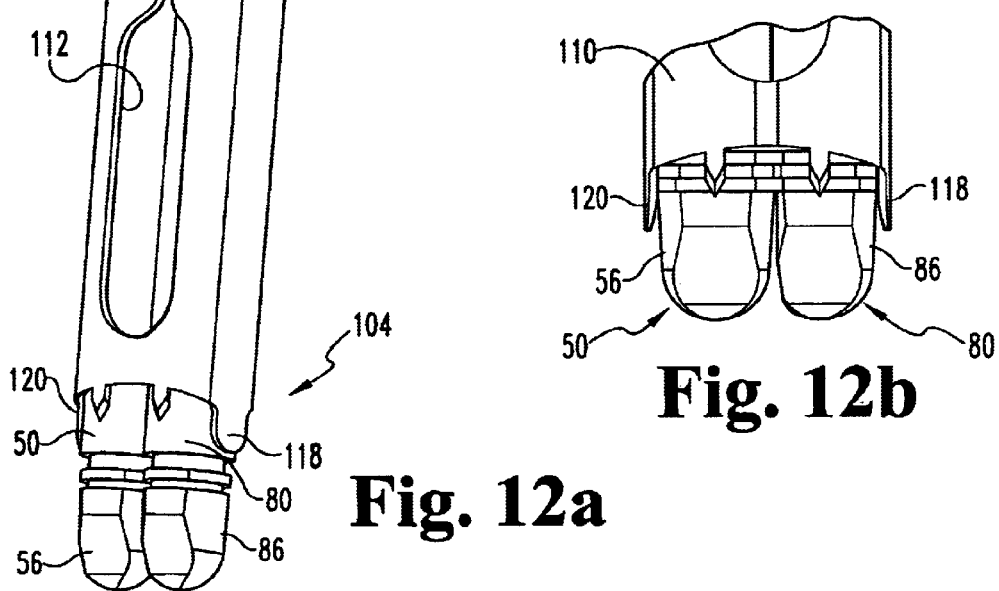
Fig. 13
Fig. 12b
Fig. 12a

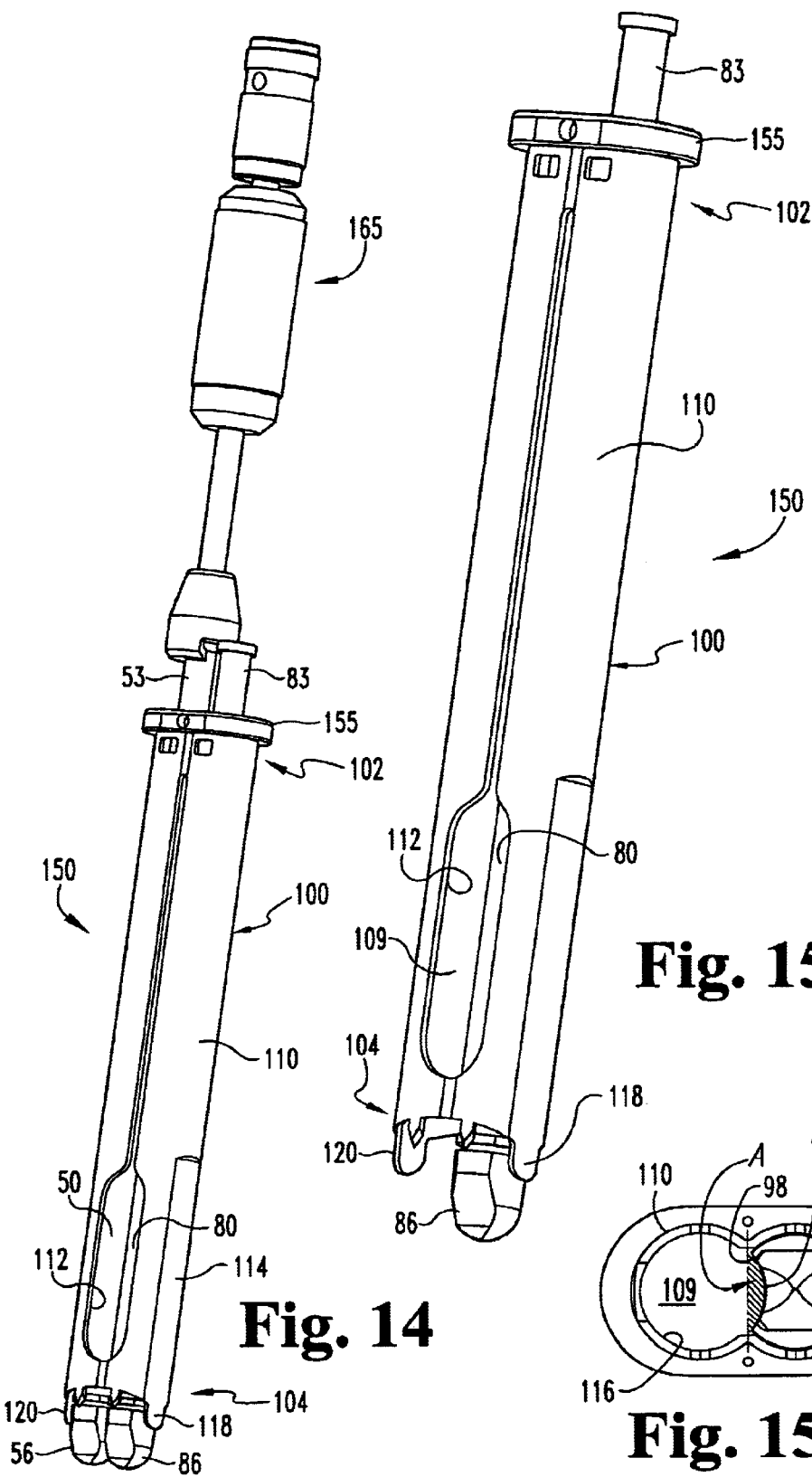
Fig. 14
Fig. 15a
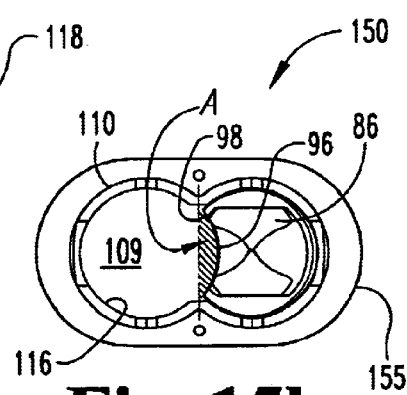
Fig. 15b

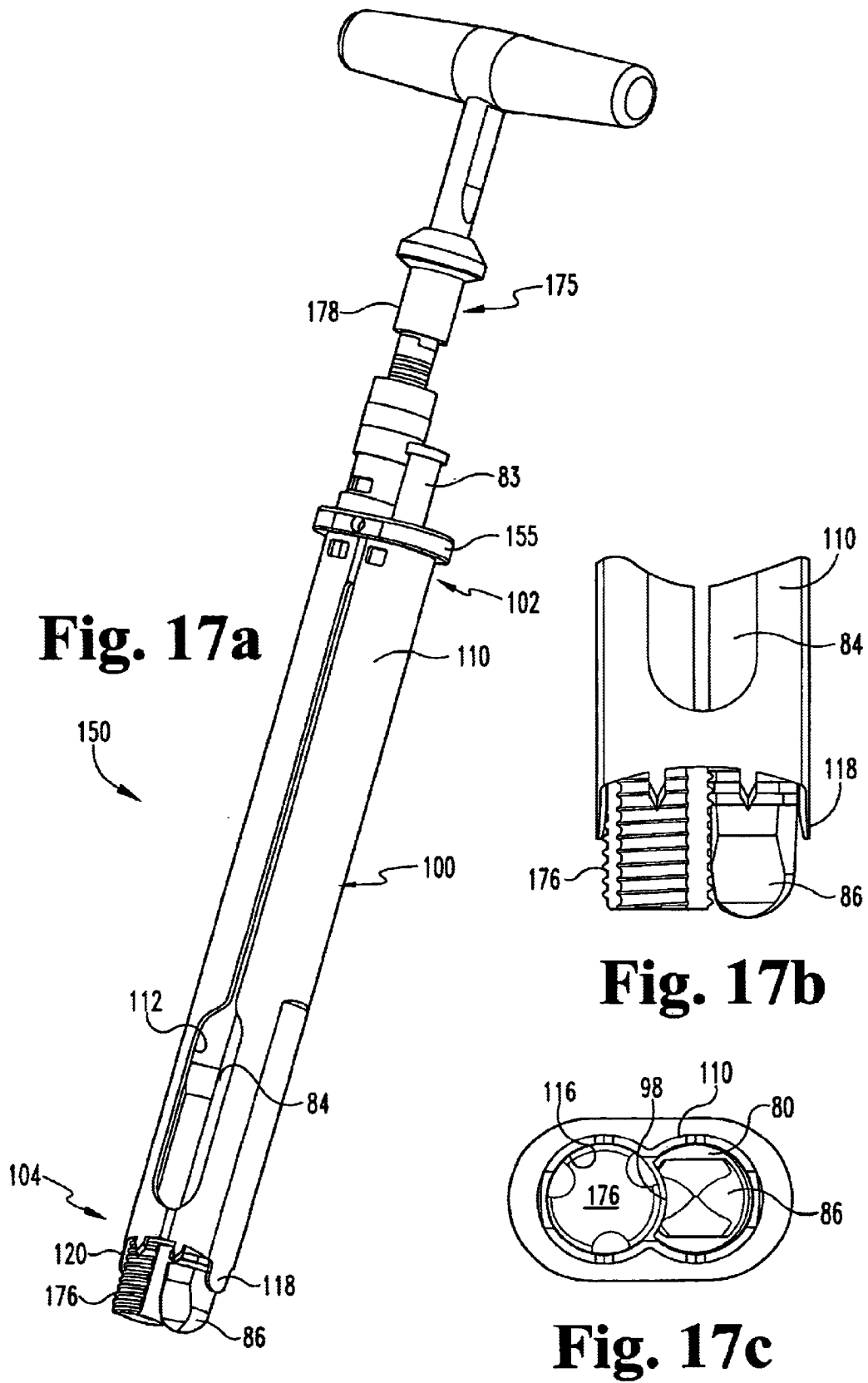
Fig. 17a
Fig. 17b
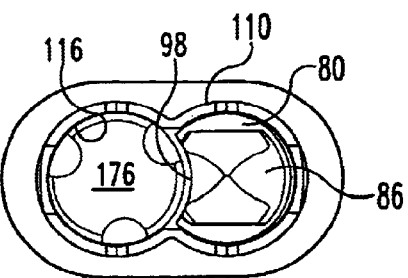
Fig. 17c

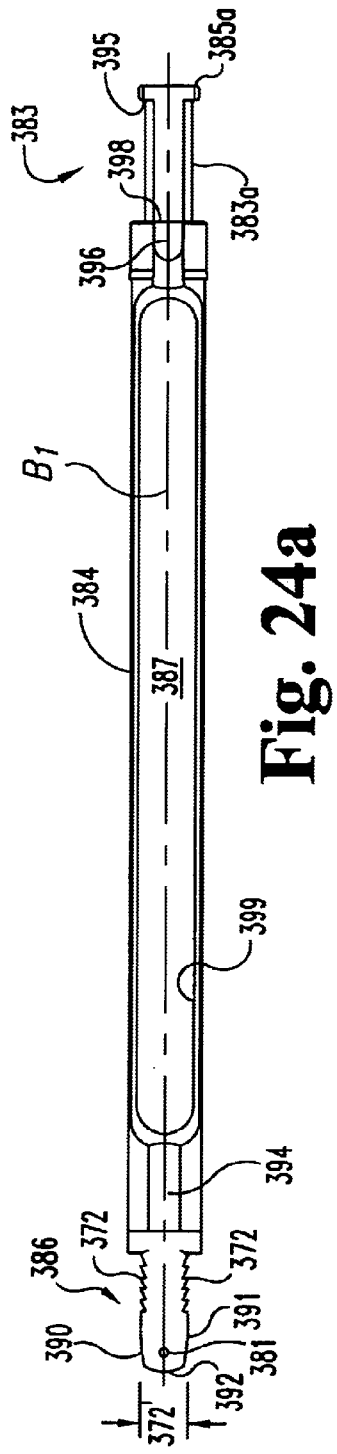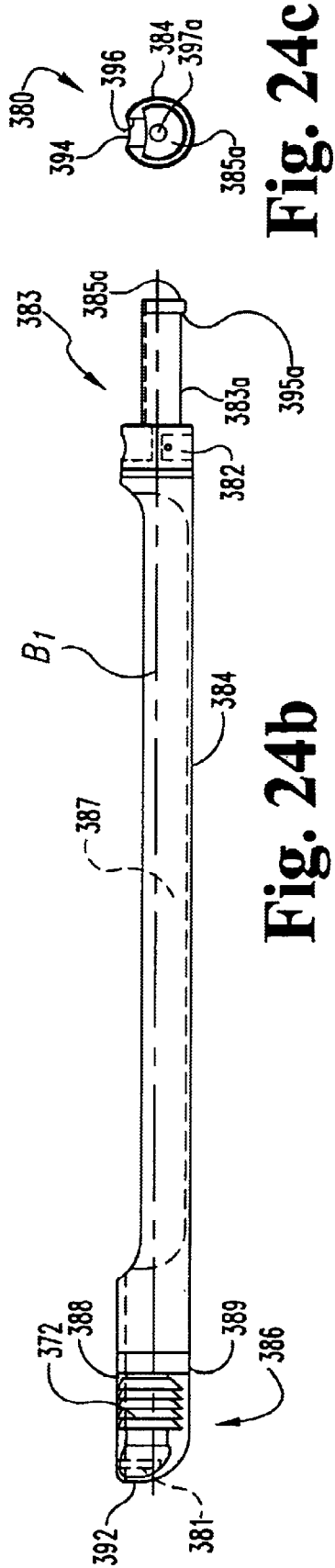

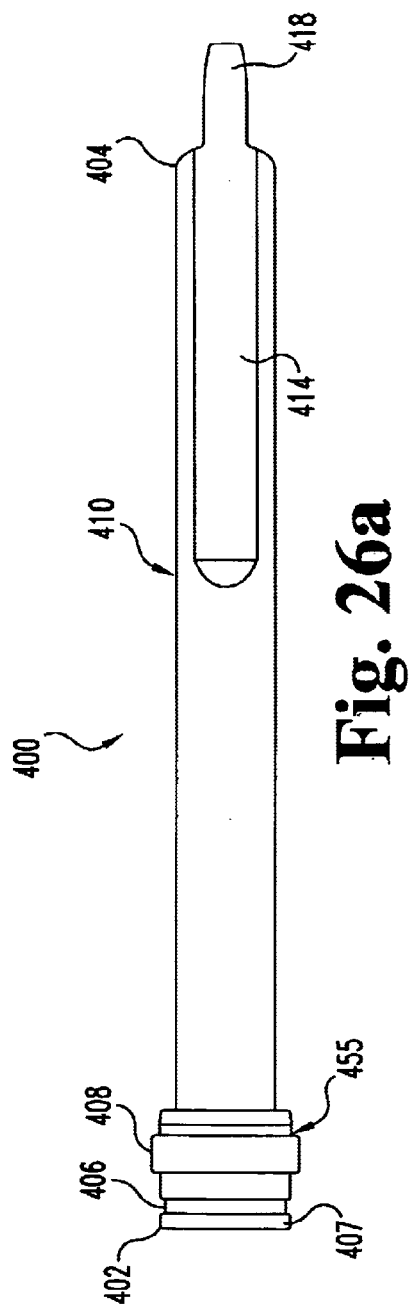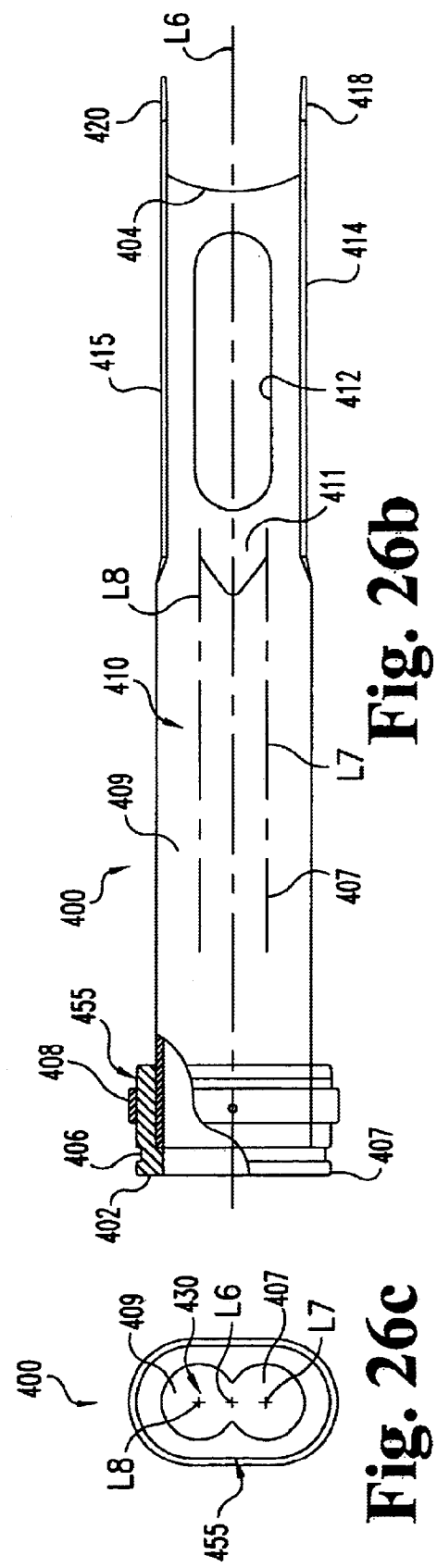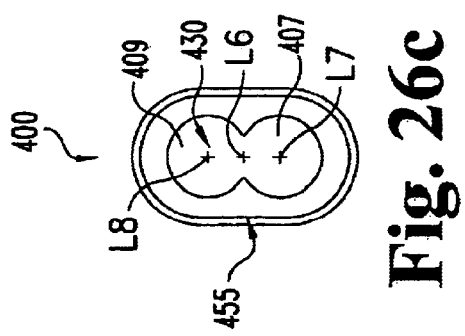

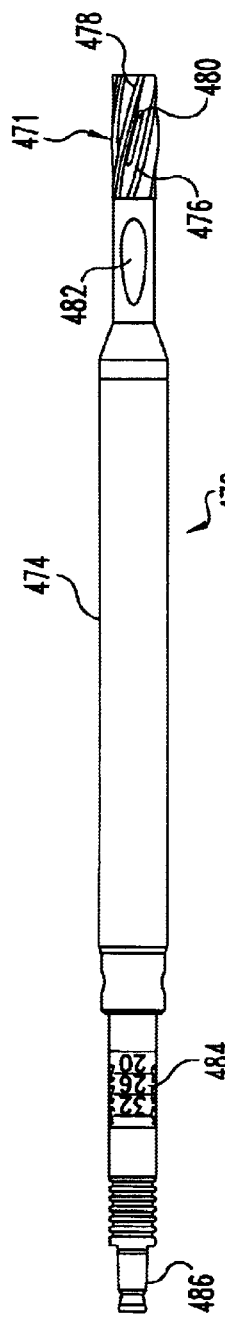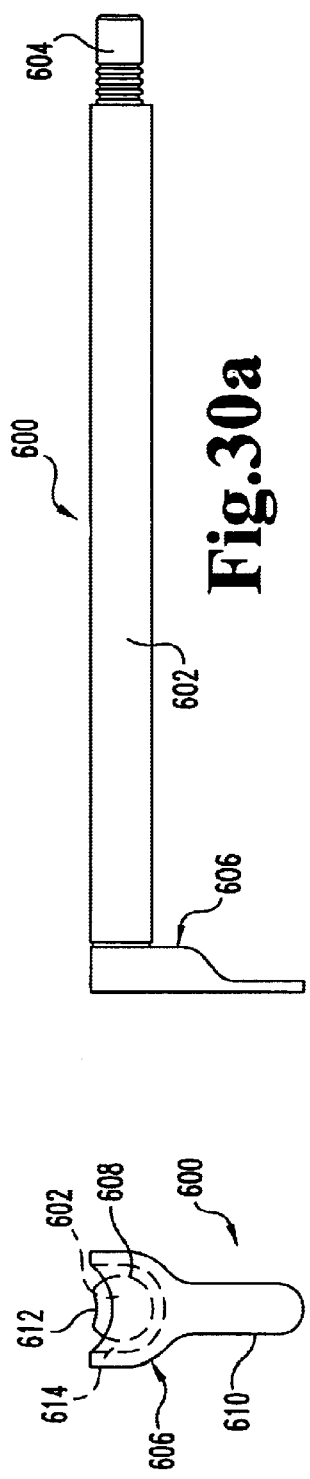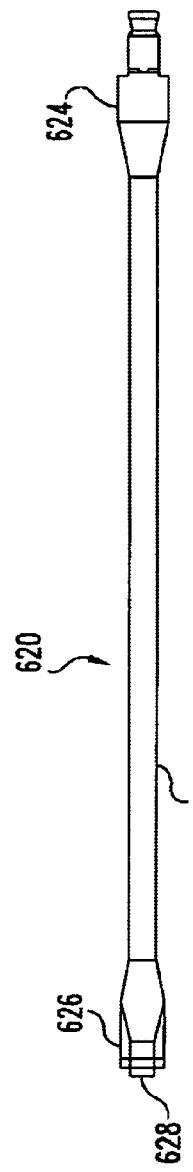

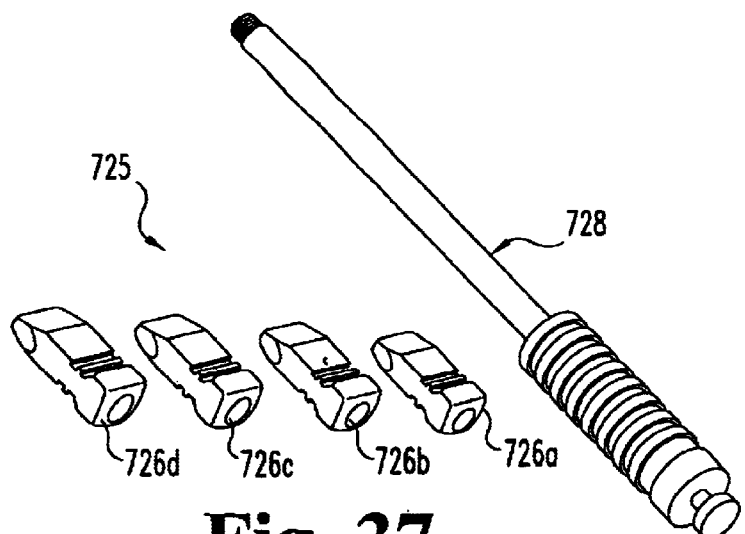
Fig. 37
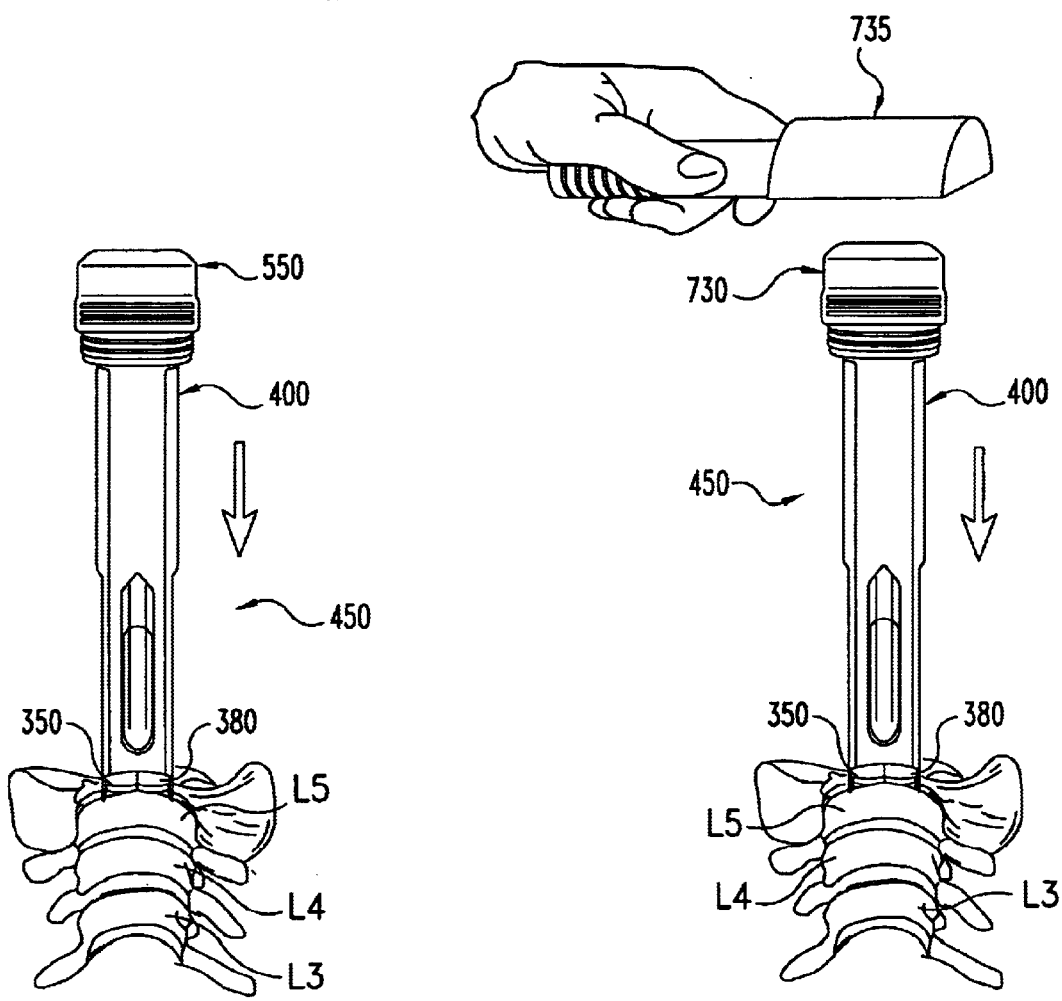
Fig. 38
Fig. 39

METHODS AND INSTRUMENTATION FOR VERTEBRAL INTERBODY FUSION

CROSS-REFERENCES TO RELATED APPLICATIONS

The present application is a continuation-in-part of U.S. patent application Ser. No. 09/756,492 filed Jan. 8, 2001, and now issued as U.S. Pat. No. 6,648,895, which is a continuation-in-part of U.S. patent application Ser. No. 09/498,426, filed Feb. 4, 2000, and now issued as U.S. Pat. No. 6,575,981; which claims the benefit of the filing date of Provisional application Serial No. 60/118,793, filed Feb. 4, 1999.

BACKGROUND OF THE INVENTION

The present invention relates generally to surgical procedures for spinal stabilization and more specifically to instrumentation adapted for inserting a spinal implant within the intervertebral disc space between adjacent vertebra. More particularly, while aspects of the invention may have other applications, the present invention is especially suited for disc space preparation and implant insertion into a disc space from an anterior surgical approach to the spine.

Various surgical methods have been devised for the implantation of fusion devices into the disc space. Both anterior and posterior surgical approaches have been used for interbody fusions. In 1956, Ralph Cloward developed a method and instrumentation for anterior spinal interbody fusion of the cervical spine. Cloward surgically removed the disc material and placed a tubular drill guide with a large foot plate and prongs over an alignment rod and then embedded the prongs into adjacent vertebrae. The drill guide served to maintain the alignment of the vertebrae and facilitated the reaming out of bone material adjacent the disc space. The reaming process created a bore to accommodate a bone dowel implant. The drill guide was thereafter removed following the reaming process to allow for the passage of the bone dowel which had an outer diameter significantly larger than the reamed bore and the inner diameter of the drill guide. The removal of the drill guide left the dowel insertion phase completely unprotected.

More recent techniques have advanced this concept and have provided further protection for sensitive tissue during disc space preparation and dowel insertion. Such techniques have been applied to an anterior approach to the lumbar spine.

An initial opening or openings are made in the disc space and the height of the disc space is distracted to approximate normal height. Typically, a first distractor is inserted with a height estimated by radiological examination. If additional distraction is required, the first distractor is removed and a second, larger distractor is inserted. However, since the positioning of the distractors is performed without the benefit of protective guide sleeves, the switching of distractors increases the potential for damage to neurovascular structures and may correspondingly increase the time of the procedure.

For bilateral procedures, a double barrel sleeve may be inserted over the distractors, with a central extension extending into the disc space to maintain distraction. One limitation on guide sleeve placement is the amount of neurovascular retraction that must be achieved to place the guide sleeves against the disc space. For some patients, a double barrel sleeve may not be used because there is insufficient space adjacent the disc space to accept the sleeve assembly. Thus, there remains a need for guide sleeves requiring less neurovascular retraction for proper placement and providing greater protection to adjacent tissue.

While the above-described techniques are advances, improvement is still needed to reduce the procedure time by utilization of improved instruments and techniques, to reduce the potential for damage to sensitive tissue adjacent the disc space, and to limit the amount of vessel retraction necessary to utilize the protective instrumentation. The present invention is directed to this need and provides more effective methods and instrumentation for achieving the same.

SUMMARY OF THE INVENTION

The present invention relates to methods and instrumentation for vertebral interbody fusion. The instruments include distractors having tips inserted into the disc space that conform to the anatomical configuration of the disc space. Such distractors are self-centering in the disc space both laterally and in the cephalad/caudal directions, and better maintain their position after insertion. Thus, subsequent procedures performed in the disc space based upon positioning of the distractors are more symmetrical about the spinal column axis and also more uniform between the adjacent vertebral endplates.

In another aspect of the invention, a surgical instrument assembly for distracting a spinal disc space is provided. The assembly includes a first distractor that has a first shaft extending between a proximal end and a distal end and a first distractor tip defining a distraction height that extends from the distal end of the first shaft. The assembly further includes a second distractor having a second shaft extending between a proximal end and a distal end and a second distractor tip extending defining a distraction height. Each of the first and second distractor tips are self-centering in the disc space both laterally and in the cephalad/caudal directions, and better maintain their position after insertion. In one embodiment, there is provided a guide sleeve having a working channel extending between a proximal end and a distal end the sleeve. The first and second distractors are received in the working channel of the guide sleeve.

Related objects, advantages, aspects, forms, and features of the present invention will be apparent from the following description.

BRIEF DESCRIPTION OF THE DRAWINGS

FIG. 1a is a perspective view of a distractor according to the present invention.

FIG. 1b is an enlarged front view of the tip of the distractor of FIG. 1a.

FIG. 1c is an enlarged side view of the tip of the distractor of FIG. 1a.

FIG. 2a is a perspective view of a distractor according to another aspect of the present invention.

FIG. 2b is an enlarged front view of the tip of the distractor of FIG. 2a.

FIG. 2c is an enlarged side view of the tip of the distractor of FIG. 2a.

FIG. 2d is an elevation view of a distractor clip.

FIG. 4 is a front view of the guide sleeve of FIG. 3.

FIG. 5 is a side view of the guide sleeve of FIG. 3.

FIGS. 12a–12b are perspective views of the guide sleeve assembly 150 with an impactor cap disposed thereon prior to seating the guide sleeve.

FIGS. 13 is a perspective view of the guide sleeve assembly with an impactor cap disposed thereon.

FIG. 14 is a perspective view of the guide sleeve assembly with a slap hammer disposed on one of the distractors.

FIGS. 15a–15b are a perspective view and an end view, respectively, of the guide sleeve assembly with a distractor removed.

FIGS. 17a–17c are a perspective view, detail view and end view, respectively, of the guide sleeve assembly with a tap disposed adjacent a distractor.

FIG. 24a is an elevational view of another embodiment second distractor according to the present invention.

FIG. 24b is an elevational view of the distractor of FIG. 24a rotated 90 degrees about its longitudinal axis.

FIG. 24c is a right end view of the distractor of FIG. 24b.

FIG. 26a is an elevational view another embodiment guide sleeve according to the present invention.

FIG. 26b is an elevational view in partial section of the guide sleeve of FIG. 26a rotated 90 degrees about its longitudinal axis.

FIG. 26c is a left end view of the guide sleeve of FIG. 26b.

FIG. 27c is a cross-sectional view taken through line 27c–27c of FIG. 27a.

FIG. 27d is a left end elevational view of the distractor driver cap of FIG. 27a.

FIG. 29 is an elevational view of a reamer having application in the present invention.

FIG. 30a is an elevational view of reamer plug according to another aspect of the present invention.

FIG. 30b is a left end view of the reamer plug of FIG. 30a.

FIG. 31 is an elevational view of an implant adjuster having application in the present invention.

FIG. 33 is an elevational view of an outer sleeve for receiving the implant holder of FIG. 32a.

FIG. 37 is a perspective view of a starter distractor set with various sized distractor tips for use therewith.

FIG. 38 illustrates insertion of a distractor/guide sleeve assembly into the disc space with the distractor driver cap of FIGS. 27a–27d secured thereto.

FIG. 39 illustrates insertion of the guide sleeve into the disc space using an impactor cap.

DESCRIPTION OF THE PREFERRED EMBODIMENTS

Figure 3:
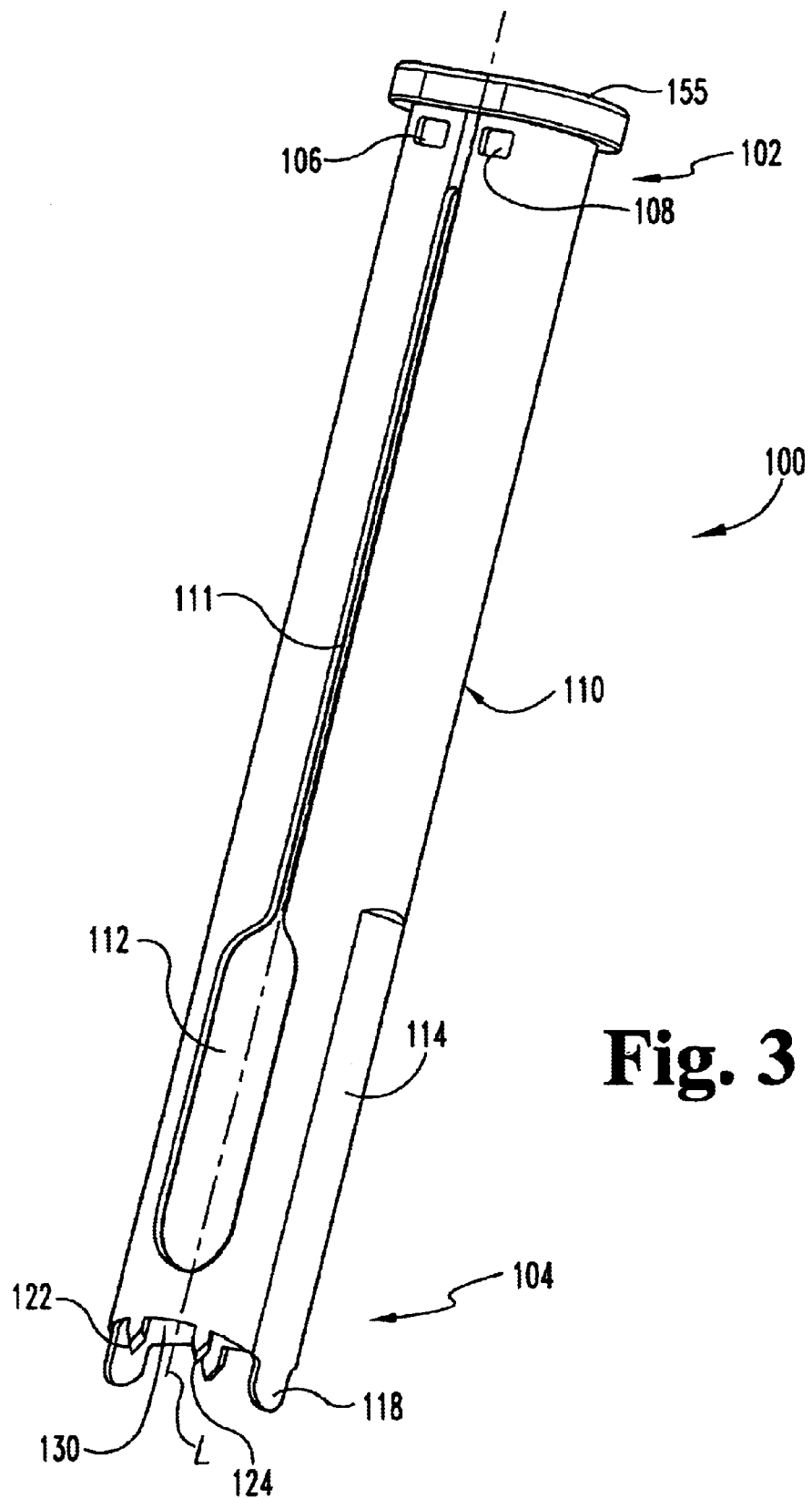
FIG. 3 is a perspective view of a guide sleeve according to another aspect of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to methods and instrumentation for performing vertebral interbody fusion. Specifically, although aspects of the present invention may have other uses either alone or in combination, the instruments and methods disclosed herein are particularly useful for anterior lumbar interbody fusion. However, the surgical instruments and methods according to the present invention are not limited to such an approach, and may find application in, but without limitation, lateral and anterior-lateral approaches to the spine as well. Also, the surgical instruments and methods of the present invention may find application at all vertebral segments of the spine, and in areas other than spinal surgery.

Referring now to FIGS. 1a–c, there is shown a convex or first disc space distractor 50 according to one aspect of the present invention. Distractor 50 includes a proximal end 53 configured for engagement with conventional tools and handles (not shown) used in operative procedures on the spine. A shaft 54 is joined with a distractor tip 56. In the illustrated embodiment, shaft 54 has a hollow interior and a clip hole 55 communicating with the hollow interior; however, the present invention also contemplates a solid shaft 54. Also, while an integral shaft and head are shown, head 56 may be removably attached to shaft 54. One such removable attachment is more fully disclosed in U.S. patent application entitled METHOD AND INSTRUMENTATION FOR VERTEBRAL INTERBODY FUSION, Ser. No. 09/287,917, filed Apr. 7, 1999, which is incorporated herein by reference in its entirety (hereinafter referred to as the '917 patent application.) Distractor tip 56 is designed such that it can be inserted in a disc space to establish a first working distraction height 72 (see FIG. 1b). More specifically, distractor tip 56 has a rounded leading edge 62 that extends to opposing inclined surfaces 58 and 59, which in turn extend more proximally and blend into substantially planar opposing surfaces 60 and 61, respectively. Extending between planar surfaces 60 and 61 and proximal the rounded tip 62 are opposite convex surfaces 64 and 66.

Planar surfaces 60 and 61 extend in a substantially parallel alignment along a longitudinal axis A of distractor 50 and define height 72 therebetween. It should be understood that the inclined surfaces 58 and 59 cooperate to aid insertion of the distractor tip 56 into the disc space and to initially distract the disc space to at least a height 72. If first distraction height 72 is sufficient, further procedures as known in the art may then be carried out to accomplish implant insertion. While a specific distractor has been described in detail, it is contemplated that other known distractor configurations may be substituted for the same without deviating from the scope of this invention.

Referring now to FIGS. 2a–c, there is shown a second disc space distractor 80 according to one aspect of the present invention. Distractor 80 includes a proximal end 83 configured for engagement with conventional tools and handles (not shown). A shaft 84 is joined with a distractor tip 86. In the illustrated embodiment, shaft 84 has a hollow interior and a hole 85 communicating therewith. While an integral shaft and head are shown, head 86 may be removably attached to shaft 84, as similarly described with respect to the removable attachments disclosed in the '917 patent application. Similar to distractor tip 56 of distractor 50, distractor tip 86 is designed such that it can be inserted in a disc space to establish a first working distraction height 72' (see FIG. 2b) that is preferably the substantially the same as working height 72. More specifically, distractor tip 86 has a rounded leading edge 92 that extends to opposing inclined surfaces 88 and 89 which, in turn, extend more proximally and blend into substantially planar opposing surfaces 90 and 91, respectively.

Planar surfaces 90 and 91 extend substantially parallel to longitudinal axis B of distractor 80 to define height 72' therebetween. Extending between planar surfaces 90 and 91 are convex surface 94 and a recessed area defined by opposite concave surface 96. Along the distractor shaft 84, there is defined a concave surface 98 that is adjacent to and coplanar with concave surface 96 of distal tip 86 to define a concave surface extending along the length of distractor 80. In the illustrated embodiment, surface 98 has a slot 87 formed therein communicating with the hollow interior of shaft 84; however, it the present invention also contemplates a solid shaft 84 and a shaft 84 without slot 87. As explained more fully below, concave surfaces 96, 98 are configured to receive convex surface 64 or 66 of distractor 50 to reside therein when distractors 50 and 80 are disposed in side-by-side relation. Concave surfaces 96, 98 also partially define a working space that allows operative procedures to be performed therethrough.

It should be understood that the inclined surfaces 88 and 89 cooperate to aid insertion of distractor tip 86 into the disc space, and to distract the disc space and maintain disc space distraction to at least a height 72, 72'. To further aid in distractor insertion, in FIG. 2d there is shown a distractor clip 75 having a cross member 76 with first clip member 77 and second clip member 78 extending therefrom. Clip members 77 and 78 are each received in a corresponding one of holes 55 and 85 to couple distractor 50 to distractor 80. Clip 75 prevents splaying and maintains the relative positioning of distractors 50, 80 during insertion into the disc space. If first distraction height 72 is sufficient, further procedures as known in the art may then be carried out to accomplish implant insertion. It should be further understood that second distractor 80 has a second width 74 that is less than a first width 70 of first distractor 50.

Specifically, but without limitation, the distractor heads 56, 86 may be formed with heights 72 ranging from 6 mm to 24 mm. Preferably, height 72 of the next sized distractor increases or decreases in 2 mm increments. Other variations and may be provided as long as the working distractor height provided approximates the disc height in a normal spine and accommodates insertion of an implant into the disc space as more fully described below.

Referring now to FIG. 3, there is shown a guide sleeve 100 that is useful with the distractors 50 and 80 described above. Guide sleeve 100 has a wall 110 defining a working channel 130 having a figure eight shaped cross-section (FIG. 9) extending in a substantially unobstructed manner from a proximal end 102 to a distal end 104. Sleeve 100 includes upper windows 106 and 108 formed in wall 110 on at least one side of sleeve 100 for engagement by a removal tool to remove sleeve 100. The sleeve 100 also includes lower elongated visualization window 112 centered about the longitudinal axis L with an elongated slot 111 extending proximally window 112. Window 112 provides the surgeon with the ability to visualize the instruments inserted in guide sleeve 100 as well as the openings in the disc space and vertebral bodies, without entirely removing instrumentation from guide sleeve 100. The reduce width of sleeve 100 allows the use of one window 112 for visualization of implant insertion into its respective bilateral location in the disc space, and separate windows along each insertion path are not necessary. However, it should be understood that any number of visualization windows and configurations thereof are contemplated herein, such as those described in the '917 patent application. The present invention also contemplates that covers may be used for visualization windows, as described in greater detail in the '917 patent application.

At proximal end 102 is provided a flange ring 155. Flange ring 155 strengthens sleeve 100 and provides a load transfer member to facilitate transfer of a driving force to sleeve 100, as described more fully below. Adjacent distal end 104, the material thickness along the exterior outer edge of wall 110 is reduced in order to provide a reduced thickness wall portion 114 and an opposite reduced thickness wall portion (not shown). The reduced thickness wall portions define a smaller cross-sectional area for the sleeve 100 as well as a reduced width extending transverse to the longitudinal axis L. The reduced cross-sectional area and smaller width of guide sleeve 100 reduces the amount of vasculature and neural tissue retraction adjacent the disc space that would otherwise be required to place a similarly sized guide sleeve without the width reduction.

Figure 7:
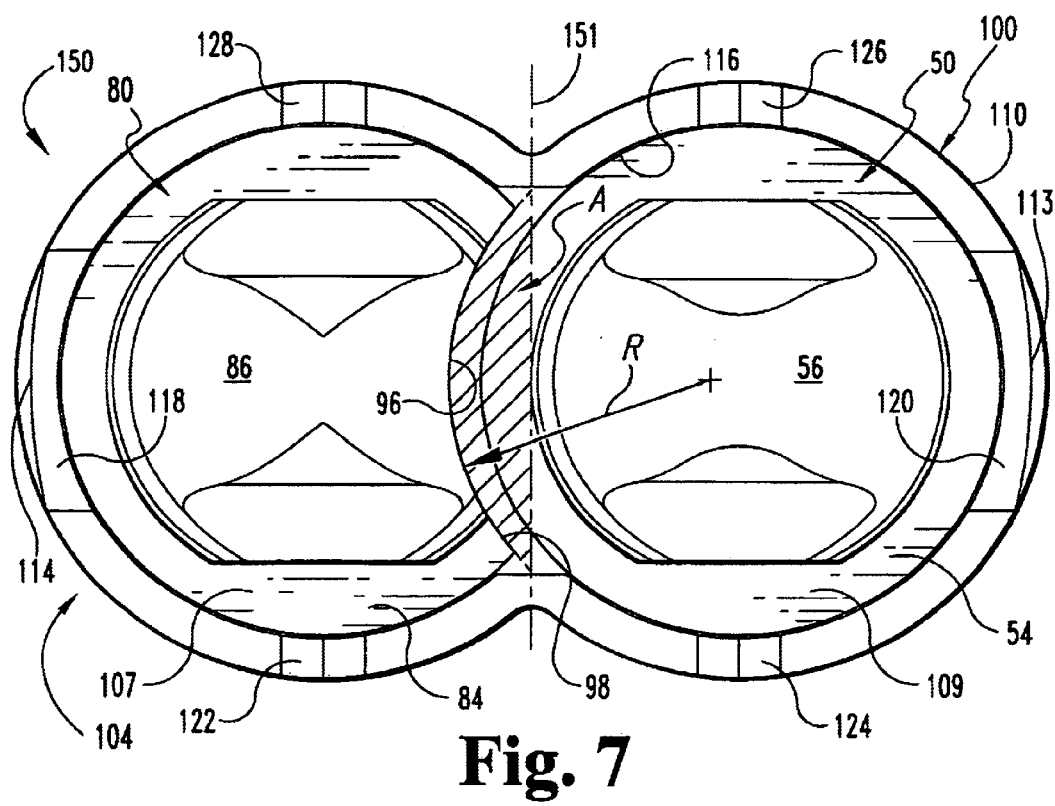
FIG. 7 is an enlarged end view of the distal end of the guide sleeve assembly of FIG. 6.

Distal end 104 includes a pair of flanges 118 and 120 extending from wall 110 on opposite sides of working channel 130. Flanges 118 and 120 are configured to extend partially into the disc space. Flanges 118, 120 are each formed by and are an extension of the corresponding reduced thickness wall portions 114 described above. In a preferred embodiment, flanges 118 and 120 do not provide distraction of the disc space but are primarily provided to protect surrounding vessels and neurological structures from damage during the procedures. Since the lateral flanges do not provide structural support for distraction, the material thickness of the flanges and adjacent side walls may be reduced. Additionally, distal end 104 includes spikes 122, 124, positioned between flanges 118, 120 and a third spike 126 and a fourth spike 128 positioned opposite spikes 122, 124 between flanges 118, 120 as shown in FIG. 7. These spikes may be urged into the bone of the adjacent vertebral bodies to hold guide sleeve 100 in a fixed position relative to the vertebral bodies.

Referring to FIGS. 4 and 5, guide sleeve 100 is shown in front and side views, respectively, to further illustrate an additional aspect of the invention. A proximal end 102 the guide sleeve 100 has a maximum width W1. At distal end 104 of sleeve 100, wall 110 has a reduced wall thickness at side walls 114 and 113 defining a width W2 that is less than width W1. The side walls 113, 114 are preferably not entirely flat and have a slight curvature. Side walls 113, 114 provide a reduction in wall thickness of wall 110 and taper to the full wall thickness of wall 110 at the termination of side walls 113 and 114. The reduction in width of wall 110 decreases the amount of vasculature and neural tissue retraction in the area adjacent the disc space. The desirable reduction in width is accomplished with little reduction in the required strength of the device since distractors 50, 80 are used to distract and maintain the distraction of the vertebral bodies instead of the extensions or side flanges 118, 120 of guide sleeve 100.

Figure 9:
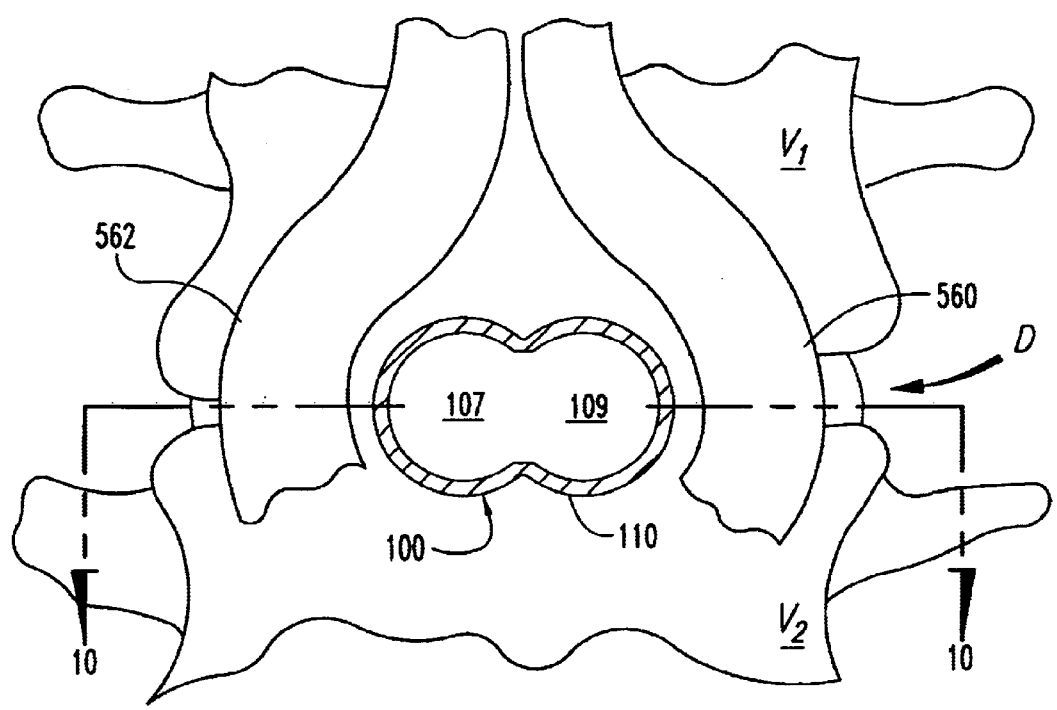
FIG. 9 is an anterior to posterior view of a guide sleeve assembly according to FIG. 3, the guide sleeve assembly is positioned in relation to a pair of adjacent vertebral bodies and blood vessels.

There are also shown in FIGS. 4 and 9 a first working channel portion 107, defined about axis L1, and a second working channel portion 109, defined about axis L2. These working channel portions 107, 109 are positioned on either side of longitudinal axis L of sleeve 100. There is no wall or other structure separating working channel portions 107 and 109. Working channel portion 107 is that portion of working channel 130 about axis L1 between longitudinal axis L and inside surface of 116 of guide sleeve 100. Similarly, working channel portion 109 is that portion of working channel 130 about axis L2 between longitudinal axis L and inside surface 116. Thus, working channel portions 107 and 109 are substantially equal in area, and each has a truncated circular shape, with the truncated portions of each working channel 107 and 109 positioned adjacent one another.

Figure 6:
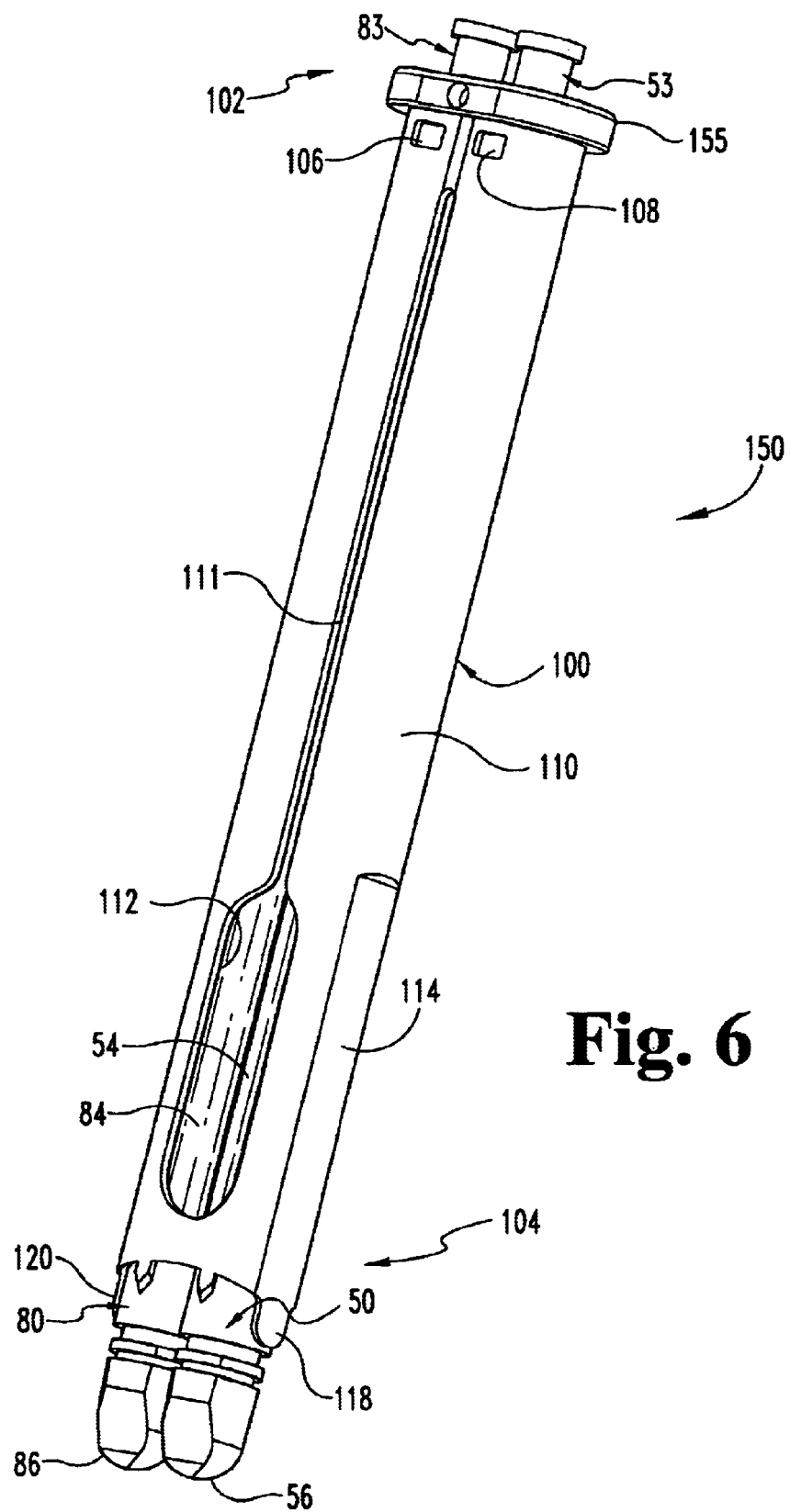
FIG. 6 is a perspective view of a guide sleeve assembly according to another aspect of the present invention.

Referring now to FIG. 6, there is illustrated a distractor/guide sleeve assembly 150 that includes distractors 50 and 80 disposed within working channel 130 of guide sleeve 100 in side-by-side relation. Distractors 50, 80 reside within sleeve 100 with each distractor substantially occupying all or a portion of a corresponding one of working channel portions 107 and 109 of working channel 130. Each distractor 50, 80 extends from proximal end 102 to distal end 104 of the guide sleeve 100. Flange ring 155 is in the form of a flange extending about the proximal end 102 of guide sleeve 100 and contacts a driving cap positioned on distractors 50, 80 in order to maintain the relative positioning between sleeve 100 and distractors 50, 80 during insertion of assembly 150.

Referring now to FIG. 7, there is illustrated an end view at distal end 104 of the assembly 150 showing distractors 50 and 80 in side-by-side relation. More particularly, shaft 54 of distractor 50 is received within concave portion 98 of distractor shaft 84. As also illustrated in this view, concave portion 96 of distractor tip 86 is coextensive with concave surface 98 to form a concave surface that extends the length of the distractor 80. The concave surface of distractor 80 has a radius of curvature R that is preferably about one half the diameter of the cage or implant to be inserted into the disc space. For example, an 18 mm diameter implant requires use of a distractor 80 having a radius of curvature R of about 9 mm.

When distractor 50 is removed from guide sleeve 100, there is defined a cylindrical working space through the working channel 130 adjacent and along the recessed areas of distractor 80. The cylindrical working space includes that portion of the working channel 130 between concave surfaces 96, 98 and inside wall 116 of the guide sleeve 100. Thus, the working space occupies substantially all of working channel portion 107, (FIG. 4) and a portion of working channel portion 109. The area of the portion of the working channel portion 109 occupied by the cylindrical working space is indicated in FIG. 7 by the hatched area A, and is hereinafter referred to as the overlap region. This overlap region A allows operative procedures to be performed in the working space adjacent the distractor 80 using conventionally sized tools and implements while providing a guide sleeve 100 of reduced overall width. The amount of width reduction achieved is approximately the maximum width of overlap region A. It should be understood that shaft 84 need not have a recessed area to provide a cylindrical working space in the disc space, but rather can be provided with a reduced diameter or size that maintains access to the overlap region A in the disc space.

Figure 8:
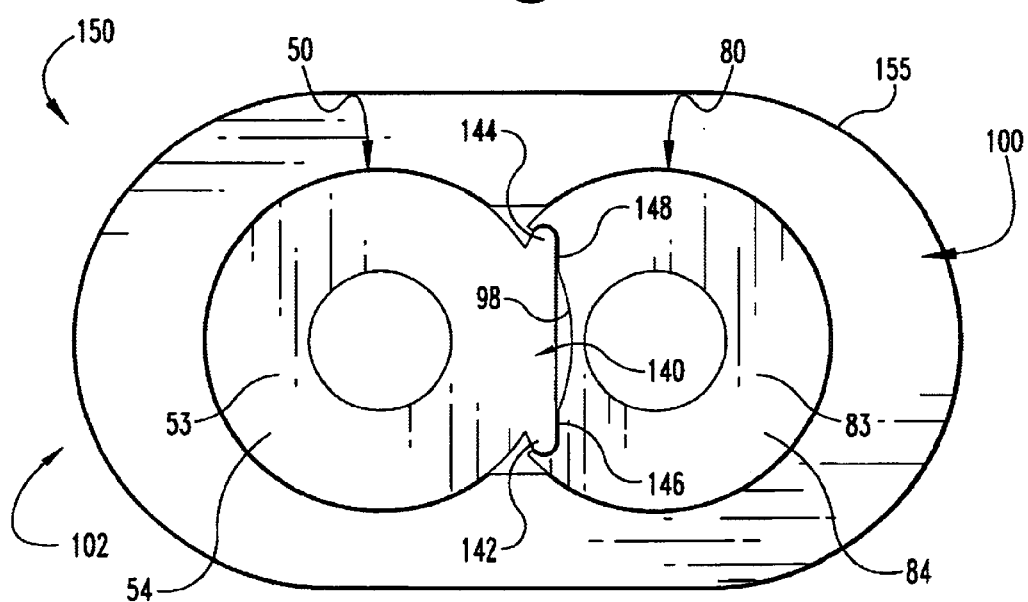
FIG. 8 is an enlarged end view of the proximal end of the guide sleeve assembly of FIG. 6.

In FIG. 8 there is shown a top view of the guide sleeve assembly 150, looking down on proximal ends 53, 83 of the distractors 50, 80 and the proximal end 102 of guide sleeve 100. In one embodiment, there is provided adjacent proximal end 53 of distractor 50 a locking segment 140 formed with and extending from the distractor shaft 54. Locking segment 140 has a first projection 142 and a second projection 144. First and second projections 142, 144 are received within corresponding notches 146, 148 defined in concave surface 98 of shaft 84 of distractor 80 to prevent rotation of distractors 50 and 80 with respect to one another. The present invention also contemplates other mechanisms for engaging distractors 50 and 80 to prevent rotation relative to one another. For example, the above described distractor clip 75 can be used to couple the distractors 50, 80 together. Moreover, it is contemplated that the distractors 50, 80 may be inserted without any locking mechanism.

The present invention contemplates that access to the disc space has heretofore been provided by known surgical techniques and therefore will not be further described herein. The use of intraoperative templates for providing access to the disc space is known in the art. One example of a procedure for gaining access to the disc space is disclosed in the '917 patent application. Another reference including techniques for template positioning and disc space distraction using a starter distractor to initially distract the disc space is the surgical technique brochure entitled *Reduced Profile Instrumentation* published in 1999 by Sofamor Danek, said brochure being incorporated by reference herein in its entirety (hereinafter the Danek brochure.) The present invention also contemplates the use and application of other procedures for gaining access to the disc space in conjunction with the procedures and instruments discussed below as would occur to those skilled in the art. The templates contemplated herein define the area necessary for placement of implants and instruments having a specific configuration and size. While in a preferred embodiment, templates are provided for cylindrical implants having diameters ranging from 16 mm to 24 mm, it is contemplated that other diameters of implant and templates for use therewith may be used and other shapes, such as, but without limitation, squares and rectangles.

Access to an anterior portion of the spinal column is achieved by known methods. Blood vessels, particularly the aorta, vena cava, and branches thereof are mobilized to provide space for bilateral implant placement. The template is inserted into the body and advanced until the pins are disposed adjacent a disc space. The circumference of the template is selected to correspond to the circumference needed for bilateral placement of a pair of implants. More specifically, the area of the template closely approximates the below. In this alternate technique, clip 75 may be used to couple distractors 50, 80 together during insertion. In a further variation, alternating insertion of distractors 50, 80 is not precluded by the present invention. However, insertion of distractors 50, 80 into area needed for placement of the guide sleeve disclosed herein, such as that shown in FIG. 7. It is contemplated that a guide sleeve 100 need not necessarily be used, and tissue to the surgical site is retracted by other means while the disc space is distracted by distractors 50 and 80. The surgical procedures are then performed in the working space defined by the distractors 50, 80 as discussed below without use of a guide sleeve.

Figure 10:
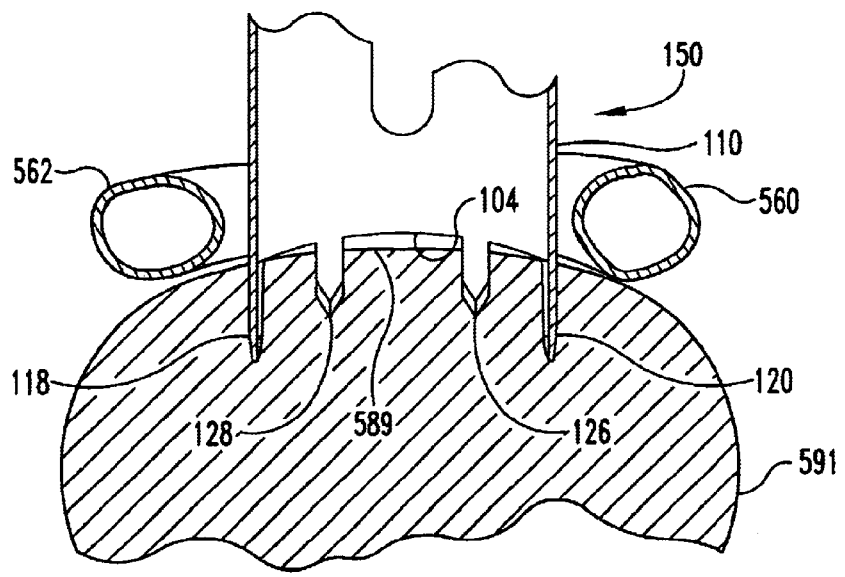
FIG. 10 is a partial cross-sectional view of the disc space through line 10—10 of FIG. 9.

Referring to FIG. 9, a cross section through guide sleeve 100, with distractors 50, 80 removed for clarity, is provided. Sleeve 100 is inserted into a disc space D between two adjacent vertebra V1 and V2. Disposed adjacent guide sleeve 100 are vessels 560 and 562 graphically representing portions of the aorta or vena cava. Referring to FIG. 10, a cross-section through line 10—10 of FIG. 9, sleeve 100, flanges 118, 120 on guide sleeve 100 extend into the disc space where the surgical procedures are being performed. Flanges 118, 120 and sleeve 100 inhibit contact between vessels and tissue surrounding the disc space and the tools used during the surgical procedure. Spikes 122, 124, 126, and 128 may be inserted into the bone of the corresponding vertebral body V1, V2.

Various tools and implements are usable with guide sleeve 100 and distractors 50, 80 disclosed herein and also within the working spaces defined by the working channel 130 of guide sleeve 100. Several of these tools are disclosed in the Danek brochure and in the '917 patent application, while other tools are known to those skilled in the art to which the present invention relates.

Figure 11A:
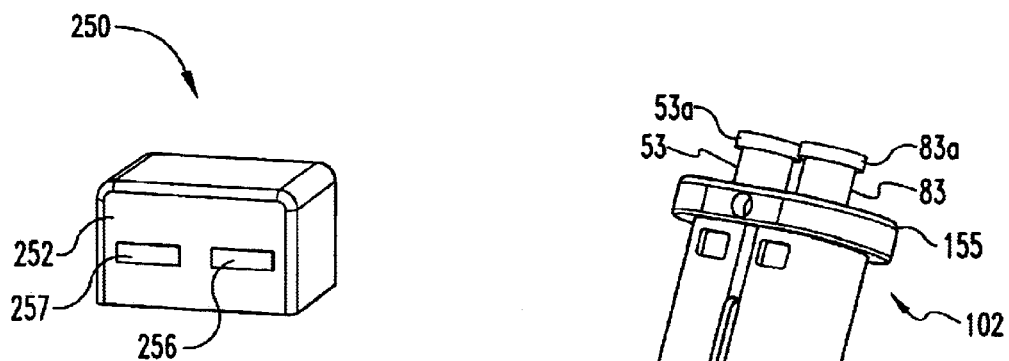
FIGS. 11a and 11b are front and rear elevation views, respectively, of a distractor driver cap for driving the distractors into the disc space.
Figure 11B:
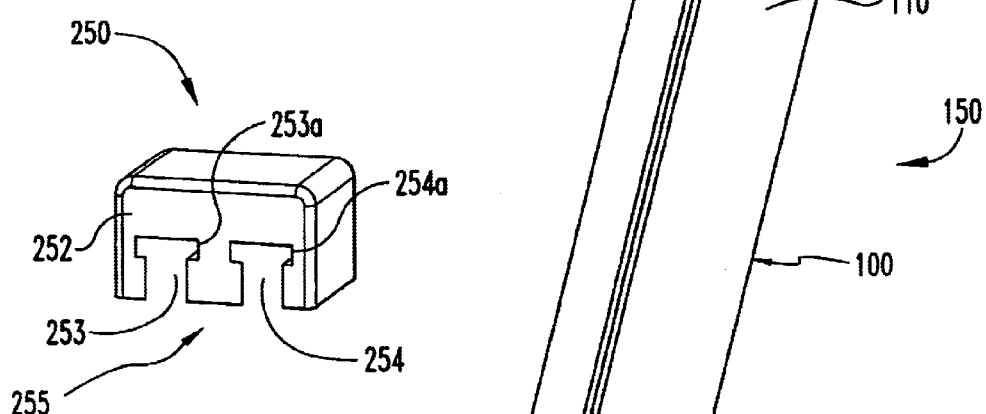
Figure 11:
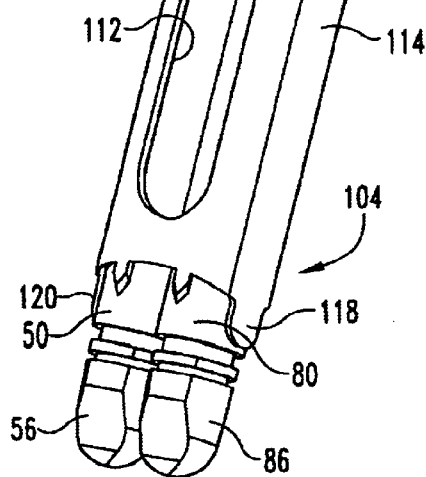
FIG. 11 is a perspective view of the guide sleeve assembly during insertion of the distractors into the disc space.

In accordance with a preferred method of using the apparatus of the present invention, reference will now be made to FIGS. 11 through 22. In FIG. 11, the sleeve assembly is assembled and prepared for insertion through the skin and to the disc space. Distractor driver cap 250 of FIGS. 11a and 11b is positioned on proximal end 53, 83 of distractors 50, 80. Driver cap 250 includes a body 252 having T-shaped slots 253 and 254 configured to receive flanged posts 53a and 83a of distractors 50 and 80, respectively. Opposite slots 253, 254 are windows 256 and 257. Preferably, the flanged portion of posts 53a and 83a extend into a corresponding one of the windows 256 and 257 and also into a corresponding one of the upper portions 253a and 254a of slots 253 and 254 to secure driver cap 250 to distractors 50, 80.

In use, distractor cap 250 contacts flange ring 155 with distractors 50, 80 in sleeve 100 such that distractor tips 56, 86 can be driven into the disc space while flanges 118, 120 remain positioned outside the disc space. The driving force applied to distractor cap 250 is transmitted to flange ring 155, and drives sleeve 100 towards the disc space along with distractors 50, 80. Alternatively, if distractors 50, 80 are not positioned in guide sleeve 100, distractor cap 250 is secured to proximal ends 53, 83 and distractor tips 56, 86 are driven into the disc space. Distractor cap 250 is then removed and sleeve 100 placed over the inserted distractors 50, 80 and the procedure continues as discussed the disc space simultaneously enables the surgeon maintain the positioning of distractors 50, 80 and control the depth of insertion of distractor tips 56, 86 with respect to one another.

In FIG. 12a, an impactor cap 160 is disposed about proximal end 102 of sleeve 100 over flange ring 155. Sleeve 100 is now relatively free to move with respect to distractors 50, 80. A driving force is applied to impactor cap 160 to drive sleeve 100 towards the disc space and position flanges 118 and 120 therein adjacent the distractor tips 56, 86 already positioned into the disc space as shown in FIG. 12b. Preferably, flanges 118 and 120 do not distract the disc space and prevent migration of tissue into the working space when distractor 50, 80 is removed from sleeve 100.

As shown in greater detail and enlarged FIG. 13, impactor cap 160 is positioned around and contacts the flange ring 155. Flange ring 155 is preferably of uniform size and shape for various sized guide sleeves 100, thus providing a modular attachment to each of the various sized guide sleeves for a single impactor cap 160. Impactor cap 160 has a hollow interior 161 for receiving proximal ends 53, 83. Hollow interior 161 has a depth d sufficient to allow movement of guide sleeve 100 into the disc space while the position of distractors 50, 80 is maintained.

In FIG. 14, a slap hammer 165 is engaged to distractor 50 in order to withdrawal distractor 50 from the disc space. In FIG. 15a the distractor 50 is removed from the working channel 130 of sleeve 110 using the slap hammer 165. The distractor tip 86 of concave distractor 80 remains disposed in the disc space to maintain the disc space distraction height during subsequent operative steps. In an alternate embodiment, it is contemplated that shaft 84 of distractor 80 is removably connected to tip 86, in which case the shaft may be withdrawn while leaving tip 86 in place. In a further embodiment, shaft 84 has a reduced size to accommodate insertion and rotation of devices into overlap region A of the disc space. With a removable or smaller diameter shaft, only tip 86 requires a recessed area.

In FIG. 15b, the withdrawn distractor 50 leaves a working space comprised of working channel portion 109 and an overlap portion, indicated by hatched area A. Thus, the concave surfaces 96, 98 of distractor 80 and inside surface 116 of sleeve 110 define a substantially cylindrical working space for completion of further operative procedures as described further below. The working space defines a substantially circular cross section along guide sleeve 100 that is adapted for receiving surgical tools therethrough to prepare the disc space for insertion of an implant. The overlapping configuration of distractors 50, 80 provides a reduced overall width for guide sleeve 100.

Figures 16A, 16B:
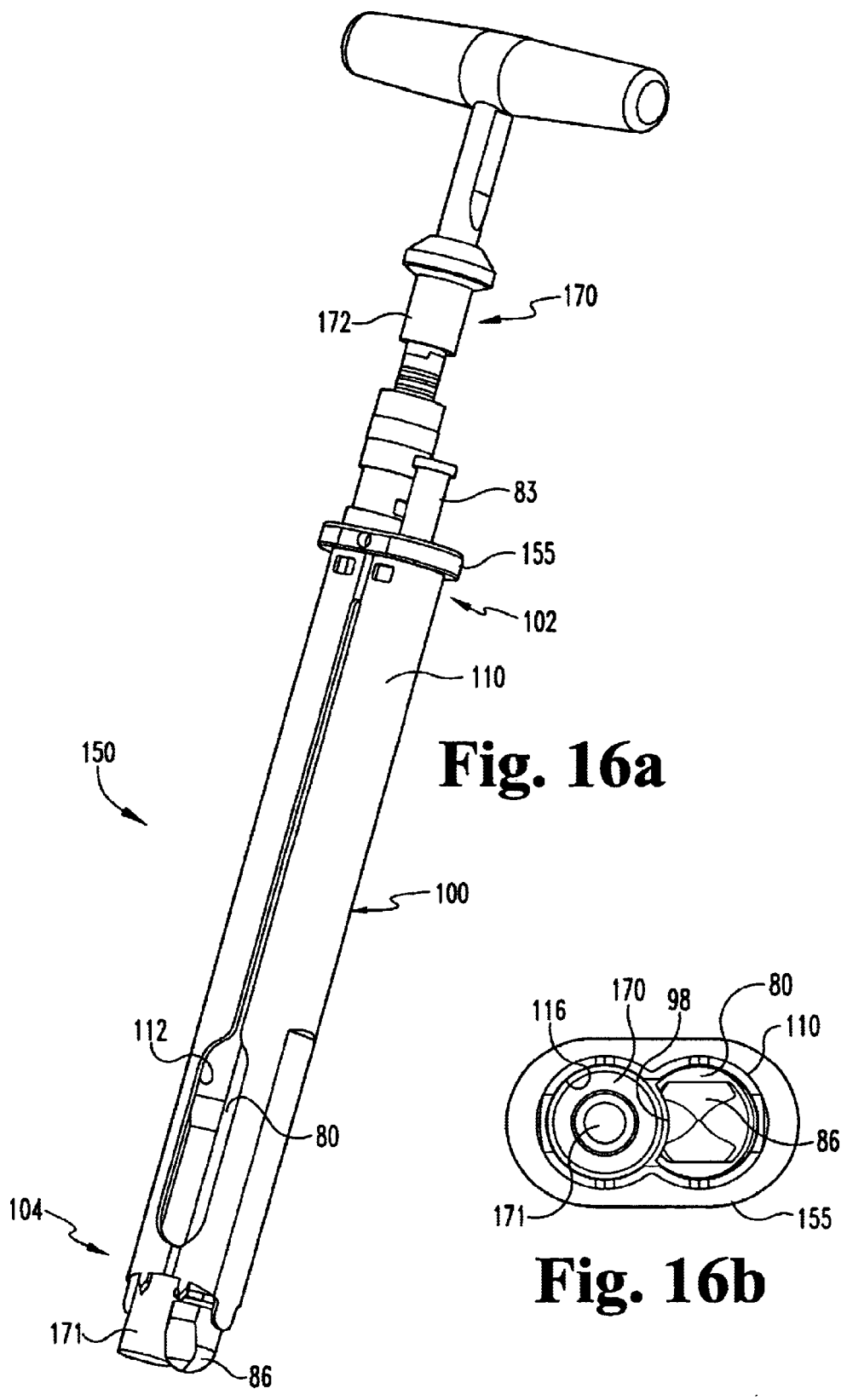
FIGS. 16a–16b are a perspective view and an end view, respectively, of the guide sleeve assembly with a reamer disposed adjacent a distractor.

In FIGS. 16a–16b, there is shown a reamer 170 disposed through guide sleeve 110. A cutting head 171 has cutting edges as known in the art to ream the disc space. As shown in FIG. 16b, reamer 170 is positioned within the working space adjacent distractor 80, while distractor tip 86 maintains the disc space distraction. Concave surface 98 of shaft 84 of distractor 80 and the inside surface 116 of sleeve 110 acts as a guide for insertion and/or withdrawal of reamer 170. The depth of reaming can be controlled with a depth stop 172 and verified via fluoroscopy In FIGS. 17a–17c, the reamer 170 is withdrawn and replaced by a tapping tool 175 with a head 176 to prepare the space for a threaded implant. As shown in FIGS. 17b and 17c, tapping tool 175 is positioned within the working space adjacent the concave distractor 80, while distractor tip 86 maintains the disc space distraction. The concave surface 98 of shaft 84 of distractor 80 and inside surface 116 of sleeve 110 acts as a guide for insertion of tapping tool 175. Tapping tool 175 has a depth stop 178 to control the tapping depth in the disc space. Depth and sagittal alignment can also be verified via fluoroscopy during tapping.

Figures 18A, 18B:
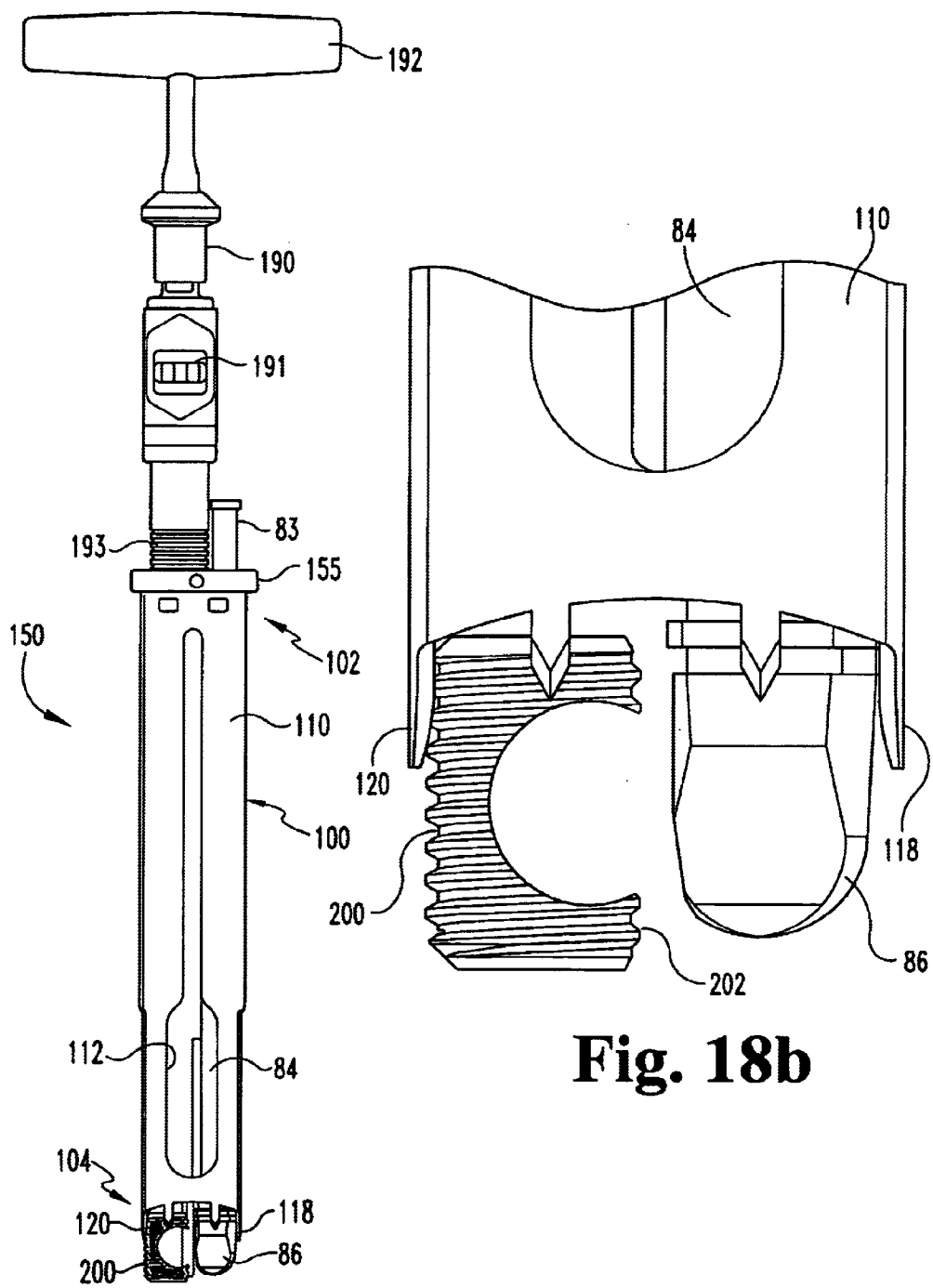
FIGS. 18a–18c are a perspective view, detail view and end view, respectively, of the guide sleeve assembly with an implant disposed adjacent a distractor.
Figure 18C:
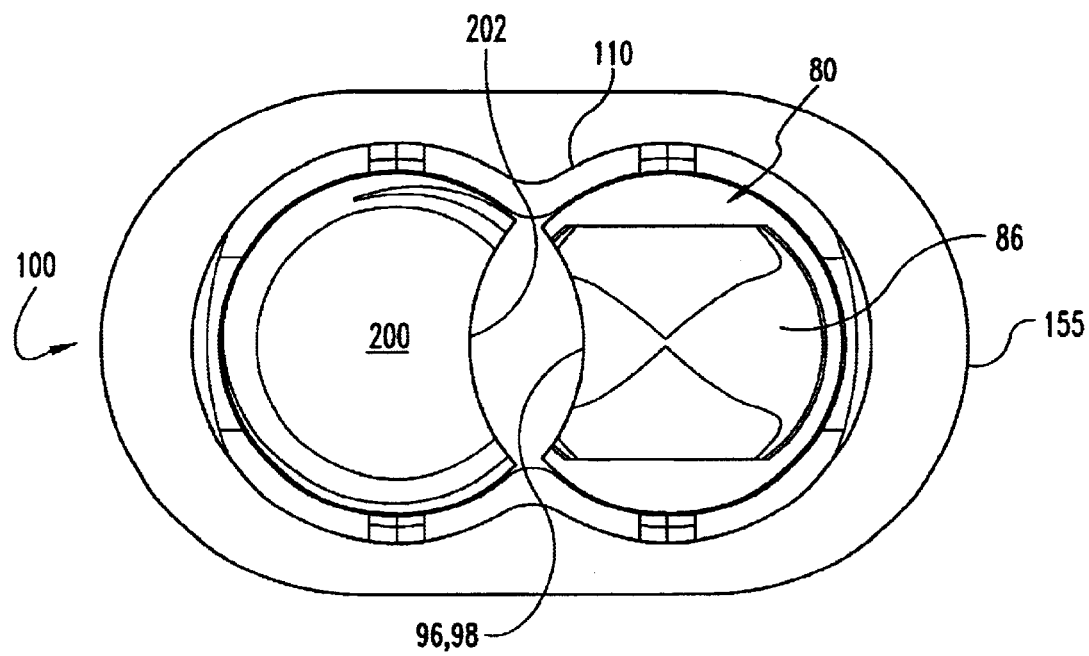

In FIGS. 18a–18c, the tapping tool 175 is withdrawn and replaced by an implant insertion device 190 with a threaded implant 200 engaged on a distal end thereof. Threaded implant 200 and insertion device 190 may be any one of the types and configuration disclosed in a first pending PCT Application No. PCT/US00/00590 filed on Jan. 11, 2000 and a second PCT Application No. PCT/US00/00604, also filed Jan. 11, 2000; each claiming priority to U.S. Provisional Application No. 60/115,388, filed Jan. 11, 1999, each of said above referenced PCT applications being incorporated by reference herein in its entirety. Further, the implants of the present invention may be any other known implant and insertion device, so long as at least one implant has at least one recessed side wall. The implants may be formed of any biocompatible material. Concave surface 98 of shaft 84 of distractor 80 and inside surface 116 of sleeve 110 acts as a guide for insertion of the implant into the disc space.

Inserter 190 includes a thumbscrew 191 having a threaded shaft (not shown) extending through inserter 190 to couple implant 200 thereto via an internally threaded opening in a slotted end 201 (FIG. 19) of implant 200. T-handle 192 is used to rotate implant 200 and thread it into the disc space, as shown in the enlarged view of FIG. 18b. As shown more clearly in the enlarged view of FIG. 18c, implant 200 is inserted so that a concave face 202 is disposed toward concave surface 96 of distractor 80. This positioning of concave face 202 can be confirmed by providing alignment markings on insertion device 190 and sleeve 100. Further, insertion device 190 includes countersink marking 193 to provide an indication of the countersink of implant 200 into the disc space. To facilitate implant rotation, inserter 190 can be provided with a movable slide at its distal end that occupies the recessed area of concave surface 202 providing a round construct for threading. While implant 200 is threaded into place, distractor tip 86 maintains the disc space distraction.

Figures 19A, 19B, 19C:
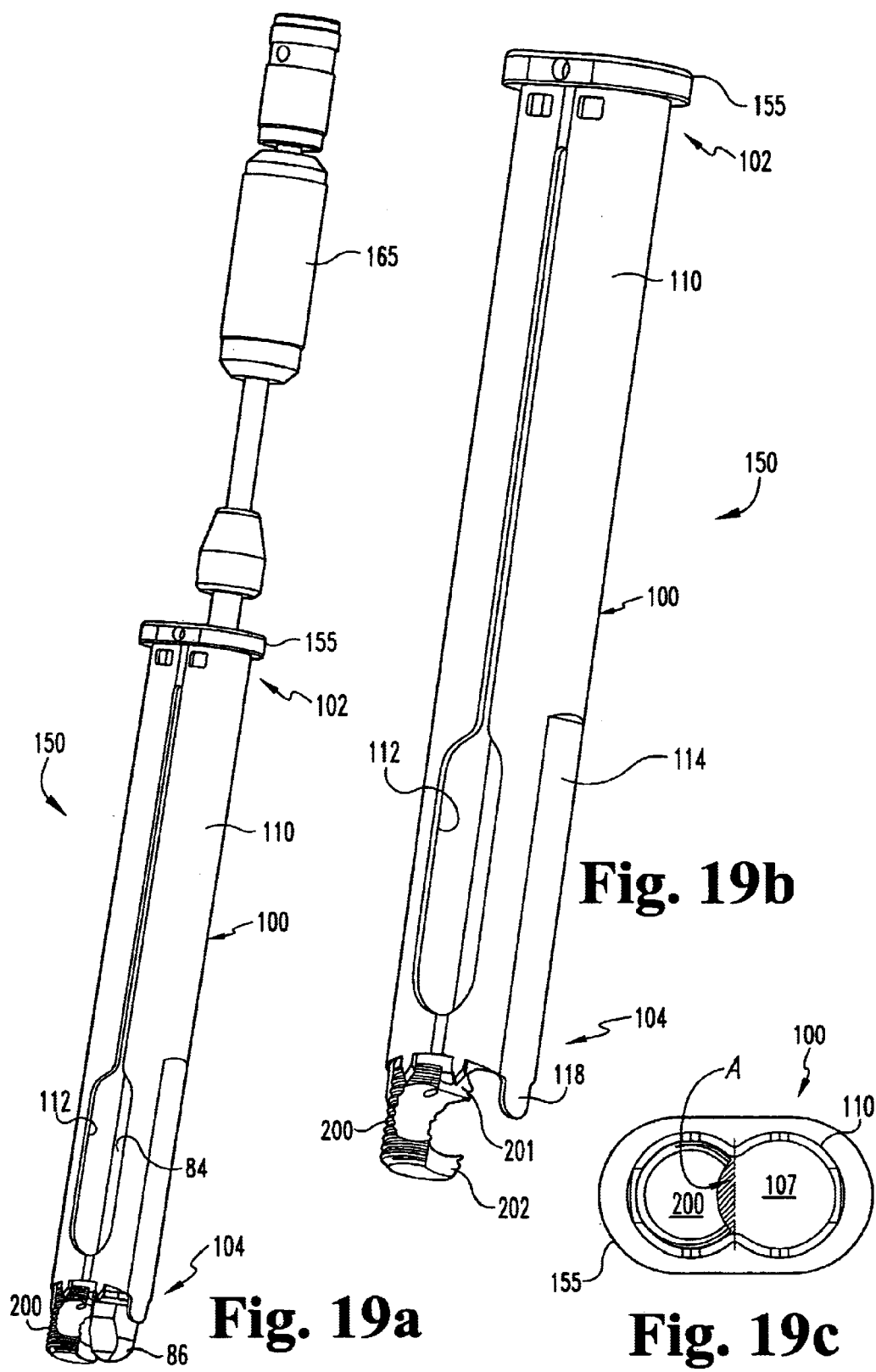
FIGS. 19a–19c are perspective views and an end view, respectively, of the guide sleeve assembly showing withdrawal of the other distractor.

In FIGS. 19a–19b, when implant 200 is placed in the desired position, and implant inserter 190 is removed from guide sleeve 100, distractor tip 86 is withdrawn from the disc space. Preferably, a slap hammer 165 is engaged to distractor 80 in order to withdraw distractor tip 86 from the disc space and distractor 80 from guide sleeve 100. As shown in FIGS. 19b–19c, distractor 80 is removed from working channel 130 of sleeve 110. Implant 200 remains disposed in the disc space to maintain the disc space distraction height during subsequent operative steps. The withdrawn distractor 80 leaves a working space comprised of working channel portion 107 and an overlap region A. Thus, concave surface 202 of implant 200 and inside surface 116 of sleeve 110 define a cylindrical working space in the disc space for further procedures as described below. The working space defines a circular cross section that is adapted for receiving conventionally sized surgical tools to prepare the disc space for insertion of a second implant adjacent implant 200, while providing a reduced overall width.

Figures 20A, 20B:
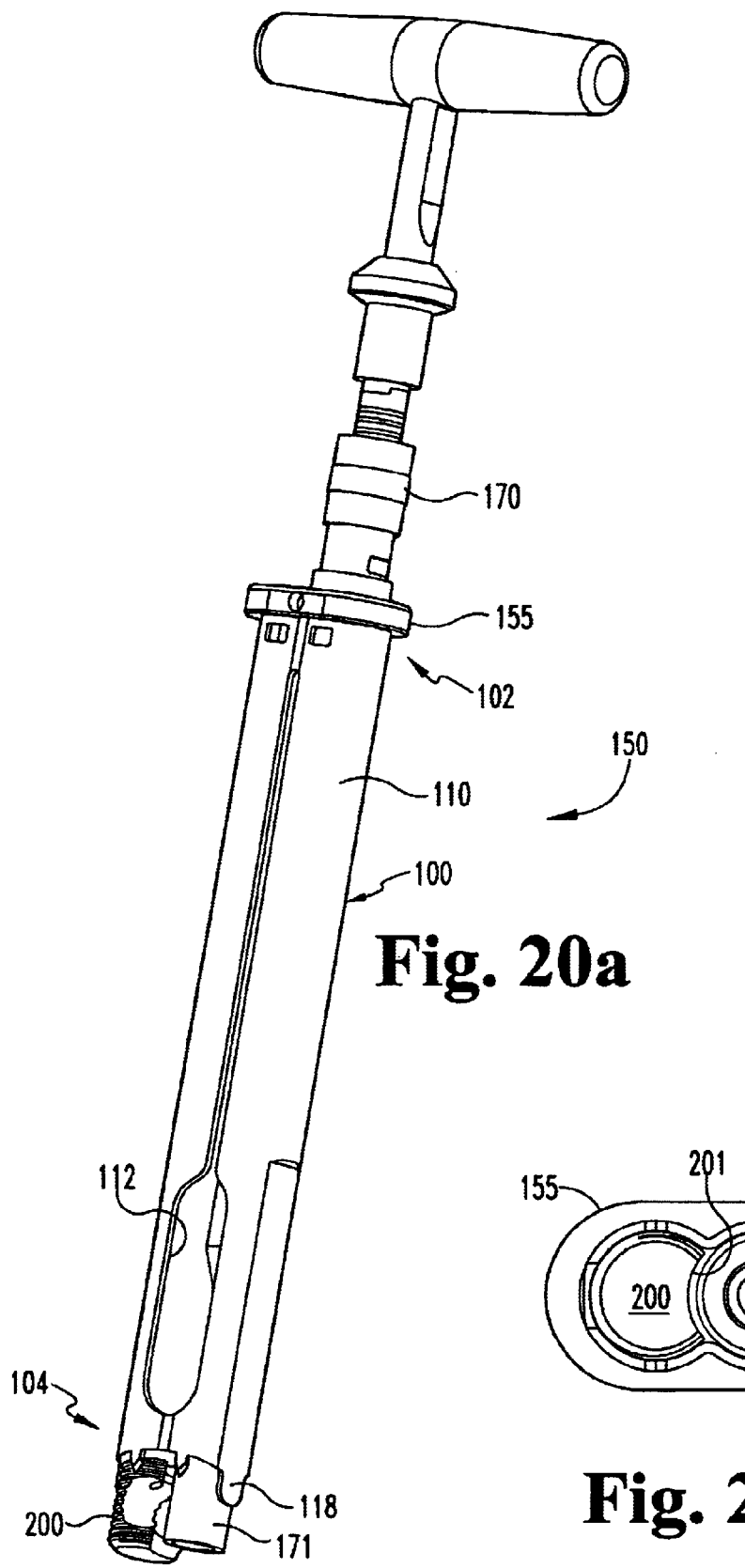
FIGS. 20a–20b are a perspective view and an end view, respectively, of the guide sleeve assembly with a reamer disposed adjacent an implant.

In FIGS. 20a–20b, the above described reamer 170 is disposed through guide sleeve 110. Cutting head 171 has threads as known in the art to ream the disc space. As shown in FIG. 20b, reamer 170 is positioned within the working space adjacent the concave surface 201 of implant 200, while implant 200 maintains the disc space distraction. The concave surface 201 of implant 200 and inside surface 116 of sleeve 110 acts as a guide for insertion and operation of reamer 170.

Figures 21A, 21B, 21C:
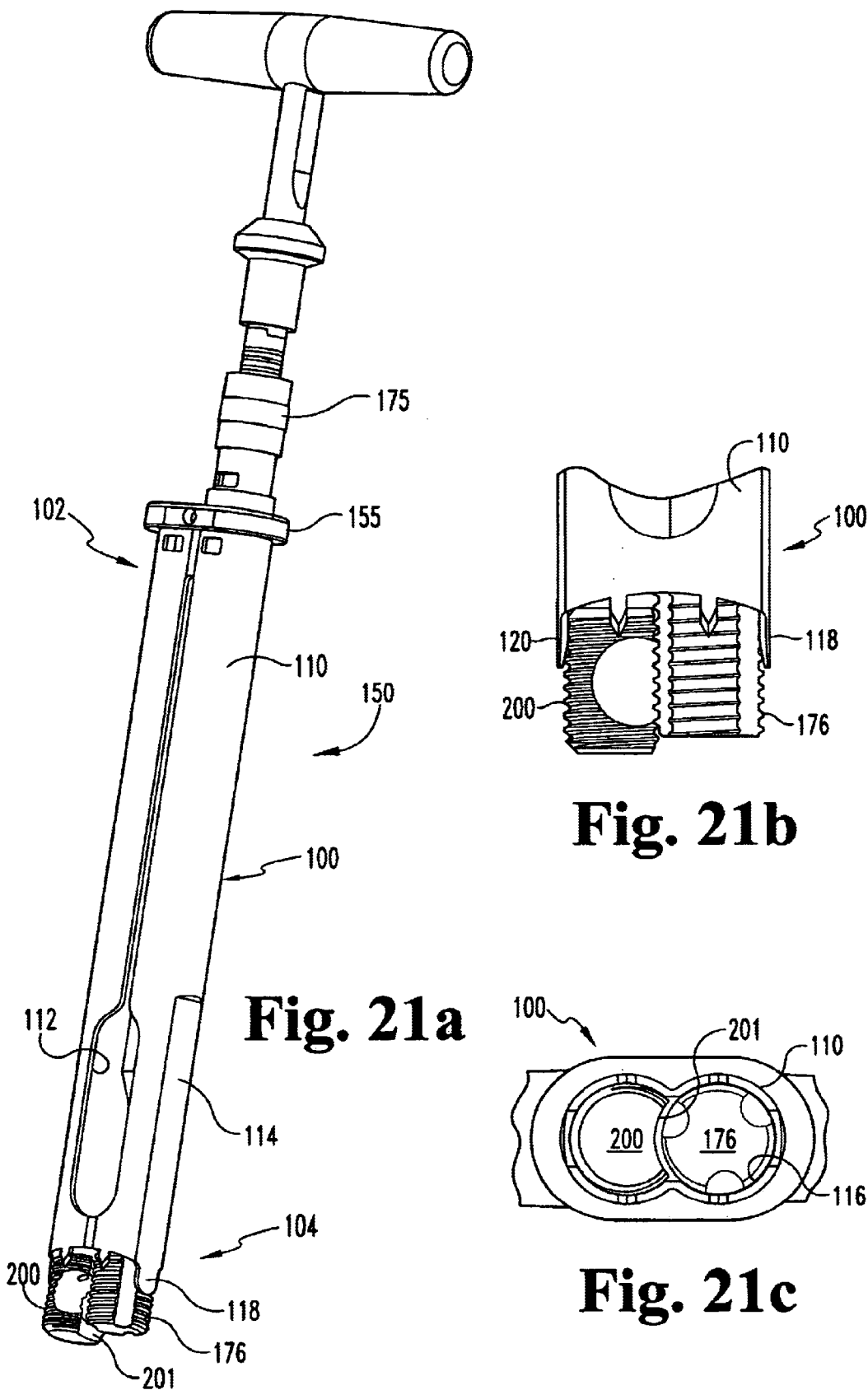
FIGS. 21a–21c are a perspective view, detail view and end view, respectively, of the guide sleeve assembly with a tap disposed adjacent an implant.

In FIGS. 21a–21c, reamer 170 is withdrawn and replaced by the above-described tapping tool 175 with head 176 to prepare the space for a second threaded implant. As shown in FIGS. 21b and 21c, head 176 of tapping tool 175 is positioned within the working space adjacent concave surface 201 of implant 200, while implant 200 maintains the disc space distraction. The concave surface 201 and inside surface 116 of sleeve 110 acts as a guide for insertion of tapping tool 175.

Figure 22C:
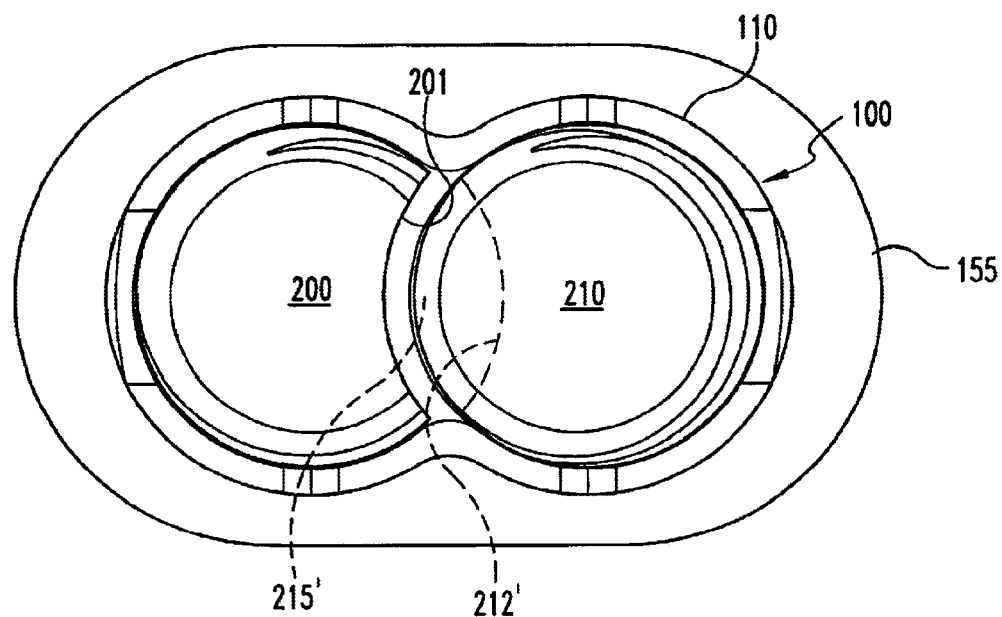
FIGS. 22a–22c are a perspective view, detail view and end view, respectively, of the guide sleeve assembly with an implant disposed adjacent an implant.
Figures 22A, 22B:
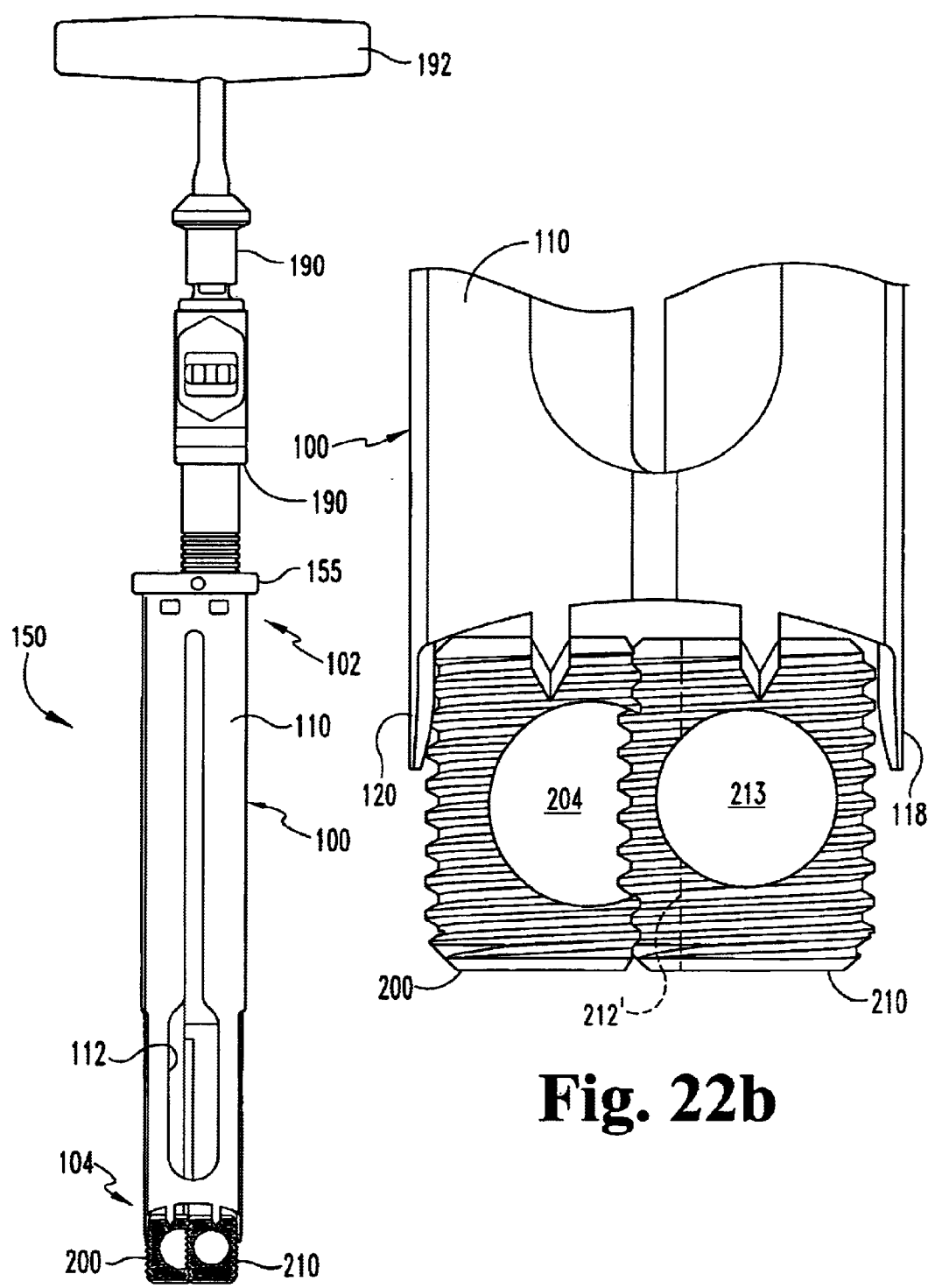

In FIGS. 22a–22c, the tapping tool is withdrawn and replaced by the above described implant insertion device 190, with a threaded implant 210 engaged on a distal end thereof. Threaded implant 210 may either have a circular cross-section, such as that shown in solid lines in enlarged FIGS. 22b and 22c, or have a cross-section identical to implant 200 with a concave surface 202 as shown in hidden lines. In either event, concave surface 201 of implant 200 acts as a guide for threading of implant 210 into the disc space.

If an implant like that of implant 200 is used, it is preferred to position implant 210 so that its concave surface 212' is disposed towards concave surface 202 of implant 200, forming a cavity 215' therebetween as indicated in dashed lines in FIG. 22c. The cavity may then be packed with bone growth promoting material. T-handle 192 is used to rotate implant 210 and thread it into the disc space, as shown in FIG. 22b, adjacent to implant 200. If a circular implant similar to that shown in FIG. 22c is used, implant 210 is nested within concave surface 201 of implant 200. Bone growth material can be placed in cavity 204 of implant 200 and in cavity 213 of implant 210.

The present invention further contemplates instruments and methods particularly suited for inserting threaded fusion devices into a disc space between vertebrae from an anterior approach to the lumbar region of the spine. It is further contemplated that these threaded devices can be self-tapping and tapered to establish lordosis between the vertebral endplates when inserted in the disc space therebetween. Examples of such cages are provided in U.S. Pat. Nos. 5,669,909 and 5,782,919, each of which is incorporated herein by reference in its entirety. While the instruments and methods described below are contemplated for use with tapered, threaded fusion devices and for use in an anterior approach to the lumbar region of the spine, aspects of the instruments and methods may also have application in other approaches to the spine and in the insertion of other types and shapes of implants into the disc space.

Figure 23A:
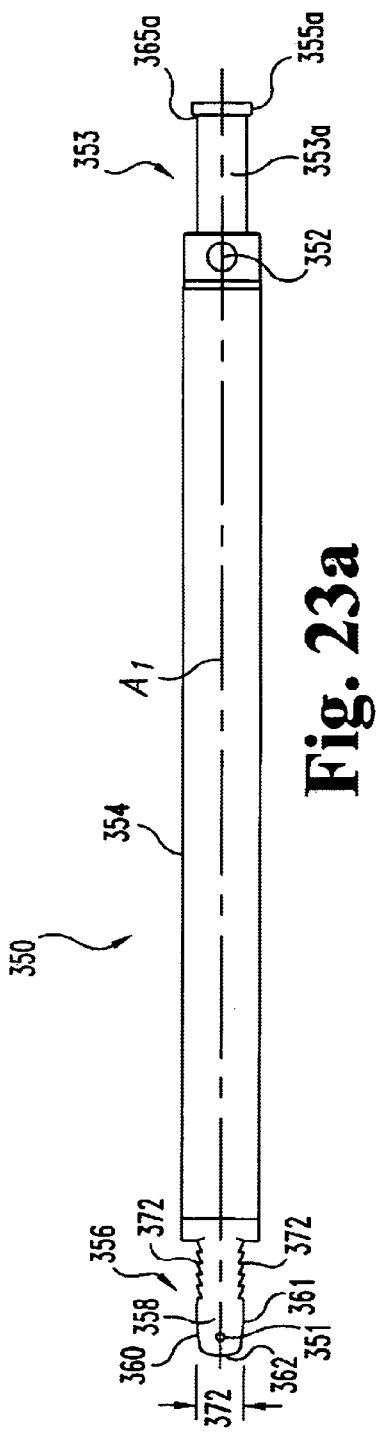
FIG. 23a is an elevational view of another embodiment first distractor according to the present invention.
Figure 23B:
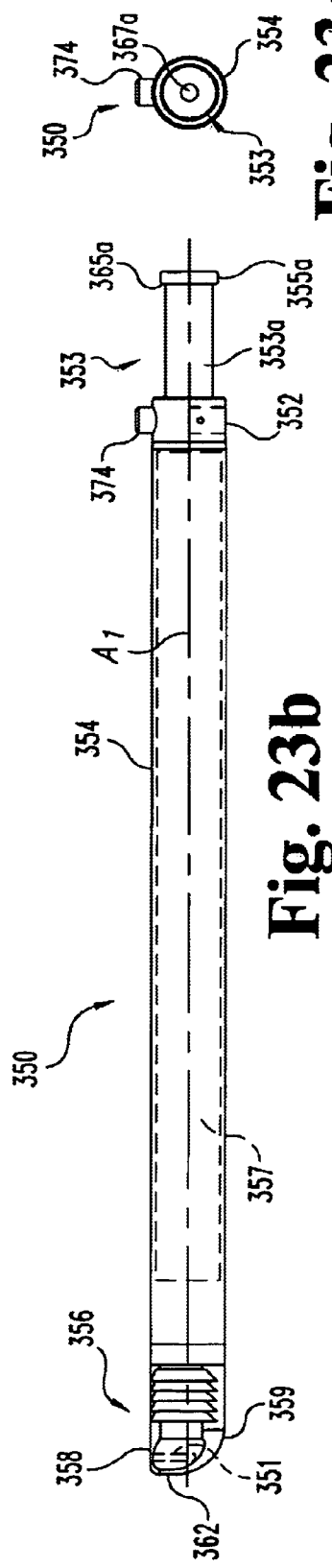
FIG. 23b is an elevational view of the distractor of FIG. 23a rotated 90 degrees about its longitudinal axis.
Figure 23C:
FIG. 23c is a right end view of the distractor of FIG. 23b.

Referring now to FIGS. 23a–23c, there is shown another embodiment of a convex or first disc space distractor 350 that is, except as described hereinbelow, similar in many respects to first distractor 50 of FIGS. 1a–1c. Distractor 350 includes a proximal end 353, a shaft 354 extending along longitudinal axis A1, and a distractor tip 356 at the distal end of shaft 354. Proximal end 353 includes a flanged post 353a having a proximal flange 355a on the end of the post defining a lip 365a thereabout. A hole 367a is provided in the proximal face of flange 355a and configured to attach distractor 350 to conventional tools such as a distractor puller.

In the illustrated embodiment, shaft 354 has a hollow interior 357 to reduce its weight; however, the present invention also contemplates a solid shaft 354. Also, while an integral shaft and tip are shown, distractor tip 356 may be removably attached to shaft 354. Distractor tip 356 can be provided with a rounded leading edge 362 that extends between a medial side 358 and an opposite lateral side 359 of distractor 350. Preferably, for reasons described further below, the transition between leading end 362 and medial side 358 is relatively abrupt such that leading edge 362 remains extended to its most distal-most point at the transition therebetween. A gradual arcuate transition is provided between lateral side 359 and leading edge 362. Distractor tip 356 also includes opposing vertebral contacting surfaces 360 and 361, which can each include serrations 372 to engage the vertebral endplates and resist movement of distractor tip 356 in the disc space. Distractor tip 356 is designed such that it can be inserted in a disc space to establish a distraction height 372 (see FIG. 23a) between the vertebral endplates. Distractor tip 356 is preferably made from aluminum or other radiolucent material, and includes a radiographic marker 351 to allow the surgeon to determine and monitor distractor tip 356 during insertion into the disc space. Shaft 354 and flanged post 353a, and in the alternative tip 356, can be made from stainless steel or other acceptable material for surgical instruments.

Distractor 350 further includes a projection 374 that is cylindrically shaped, although other shapes are also contemplated, that extends medially from medial side 358. The significance of projection 374 will be discussed further below. A color-coded marker 352 is provided in shaft 354 to give the surgeon an indication of the size of distractor tip 356.

Referring now to FIGS. 24a–24c, there is shown a second disc space distractor 380 that is, except as described hereinbelow, similar in many respects to second distractor 80 of FIGS. 2a–2c. Distractor 380 includes a proximal end 383, a shaft 384 extending along axis B1, and a distractor tip 386 at the distal end of shaft 384. Proximal end 383 includes a flanged post 383a having a proximal flange 385a on the end of the post defining a lip 395a thereabout. A hole 397a is provided in the proximal face of flange 385a that is configured to attach distractor 350 to conventional tools such as a distractor puller.

In the illustrated embodiment, shaft 384 has a hollow interior 387 to reduce its weight; however, the present invention also contemplates a solid shaft 384. Also, while an integral shaft and tip are shown, distractor tip 386 may be removably attached to shaft 384. Distractor tip 386 can be provided with a rounded leading edge 392 that extends between a medial side 388 and an opposite lateral side 389 of distractor 380. Preferably, for reasons described further below, the transition between leading end 392 and medial side 388 is relatively abrupt such that leading edge 382 remains extended to its most distal-most point at the transition therebetween. A gradual arcuate transition is provided between lateral side 389 and leading edge 392. Distractor tip 386 also includes opposing vertebral endplate contacting surfaces 390 and 391, which can include serrations 392 to engage the vertebral endplates and resist movement of distractor tip 386 in the disc space. Distractor tip 386 is designed such that it can be inserted in a disc space to establish a distraction height 372' (see FIG. 24a) between the vertebral endplates. Distractor tip 386 is preferably made from aluminum or other radiolucent material, and includes a radiographic marker 381 to allow the surgeon to determine and monitor distractor tip 386 during insertion into the disc space. Shaft 384 and proximal end 386, and in the alternative tip 386, can be made from stainless steel or other acceptable material for surgical instruments.

Figure 25A:
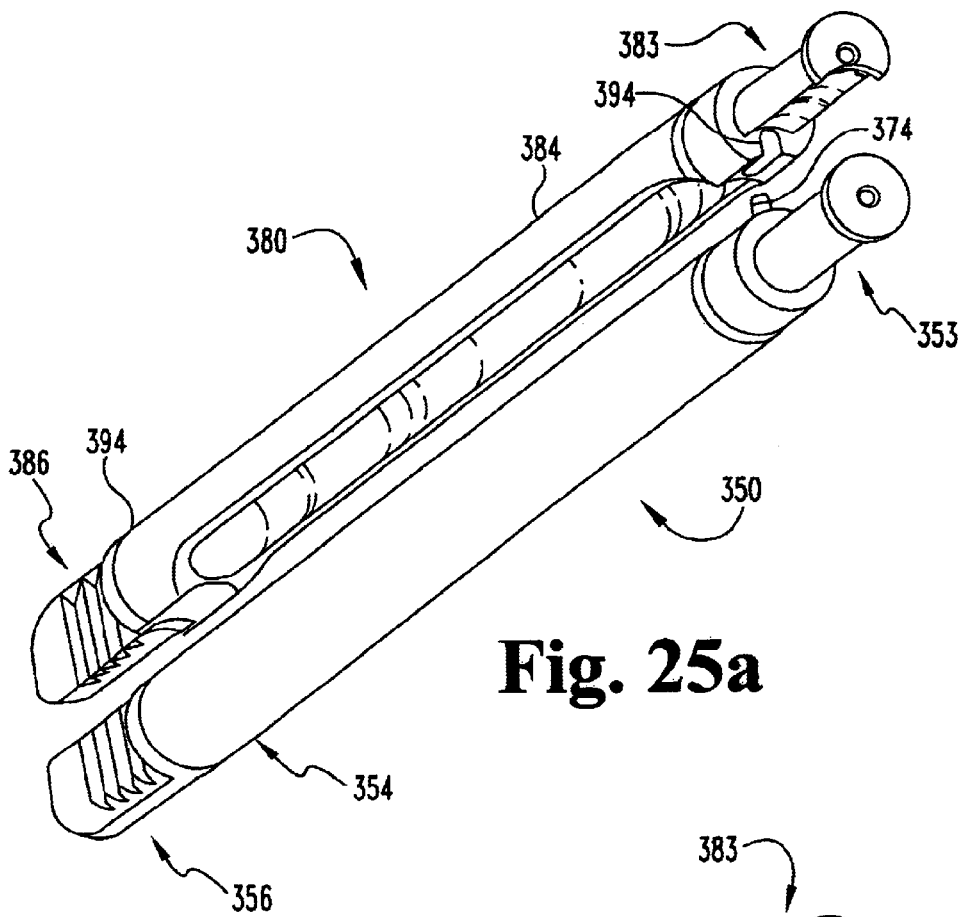
FIGS. 25a and 25b show the assembly of the distractors of FIGS. 23a–c and FIGS. 24a–c in side-by-side relation.
Figure 25B:
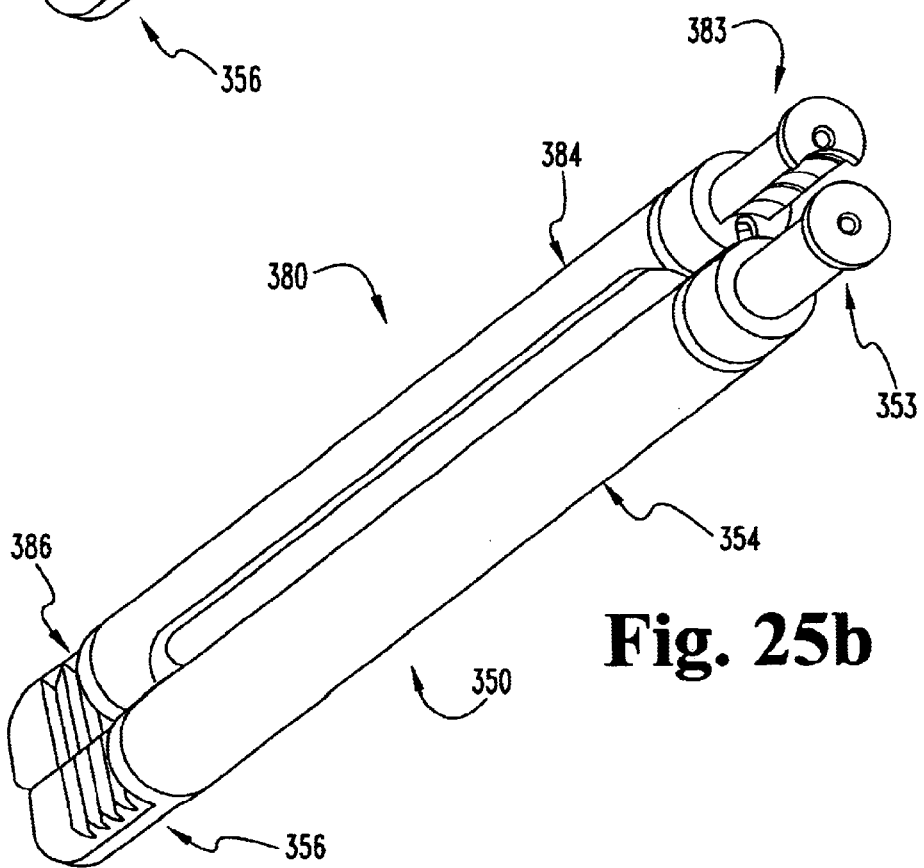

Extending along medial side 388 of distractor 380 extending from leading edge 392 to proximal flange 385 is a recessed area defined by a scalloped or concave surface 394. In the illustrated embodiment, concave surface 394 has a window 399 formed therein communicating with the hollow interior 387 of shaft 384. In a manner similar to that discussed above with respect to distractors 50 and 80, concave surface 394 mates with the convex medial surface 358 of first distractor 350 when distractors 350 and 380 are disposed with medial sides 358 and 388 in side-by-side relation as shown in FIGS. 25a and 25b. Thus distractors 350, 380 form an overall reduced width for the adjacent distractors. The leading ends 362, 392 form a single blunt leading end for the adjacent distractors 350, 380 when assembled.

To aid in distractor insertion, distractor 380 includes a notch 396 formed in the adjacent the proximal end of shaft 384 sized to receive projection 374 as shown in FIGS. 25a and 25b. Notch 396 has a proximally facing opening 398 that allows projection 374 to be top-loaded therein from the proximal direction and withdrawn therefrom in the distal direction when distractors 350, 380 are adjacent one another. Projection 374 and notch 396 resist rotation of distractors 350, 380 relative to one another and maintain the relative positioning of distractors 350, 380 during insertion into the disc space.

Specifically, but without limitation, the distractor tips 356, 386 may be formed with heights 372, 372' ranging from 6 mm to 24 mm. Preferably, the height of the next sized distractor increases or decreases in 2 mm increments. Other variations and may be provided as long as the working distractor height provided approximates the disc height in a normal spine and accommodates insertion of an implant into the disc space as described herein.

Referring now to FIGS. 26a–26c, there is shown a guide sleeve 400 that receives distractors 350, 380 described above. Guide sleeve 400 is similar to guide sleeve 100 and can also receive distractors 50, 80. Guide sleeve 400 has a wall defining a working channel 430 having a figure eight shaped cross-section. Working channel 430 extends in a substantially unobstructed manner from a proximal end 402 to a distal end 404. Distal end 404 is concave to match the contour of the anterior aspect of the vertebral bodies against which it is positioned. Sleeve 400 also includes an elongated visualization window 412 centered about the longitudinal axis L6 with a tapered portion 411 extending proximally from window 412 and blending into wall 410. As discussed above with respect to window 112 of guide sleeve 100, window 412 provides the surgeon with the ability to visualize the instruments inserted in working channel 430 of guide sleeve 400 as well as the openings in the disc space and vertebral bodies.

Adjacent distal end 404, the material thickness along the lateral edge portions wall 410 is reduced in order to provide a reduced thickness wall portion 414 and an opposite reduced thickness wall portion 415 in a manner similar to that discussed above with respect to guide sleeve 100. Guide sleeve 400 includes a pair of flanges 418 and 420 extending from distal end 404 on opposite sides of working channel 430. Flanges 418 and 420 are configured to extend partially into the disc space, and are each an extension of the corresponding reduced thickness wall portions 414, 415 described above. Preferably, as discussed above with respect to guide sleeve 100 and flanges 118 and 120, flanges 418 and 420 do not provide distraction of the disc space but are primarily provided to protect surrounding vessels and neurological structures from damage during the procedures. Since flanges 418, 420 do not provide structural support for distraction, the material thickness of the flanges and adjacent side walls may be reduced.

Guide sleeve 400 also includes a first working channel portion 407, defined about axis L7, and a second working channel portion 409, defined about axis L8. These working channel portions 407, 409 are positioned on either side of longitudinal axis L6 of sleeve 400. There is no wall or other structure separating working channel portions 407 and 409. As discussed above with respect to guide sleeve 100 and working channel portions 107, 109, working channel portions 407 and 409 are substantially equal in area, and each has a truncated circular shape, with the truncated portions of each working channel 407 and 409 positioned adjacent one another.

A sleeve cap 455 is provided at proximal end 402 and is welded, integrally formed with, or otherwise attached to wall 410 of sleeve 400. Sleeve cap 455 includes a proximal groove 406 formed therein adjacent proximal end 402 that defines a proximal end ring 407 around sleeve 400. Sleeve cap 455 also includes a circumferential ring member 408 extending therearound and positioned distally of proximal groove 406. As described further below, sleeve cap 455 facilitates connection of driving caps to sleeve 400 and the assembly of distractors 350, 380 with sleeve 400.

A side-loading distractor driver cap 550 is shown in FIG. 27a–27d. Distractor driver cap 550 includes a body 552 having an upper portion 554 and a lower attaching portion 556. Attaching portion 556 has a side opening 558 that communicates with a distractor securing portion 560 and a sleeve securing portion 562 provided in the interior of attaching portion 556. Distractor securing portion 560 and sleeve securing portion 562 are configured to allow distractor driver cap 550 to be side-loaded through side opening 558 onto the distractor assembly 450 (FIG. 28) to assemble distractors 350, 380 and guide sleeve 400.

Figure 28:
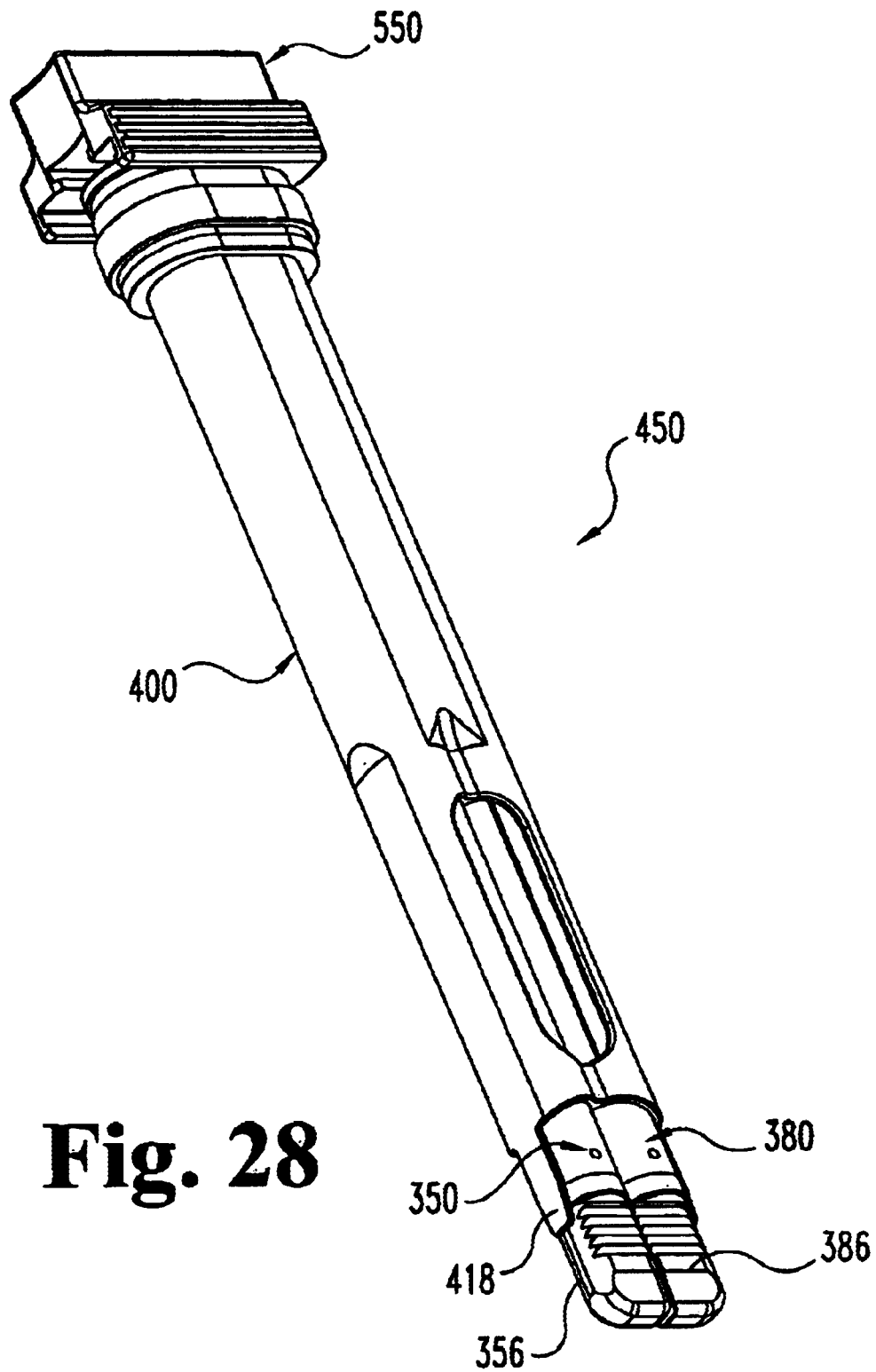
FIG. 28 shows a distractor assembly secured to the distractor driver cap of FIGS. 27a–27d.

Distractor securing portion 560 includes a distractor slot 564 having a first ledge 568 therearound formed by upper extension 567. Distractor slot 564 is configured to receive proximal flanges 355a and 385a of flange posts 353a and 383a, respectively, of distractors 350, 380 when positioned together as shown in FIG. 25b. Lips 365a and 395a of flange posts 353a and 383a, respectively, contact first ledge 568 formed around distractor slot 564. Sleeve securing portion 562 includes a sleeve slot 566 having a second ledge 570 therearound formed by a bottom extension 572. Sleeve slot 566 is configured to receive proximal end ring 407 of sleeve 400 with bottom extension 572 positioned in proximal groove 406 when distractors 350, 380 are inserted into sleeve 400 as shown in FIG. 28. Distractor driver cap 550 secures distractors 350, 380 together and also secured distractors 350, 380 relative to guide sleeve 400 forming distractor assembly 450. This allows the surgeon to insert distractor assembly 450 through skin and tissue to the disc space without distractors 350, 380 and sleeve 400 moving relative to one another. Preferably, distractor tips 356, 386 extend distally beyond the flanges 418, 420 to the distractor tips can be inserted into the disc space without inserting flanges 418, 420 into the disc space.

Figure 27A:
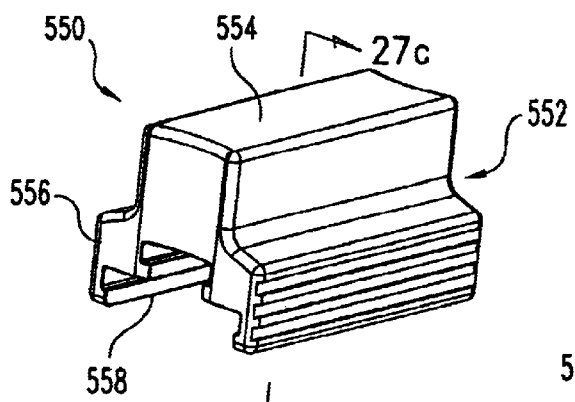
FIGS. 27a and 27b are a top perspective view and a bottom perspective view of a distractor driver cap according to a further aspect of the present invention.
Figure 27B:
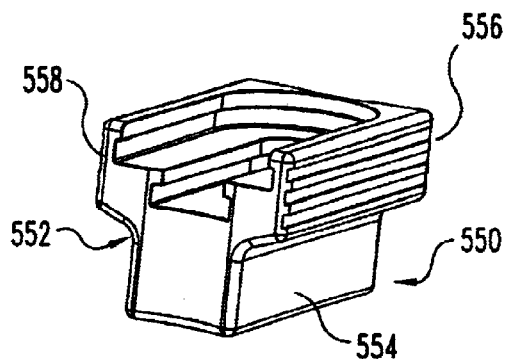
Figure 27C:
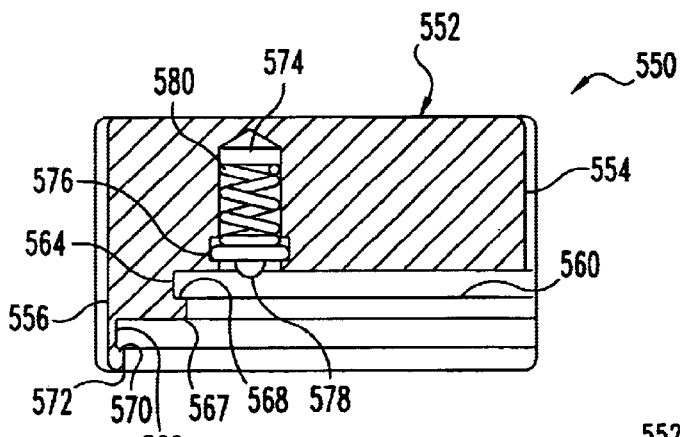
Figure 27D:
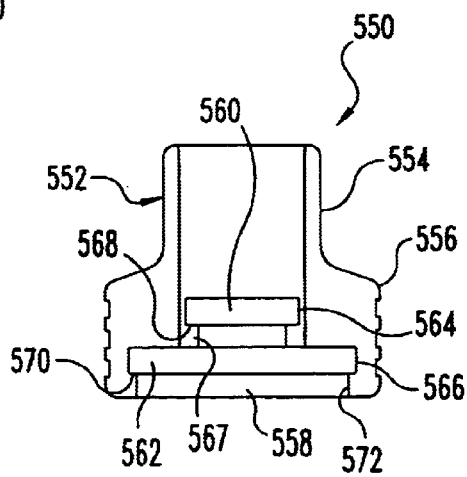

Referring to FIG. 27c, upper portion 554 is preferably solid to deliver a driving force to the proximal flanges 355a, 385a of distractors 350, 380 respectively. To ensure side-loading distractor driver cap 550 is properly positioned on distractors 350, 380, a well 574 is provided in upper portion 554 in communication with distractor securing portion 560. A spring-biased plunger 576 has a nub 578 extending into distractor securing portion 560. When one of the proximal flanges 355a, 385a contacts nub 578, spring 580 compresses and plunger 576 is pushed into well 574. Depending on the side from which distractor driver cap 550 is loaded, one of the holes 367a, 397a will align with nub 578 and spring 580 pushes nub 578 into the corresponding hole 567a, 597a. This creates a clicking sound and an audible indication that distractor driver cap 550 is properly seated on the distractors 350, 380.

In FIG. 29, there is shown a reamer 470 positionable through a selected one of the working portions 407, 409 of guide sleeve 400. Reamer 470 includes a cutting head 471 attached to the distal end of a shaft 474. Cutting head 471 has cutting blades 476 extending in a helical pattern from a body 478 configured to ream a cylindrical hole in a disc space. Body 478 has elongated openings 480 formed therethrough along each cutting blade 476 that communicate with a hollow interior defined by body 478. A port 482 in shaft 474 provides access to the interior of body 478 for material removal therefrom. An opening (not shown) in the distal end of body 478 can also be provided for this purpose. The depth of reaming can be monitored and controlled with a depth stop, such as depth stop 172 of FIG. 16*a*, and depth markings 484 on shaft 474. A connector 486, such as a Hudson type connector, is provided at the proximal end of shaft 474 for connection with a T-handle driving tool.

Referring now to FIGS. 30*a*–30*b*, a reamer plug 600 is illustrated. Reamer plug 600 has a shaft 602 and a plug 604 at the distal end of shaft 602. A handle 606 is provided at the proximal end of shaft 602. Shaft 602 is generally cylindrical but includes a concave surface 612 extending along a medial side thereof to accommodate rotation of a tool therebeside. Handle 606 has a scalloped portion 608 connected to shaft 602. Scalloped portion 608 has a cavity 614 formed around shaft 602 that receives the proximal end of guide sleeve 400 when reamer plug 600 is fully inserted therein to clock shaft 604 against the sidewall of guide sleeve 400. Handle 606 further includes a laterally extending portion 610 that extends away from shaft 602 opposite concave surface 612 that facilitates insertion and removal of plug 604 into the reamed disc space location. The scalloped portion 608 and laterally extending portion 610 provide clear access to one of the working channel portions 407, 409 of guide sleeve 400 when reamer plug 600 is disposed in the other working channel portion 407, 409.

Referring now to FIG. 31, there is shown an implant adjuster 620. Implant adjuster 620 has a shaft 622 extending between a proximal end 624 and a distal end 626. As discussed further below, distal end 626 has an implant engaging portion 628 configured to engage an implant that has been implanted into the disc space to provide adjustment of the final alignment of the implant. Proximal end 624 can be provided with a Hudson-type connector connectable to a T-handle or the like to apply a rotational force to the implant through implant adjuster 600.

Figure 32A:
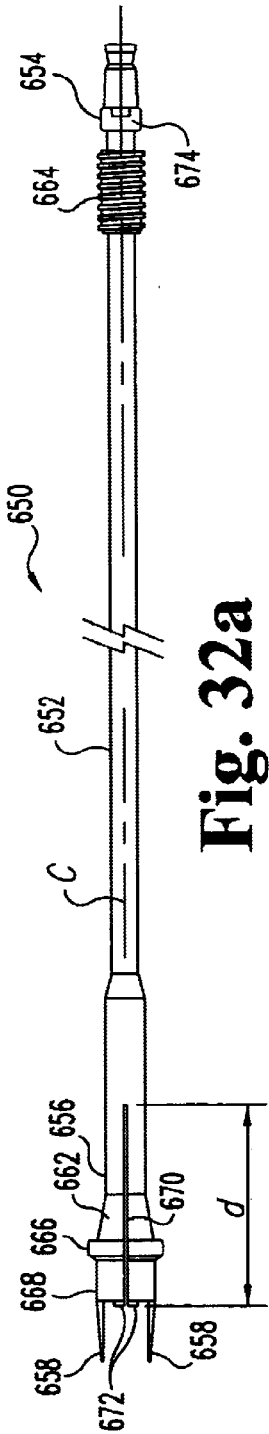
FIG. 32a is an elevational view of an implant holder according to the present invention.
Figure 32B:
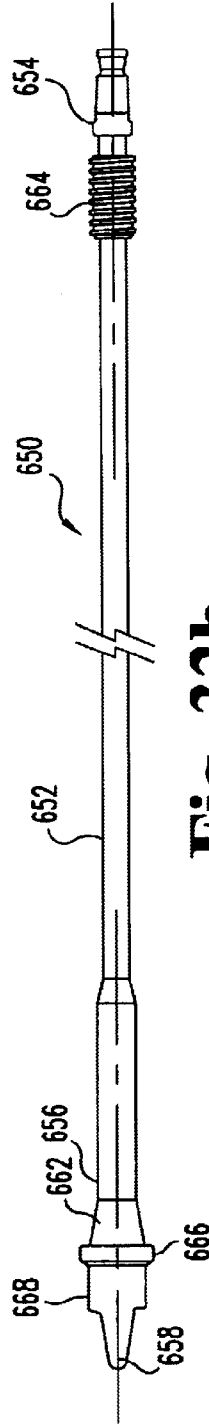
FIG. 32b is an elevational view of the implant holder of FIG. 32a rotated 90 degrees about its longitudinal axis.

Referring now FIGS. 32*a*–32*b*, there is illustrated an implant holder 650. Implant holder 650 includes a shaft 652 extending between a proximal 654 and a distal end 656. Shaft 652 includes a threaded portion 664 adjacent proximal end 654. Distal end 656 includes an implant engaging portion having a pair of fingers 658 extending from an end section 668. A shoulder 666 is provided between a tapered section 662 and end section 668. Projections 672 extend distally from a distal end wall of end section 668. A slit 670 extends between the projections 672 proximally along the center axis C of implant holder 650 for a distance d, biasing implant holder 650 to a position that is disengaged with the implant. Flats 674 are provided adjacent the proximal end of shaft 652 to provide an indication of the orientation of fingers 658.

Figure 33:
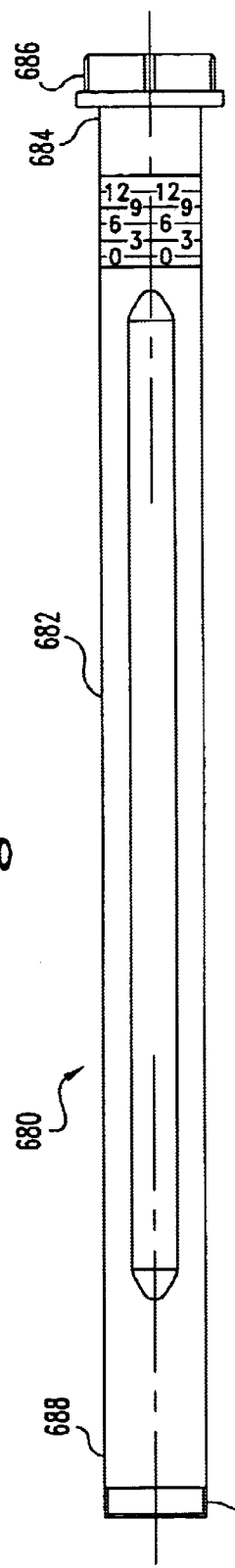
Figure 34:
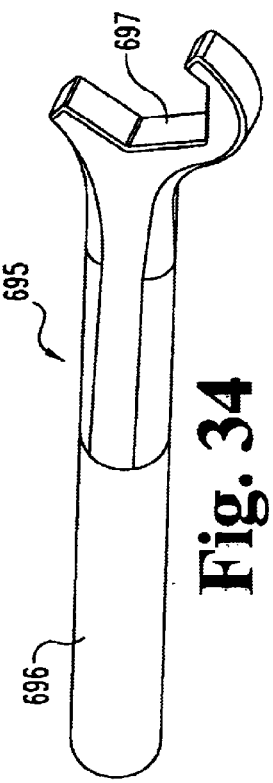
FIG. 34 is a perspective view of a wrench usable with the outer sleeve and implant holder shaft of FIGS. 33 and 32a, respectively.

Referring now to FIG. 33, an implant driver sleeve 680 is provided. Driver sleeve 680 includes a cylindrical member 682 having a hollow interior sized to receive implant holder 650 therethrough. Cylindrical member 682 includes threads (not shown) formed in its hollow interior configured to mate with threads 664 on implant holder 650. Cylindrical member 682 has a proximal end 684 with a hex nut 686 secured thereto. Cylindrical member 682 further includes a distal end 688 having a bushing 690 secured thereto. It is preferred that bushing 690 is made from a lubricious plastic material such as DELRIN and is press fit onto distal end 688. In FIG. 34, a wrench 695 is provided with a handle 696 and an open-sided hex driving head 697 sized to engage hex nut 686 of implant driver sleeve 680. Implant holder 650 has a sufficient length such that distal end 656 extends distally from distal end 688 of driver sleeve 680, and proximal end 654 of implant holder 650 extends proximally from proximal end 684 of driver sleeve 680.

Figure 43B:
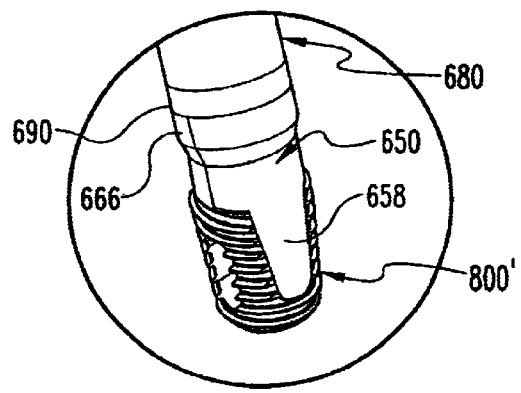
FIGS. 43a–43b illustrate securement of an implant to the implant holder of FIG. 32a using the driver sleeve.
Figure 43A:
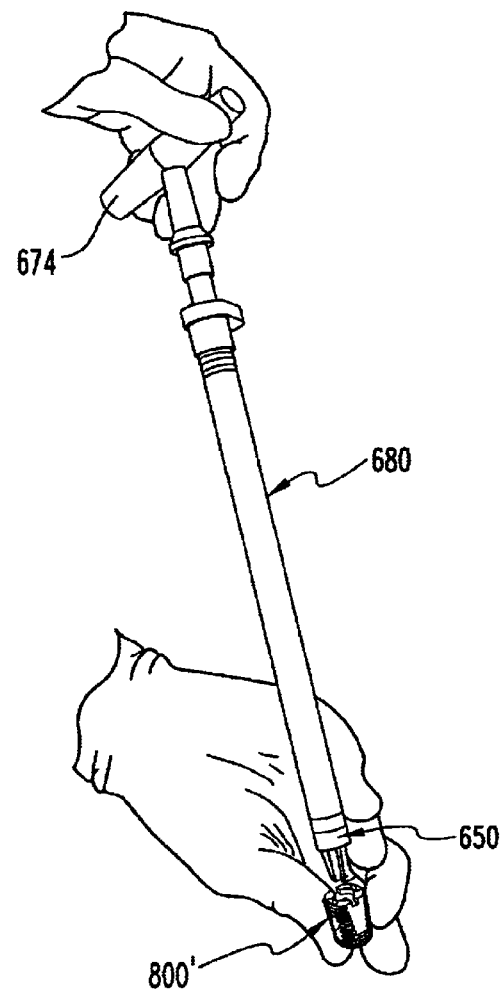

To secure an implant 800 to implant holder 650 as shown in FIGS. 43*a*–43*b*, implant holder 650 is placed through driver sleeve 680 and secured thereto by partially mating the proximal end of threads 664 onto the distal end of the inner thread of cylindrical member 682. A T-handle 674 is secured to a connector at proximal end 654 of implant holder 650. Implant 800 is held in position by a vise and the implant can be pre-packed with bone growth material through a proximal end opening of the implant. Implant holder 650 is then positioned with fingers 658 around implant 800, and projections 672 can be received in the end opening of the implant. Preferably, fingers 658 are configured to mate with flats or other surfaces provided on the sidewalls of implant 800. Implant holder 650 is threaded proximally with respect to driver sleeve 680 so that bushing 690 contacts tapered portion 662, and tapered portion 662 is pulled proximally into the distal end opening of driver sleeve 680. Implant holder 650 can be held to prevent its rotation with handle 674 while driver sleeve 650 is rotated with wrench 695. The force exerted on tapered portion 662 of implant holder 650 moves implant holder 650 to an engaged position with the implant 800 by causing slit 670 to narrow and fingers 658 to be pushed towards one another to firmly grip implant 800 therebetween. Plastic bushing 690 prevents jamming of implant holder 650 with driver sleeve 680, and also facilitates disassembly of outer sleeve 680 from implant holder 650 to release implant 800 after implant 800 is inserted in the disc space.

Figure 44A:
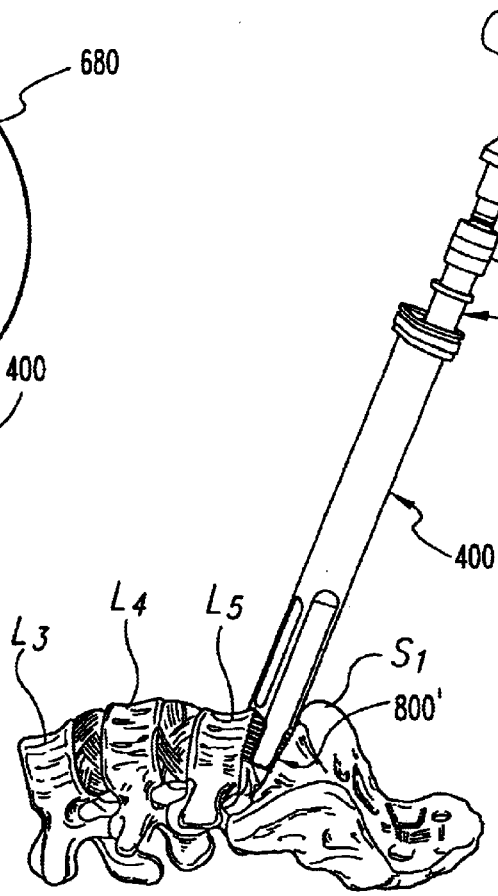
FIGS. 44a–44c illustrate insertion of the implant into the second implant insertion location in the disc space through the guide sleeve.
Figure 44B:
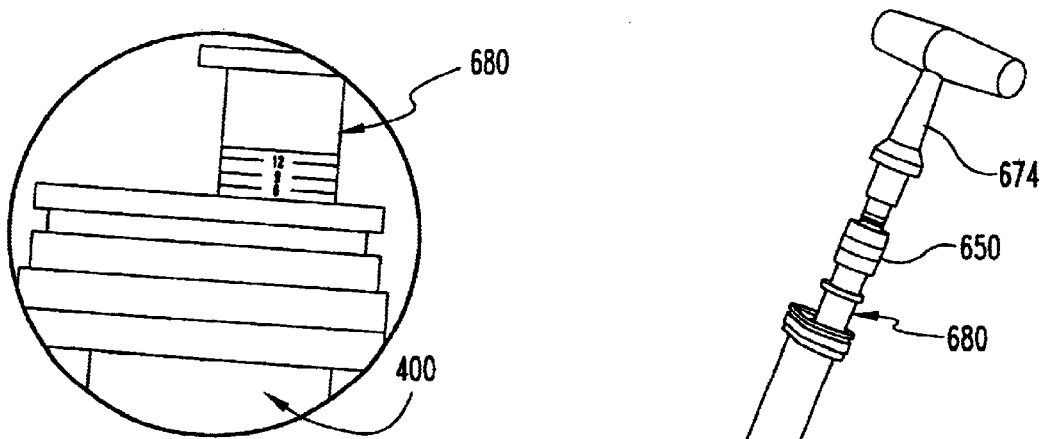
Figure 44C:
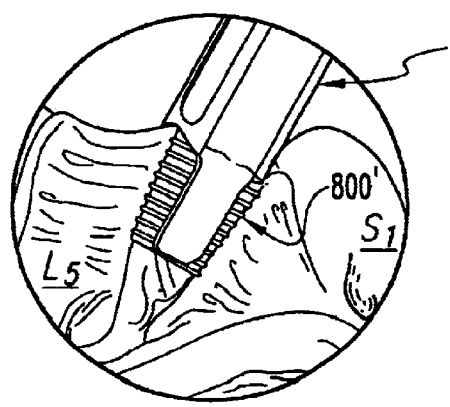
Figure 45:
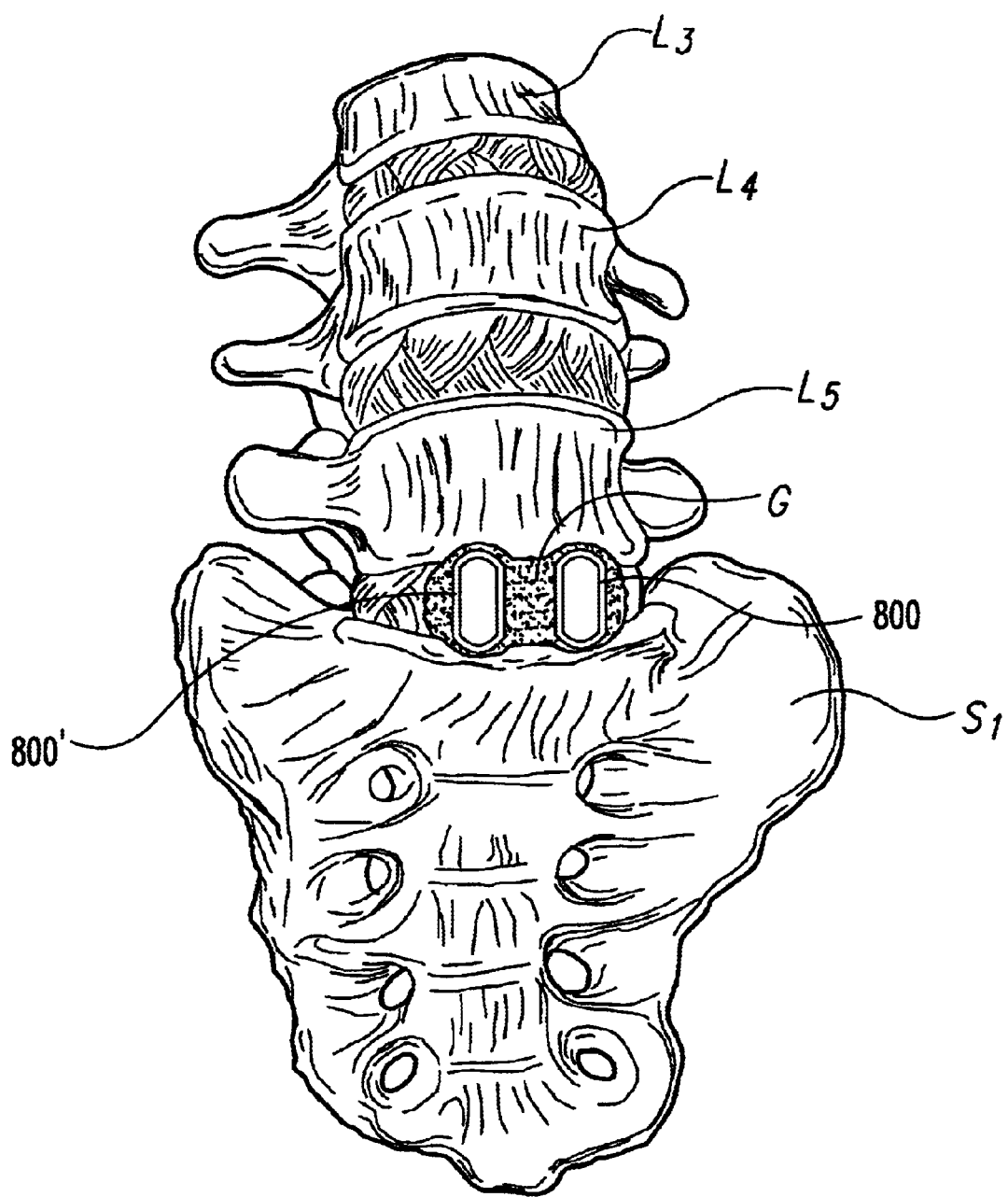
FIG. 45 illustrates implants inserted into the disc space at the first implant location and the second implant location.

Referring now to FIGS. 35*a* to 45, an example of a preferred surgical technique employing the instruments of FIGS. 23*a*–34 in an anterior approach to the spine to insert a first implant 800 and a second implant 800' bi-laterally in the disc space (as shown in FIG. 45) will now be described. It will be understood however, that the instruments of FIGS. 23*a*–34 can also have application in other approaches to the spine and with other types of implants mentioned herein.

Figure 35A:
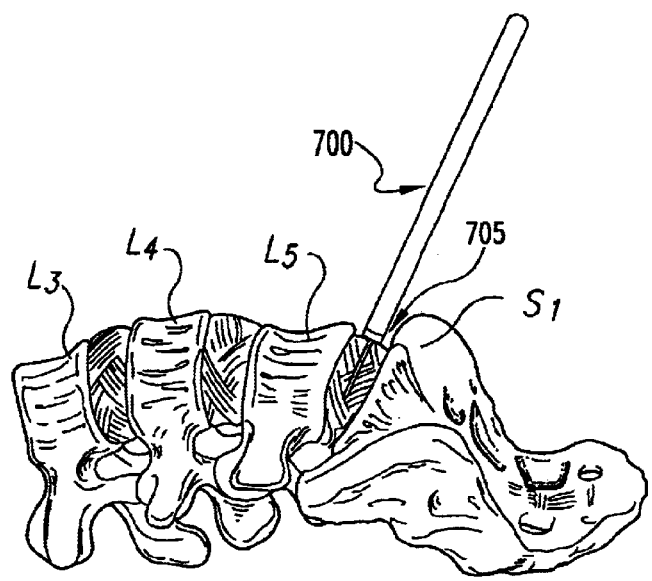
FIGS. 35a–35c illustrate various steps in locating and marking the midline of the disc space at a subject vertebral level.
Figure 35B:
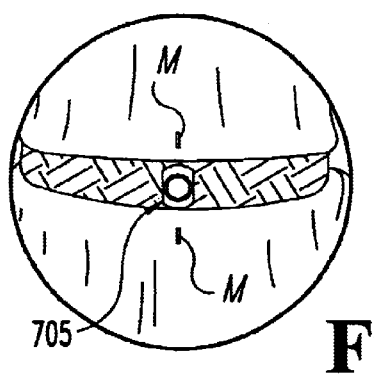
Figure 35C:
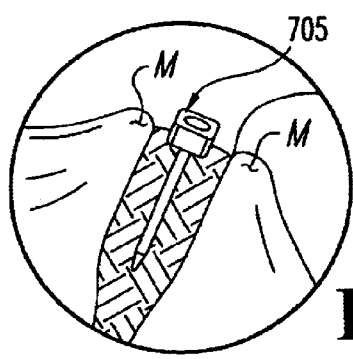

Referring now to FIGS. 35*a*–35*c*, the disc space between the L5 and S1 level of the spine has been accessed through an anterior exposure. The middle sacral artery is typically ligated and divided with this approach. It is also contemplated that the L4–L5 level of the spine could be accessed with the iliolumbar and segmental vessels identified and ligated if necessary. The center of the disc space is identified and marked with a template shaft 700 and centering pin 705. Accurate identification of the midline can be made with the assistance of anterior/posterior and lateral fluoroscopy. Marks M are made at the midline both cephalad and caudal to centering pin 705 on the vertebral bodies.

Figure 36A:
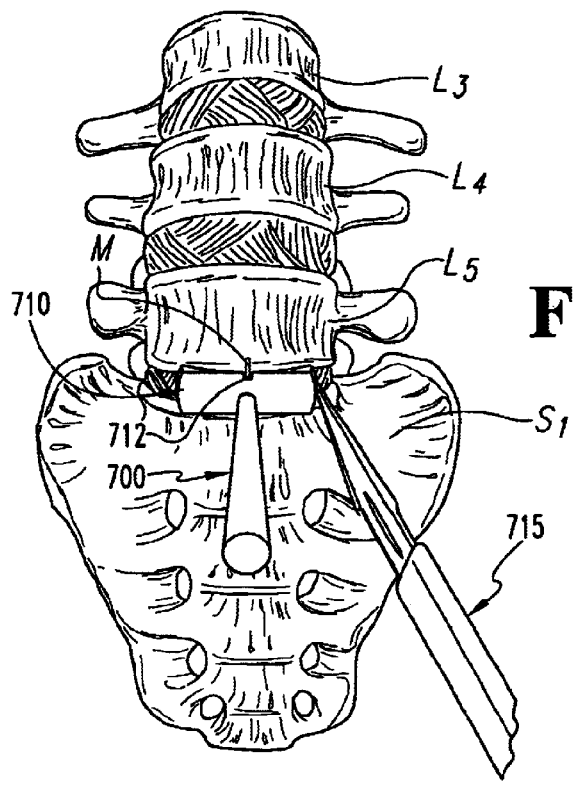
FIGS. 36a–36c illustrate various steps in performing a discectomy at the subject vertebral level.
Figure 36B:
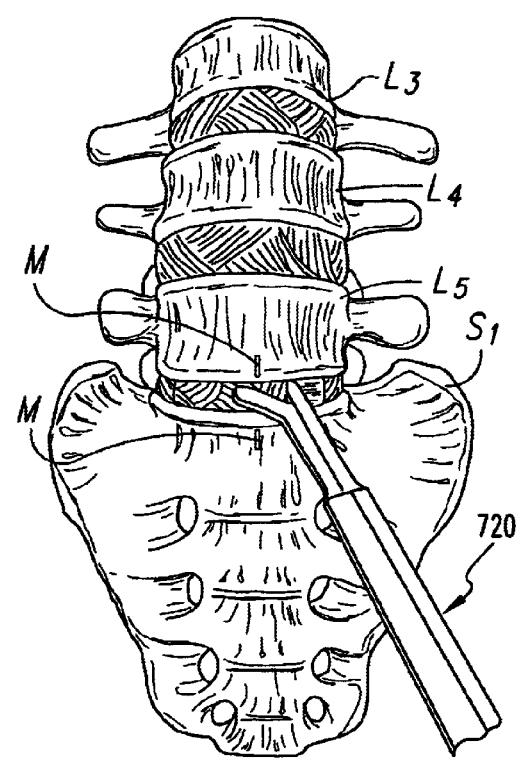
Figure 36C:
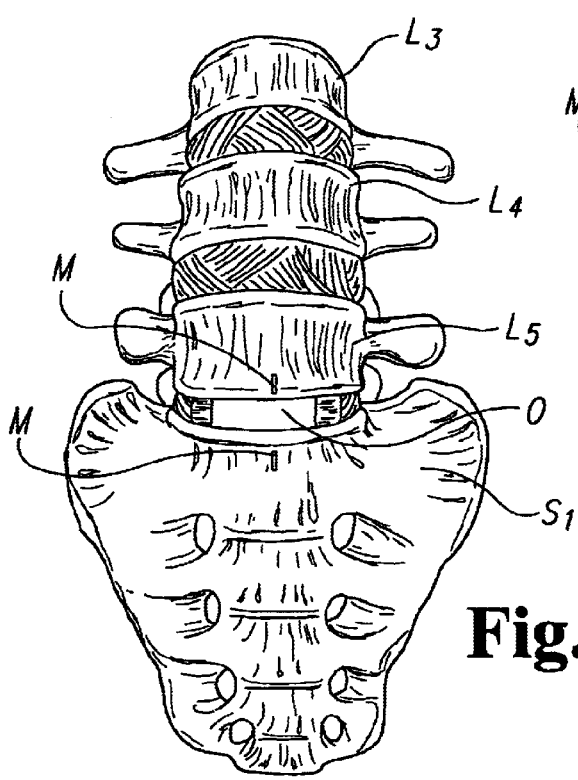

The centering pin 705 is then removed, and as shown in FIG. 36*a* an appropriate sized template 710 is attached to shaft 700 and positioned so that notch 712 aligns with marks M. The lateral margins of the block discectomy are marked by sharply incising the annulus with cutting instrument 715. As shown in FIG. 36*b* and 36*c*, template 710 is removed and an en bloc discectomy is typically performed to create an opening O that provides adequate space for insertion of distractors 350, 380. A disc material removal instrument 720, such as a pituitary rongeur, can be used to remove the nucleus pulposous to provide room in the disc space for the distractors and the implants 800. The anterior osteophytes on the vertebral bodies can also be removed to ensure accurate seating of the distal end of guide sleeve 400 against the vertebral bodies. Curettes can be used to remove the cartilaginous endplates. The discectomy is performed under direct vision, and lateral fluoroscopy can be used to confirm the extent of disc removal in the posterior portion of the disc space. The lateral margins of the discectomy should not be exceeded so that the anterolateral annulus remains intact to enhance the stability of the construct.

If necessary, sequential distraction of the disc space can be carried out using starter distractor set 725 as shown in FIG. 37. Starter distractor set 725 includes a number of distractor tips of increasing height 726*a*, 726*b*, 726*c*, 726*d* attachable to distractor handle 728. If necessary, the distractor tips are sequentially driven into the disc space to develop the disc space height prior to insertion of distractor assembly 450.

Referring now to FIG. 38, distractor assembly 450 is then assembled with distractor driver cap 550 as discussed above. The distractor tips of distractors 350, 380 are then inserted into opening O with care taken to ensure distractor assembly 450 is placed at midline M. Distractor driver cap 550 is then impacted until the distractor tips are fully seated in the disc space. The radiographic markers in the tips can be used to verify positioning during seating. Distractor assembly 450 should remain parallel to the endplates during seating, and the intact anterolateral annulus will act to center the distractor assembly 450 and resist lateral migration during impaction. The distractor driver cap 550 is then removed to de-couple distractors 350, 380 from guide sleeve 400.

Figure 40A:
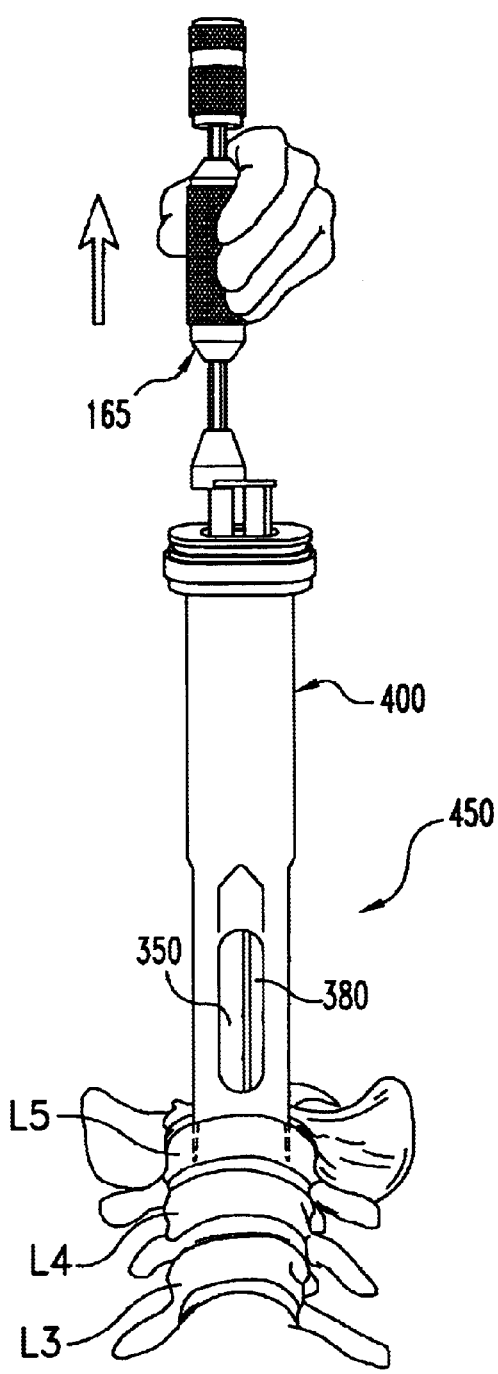
FIGS. 40a–40c illustrate removal of a first distractor from the guide sleeve after insertion of the distractor/guide sleeve assembly into the disc space.
Figure 40B:
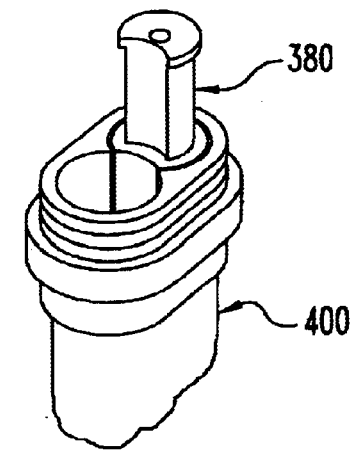
Figure 40C:
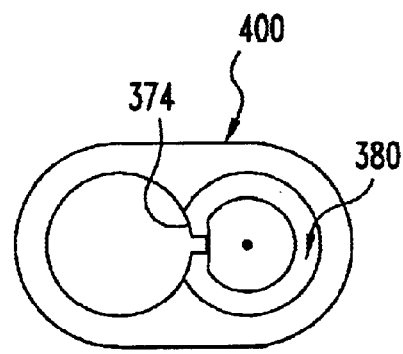

Referring now to FIG. 39, an impactor cap 730 is secured to guide sleeve 400 and the guide sleeve 400 is impacted until flanges 418 and 420 are fully seated in the disc space and the distal end of sleeve 400 is positioned against the vertebral bodies while distractors 350, 380 remain as positioned in the disc space with distractor driver cap 550. Impactor cap 730 is then removed. As shown in FIG. 40*a*, an instrument remover such as slap hammer 165 is secured to first distractor 350. First distractor 350 is then removed, and a cylindrical working channel is provided through guide sleeve 400 to the disc space along the recessed area defined by concave surface 394 of second distractor 380 as shown in FIGS. 40*b* and 40*c*.

Figure 41B:
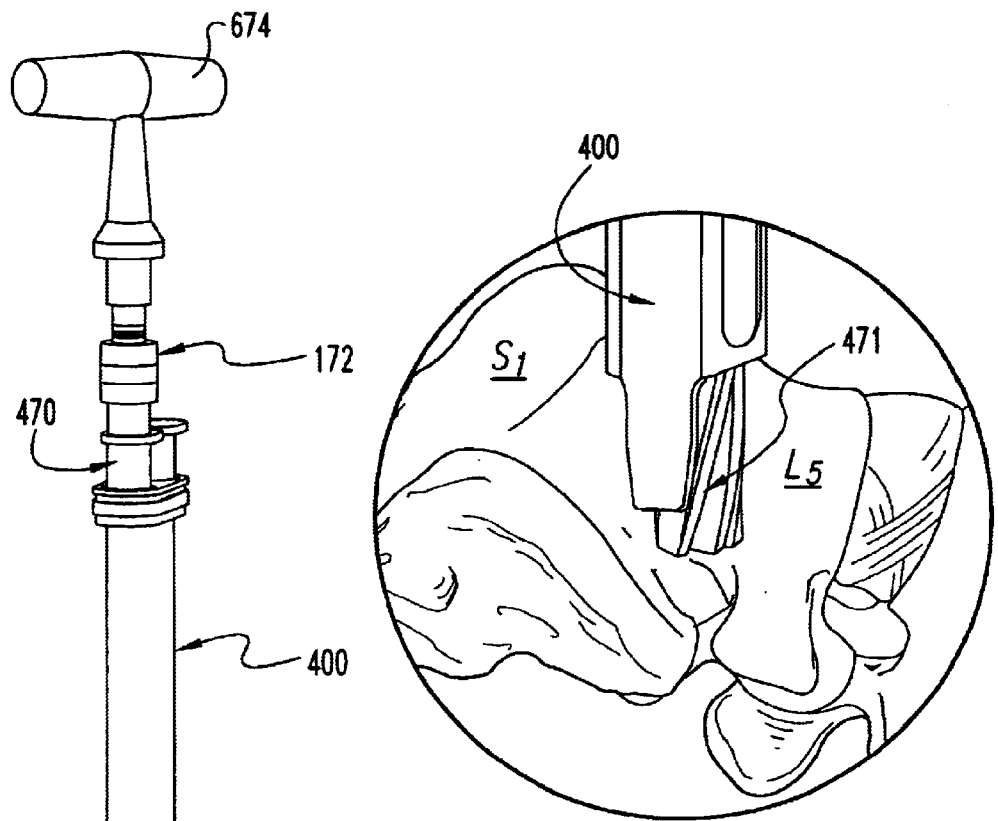
FIGS. 41a–41b illustrate reaming a first implant insertion location in the disc space through the guide sleeve.
Figure 41A:
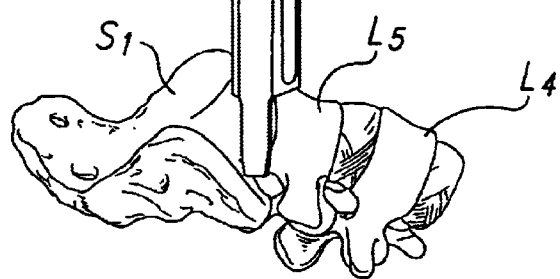

Referring now to FIGS. 41*a* and 41*b*, reamer 470 is positioned in the working channel to ream a cylindrical hole in the disc space at a first disc space location to prepare it for insertion of implant 800. Preferably, the reamer 470 creates a hole that is sized to correspond to the height of the leading end of the implant to be inserted into the disc space. Reamer 470 is attached to a depth stop, such as the depth stop 172 discussed above, and T-handle 674. The appropriate depth stop setting is selected based on preoperative templating using axial CT or MR images, and should reflect the length of implant 800 and the desired countersink of implant 800 in the disc space. The depth of reaming in the disc space can be verified with fluoroscopy.

Figures 42A, 42B:
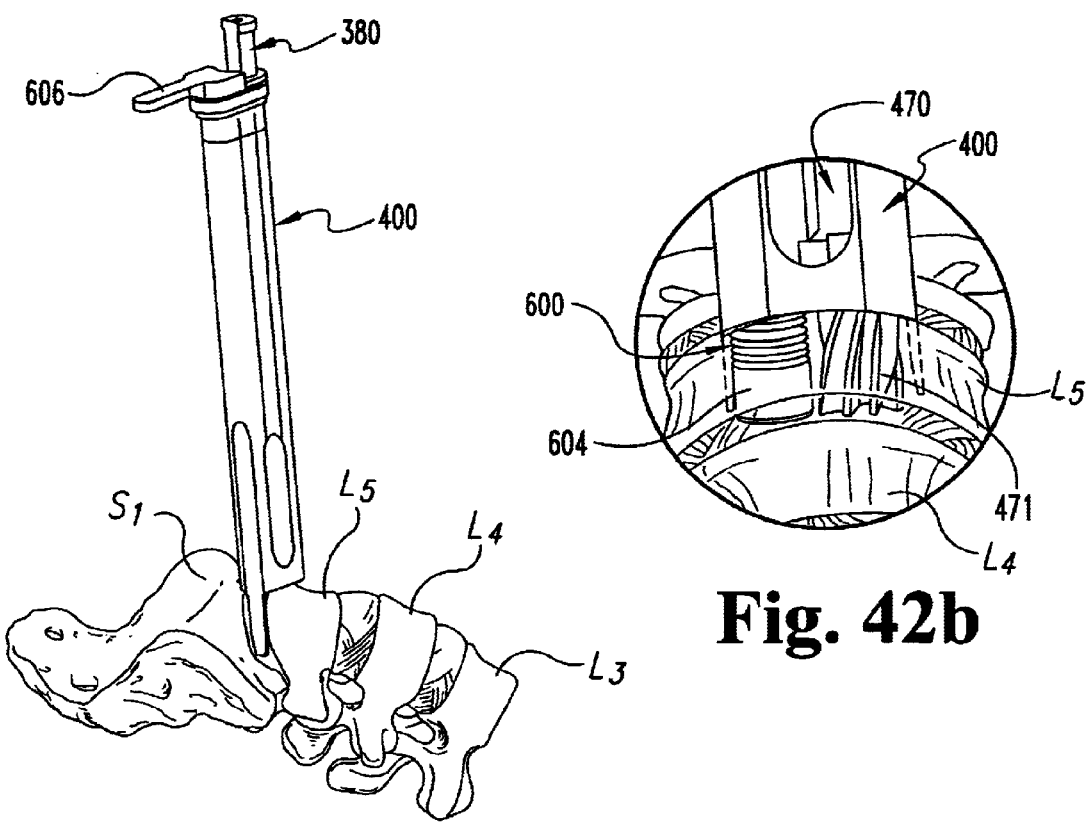
FIGS. 42a–42b illustrate insertion of a reamer plug in the reamed first implant insertion location and reaming a second implant insertion location in the disc space through the guide sleeve.

Referring now to FIG. 42*a* reaming plug 600 is inserted into the reamed first disc space location created with reamer 470. First implant 800 is preferably not inserted into the first disc space location after the first disc space location is reamed. The tapered first implant 800 acts to distract the disc space to establish the lordotic angle between the endplates. Reaming of the second disc space location could be problematic if first implant 800 was inserted into the first disc space location before the second disc space location is reamed. Thus reamer plug 600 maintains the disc space distraction while distractor 380 is removed. Reamer 470 is then used to ream a second disc space location adjacent the first disc space location for insertion of second implant 800'. Plug 604 is sized such that sufficient space exists in the disc space for cutting head 471 to rotate with the shaft of reamer 470 positioned along concave surface of shaft 602. Handle 606 engages the proximal end of sleeve 400 to clock shaft 602 against the inner side of the wall of guide sleeve 400 to keep reamer plug 600 from interfering with reamer 470 and also from interfering with insertion of second implant 800'.

As discussed above, second implant 800' is engaged to an implant inserter by engaging the implant holder 650 to implant 800' with driver sleeve 680 as shown in FIGS. 43*a* and 43*b*. As shown in FIGS. 44*a*–44*c*, second implant 800' is threaded into the second disc space location with reamer plug 600 inserted at the first disc space location. Second implant 800' preferably includes self-tapping threads, and is tapered to establish the desired lordotic angle between the endplates. After second implant 800' is inserted into the second disc space location, implant holder 650 and driver sleeve 680 are removed. Reamer plug 600 is withdrawn from the first disc space location, and first implant 800 is inserted into the first disc space location as shown in FIG. 45 with the implant inserter. When inserted, implants 800, 800' preferably are countersunk 2 to 5 millimeters from the anterior face of the vertebral bodies. If necessary, implant adjuster 620 can be inserted into the proximal end opening of the implants 800, 800' for alignment corrections. Bone growth G material can be placed around the implants 800, 800' in the disc space to facilitate fusion.

While the use of threaded implants has been primarily discussed for use with the instruments of the present invention, the present invention likewise contemplates using push-in type implants and/or expandable implants in the disc space with the instruments described herein. Also, while it is preferred that the present invention be utilized for insertion of two implants at bilateral locations within the disc space, insertion of a single implant into the disc space is also contemplated.

Of course, the present invention makes use of depth stops and other devices for measuring and controlling the depth of the various procedures performed in the disc space. These devices and procedures are more fully explained in the Danek brochure and in the '917 patent application. Additionally, the present invention is not limited to use with the tools and instruments described above, and guide sleeve 100 and distractors 50, 80 may be used with other such devices as would normally occur to those skilled in the art to which the invention relates.

Distractor tips according to another aspect of the present invention will be described with reference to FIGS. 46–56. The distractor tip of FIGS. 46–56 has application with side-by-side cylindrical distractor shafts, with side-by-side reduced profile distractors, with first and second distractors spaced from one another, or with a single distractor inserted in isolation in the disc space. Referring now to FIGS. 46–52, distractor tip 900 is configured to generally correspond to the anatomical geometry of the vertebral endplates E1 and E2, and, in particular, the endplate curvatures C1, C2 and C3, as will be described further below. Distractor tip 900 is self-locating in the spinal disc space to the location where its geometrical configuration most closely matches that of the vertebral endplates, and any tendency for distractor tip 900 to move after it is positioned in the disc space is thus reduced. Distractor tip 900 can also be provided with teeth to further resist movement of distractor tip 900 after it is inserted in the disc space.

Figure 54:
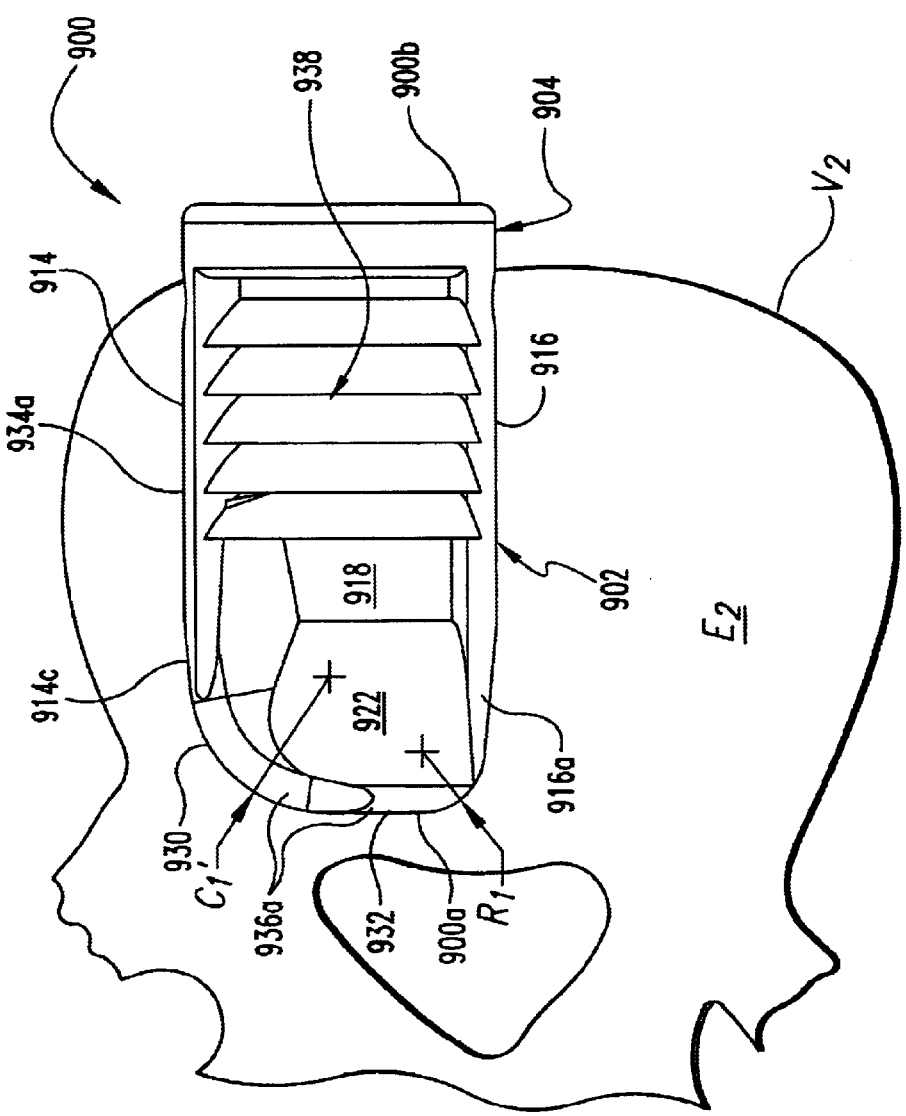
FIG. 54 is an axial view of a spinal disc space with the distractor tip of FIG. 46 positioned therein.
Figure 55:
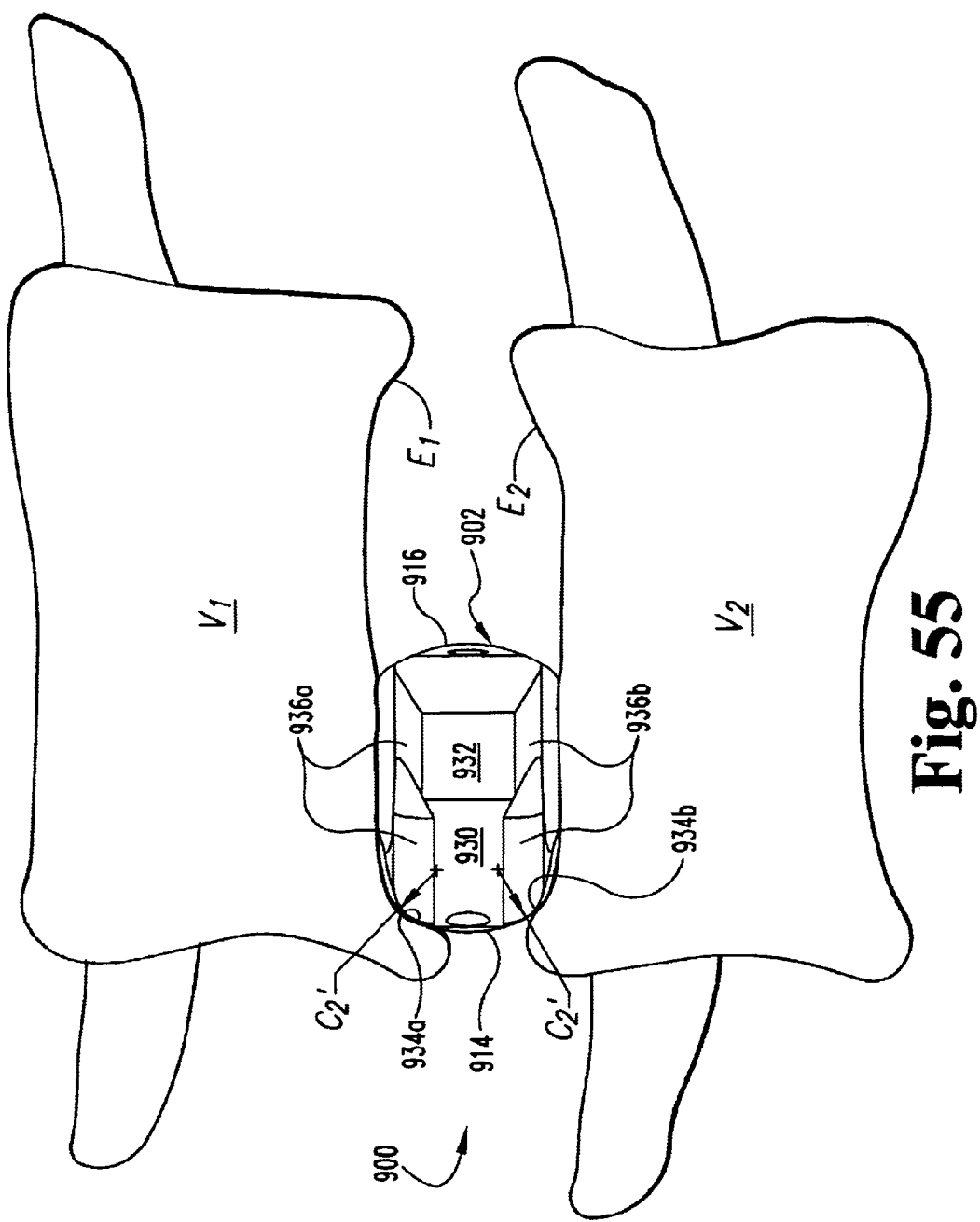
FIG. 55 is an elevational view looking in the anterior to posterior direction of a spinal disc space with the distractor tip of FIG. 46 positioned therein.
Figure 56:
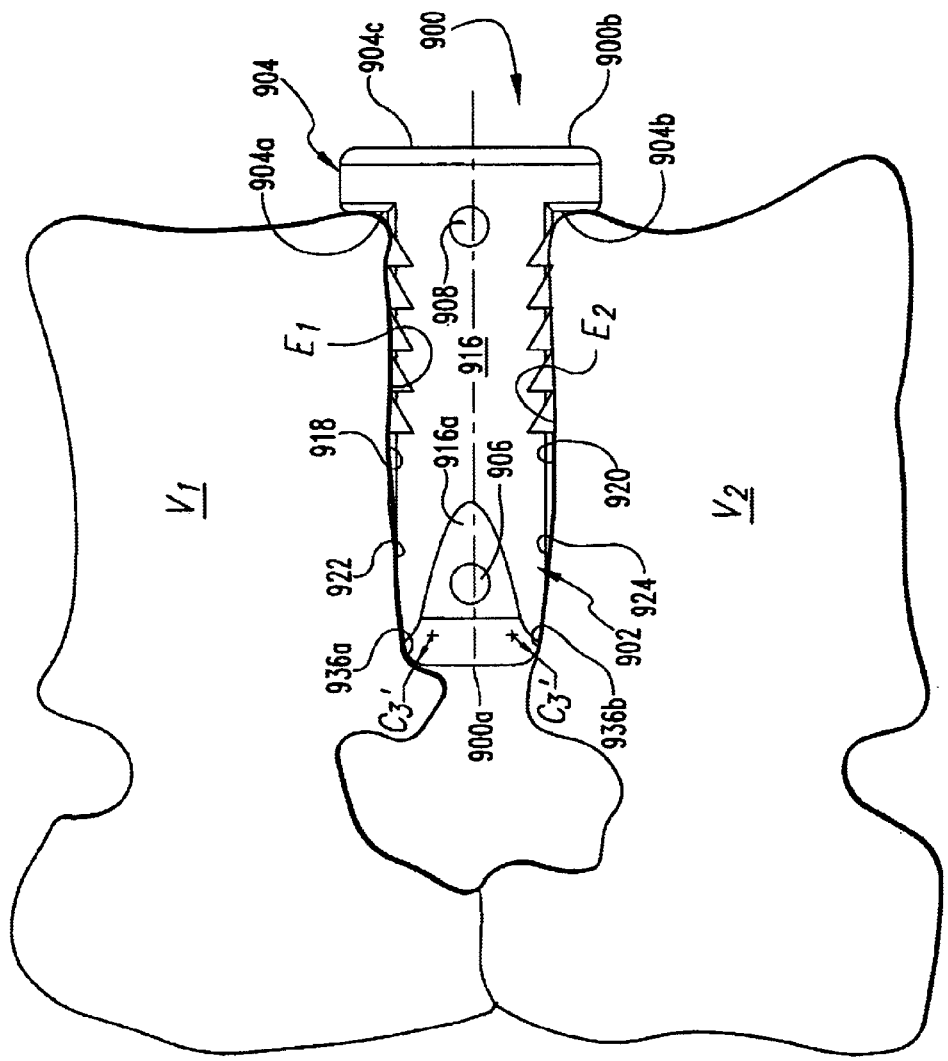
FIG. 56 is an elevational view looking in the medial to lateral direction of a spinal disc space with the distractor tip of FIG. 46 positioned therein.

Distractor tip 900 includes a body 902 positionable in the spinal disc space between adjacent vertebrae V1, V2 as shown in FIGS. 54–56. Distractor tip 900 can also be provided with an end wall 904 which extends from body 902 in the cephalad and caudal directions. End wall 904 has inner wall surfaces 904a, 904b oriented toward body 902 which can contact the vertebrae V1, V2, respectively, outside the disc space to limit the insertion depth of body 904 into the disc space as shown in FIG. 56. End wall 904 has a proximal face 904c opposite inner surfaces 904a, 904b. A bore 910 is provided in distractor tip 900 extending distally from proximal face 904c. Bore 910 can be threaded or otherwise configured to allow distractor tip 900 to be coupled to a distractor shaft. Removable distractor tips provide modularity so that various sized tips can be used with a single shaft. Such tips can also be color-coded so that the appropriately sized tip can be readily selected along with the other color-coded surgical instruments and implants to be used in procedures employing that particular tip. It is also contemplated that distractor tip 900 can be provided without end wall 904, and a distractor shaft is coupled directly to body 902. It is further contemplated that distractor tip 900 could be integrally formed with a distractor shaft as a single unit.

Distractor tip 900 can be provided with distal radiographic marker 906 and one or more proximal radiographic markers 908. Radiographic markers 906, 908 can be in the form of stainless steel pins, balls, or other radiographic material. In the illustrated embodiment, two such proximal markers 908 are provided on either side of bore 910. Radiographic markers can be located in a horizontal plane defined by central axis 912 so that the markers are located in the vertical center of the disc space when distractor tip 900 is inserted therein. Distractor tip 900 can thus be made from aluminum or other radiolucent material, and markers 906, 908 allow the surgeon to determine the location of and monitor insertion of distractor tip 900 during insertion into the disc space. Also, the surgeon can radiographically or monitor an implant or instruments located beside distractor tip 900 without interference from distractor tip 900.

Distractor tip 900 has central axis 912 extending therethrough between a leading distal end 900a of distractor tip 900 and an opposite trailing proximal end 900b. As used herein, distal refers to a position located away from the surgeon as distractor tip 900 is inserted into the disc space and proximal refers to the direction oriented towards the surgeon as distractor tip 900 is inserted in the disc space. Central axis 912 is centrally located between a lateral surface 914 and a medial surface 916 of distractor tip 900. Lateral surface 914 is positioned adjacent to or toward the lateral edges of the vertebral endplates when distractor tip 900 is inserted in the disc space. Medial surface 916 is located adjacent to or on the central spinal column axis extending through the middle of the vertebral endplate when distractor tip 900 is inserted in the disc space.

Distractor tip 900 further includes a proximal upper surface 918 and a proximal lower surface 920. Each of the proximal surfaces 918, 920 extend distally from end wall 904 toward distal end 900a to an upper distal surface 922 and a lower distal surface 924, respectively. In the illustrated embodiment, proximal surfaces 918, 920 extend parallel to central axis 912. The proximal upper and lower surfaces can include a number of teeth 938, 940, respectively, formed thereacross between lateral surface 914 and medial surface 916. Teeth 938, 940 can be formed by cutting grooves in the upper and lower proximal surfaces 918, 920. In the illustrated embodiment, teeth 938, 940 each have a sloped distal wall and a vertical trailing wall that join at a sharp peek. The sloped distal walls facilitate insertion, while the teeth and vertical proximal wall resist pullout and twisting of distractor tip 900 in the disc space and provide solid anchorage with respect to the vertebral endplates. Distal upper and lower surfaces 922, 924 are tapered toward central axis 912 from their junction with respective adjacent proximal upper and lower surfaces so that distractor tip 900 has a reduced height 926 at distal end 900a that is less than a height 928 at proximal upper and lower surfaces 918, 920.

Figure 51:
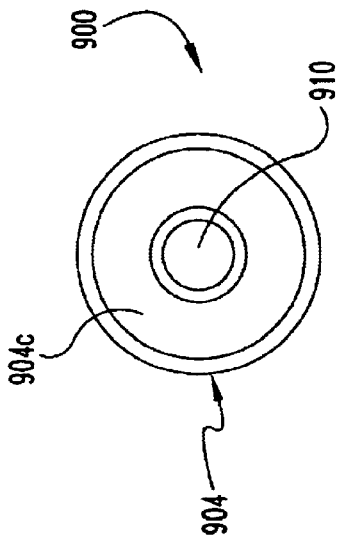
FIG. 51 is a cross-sectional view through line 51—51 of FIG. 50.

In the illustrated embodiment of FIG. 51, medial surface 916 has a convexly arcuate profile between upper proximal surface 918 and lower proximal surface 920. Other profile shapes are also contemplated, including a linear medial surface or a concave medial surface. Distal end 900a includes a generally linear distal end surface 932 that extends generally transverse to central axis 912. Lateral surface 914 is described further below.

Figure 53C:
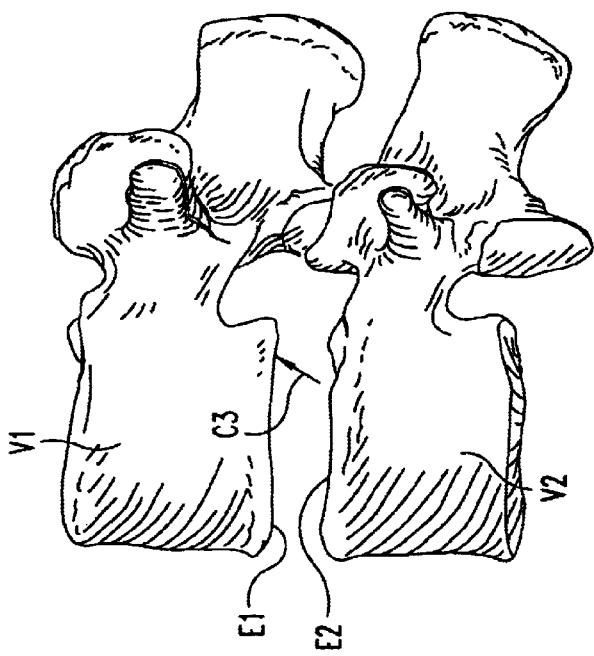
FIGS. 53a–53c illustrate an axial view, an anterior-posterior view, and a lateral view of a pair of vertebral bodies and the spinal disc space therebetween.
Figure 53B:
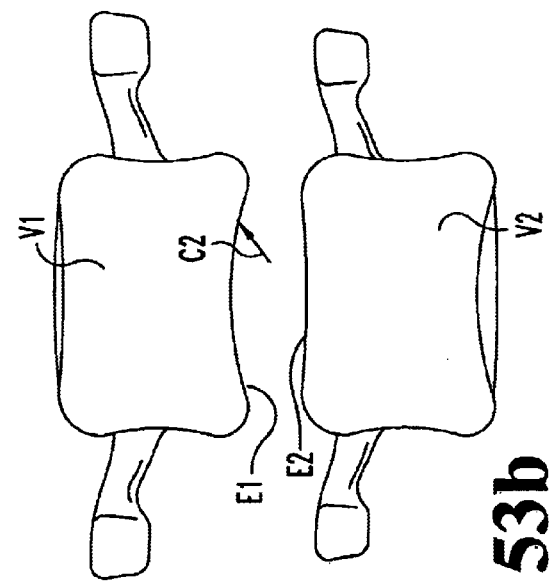
Figure 53A:
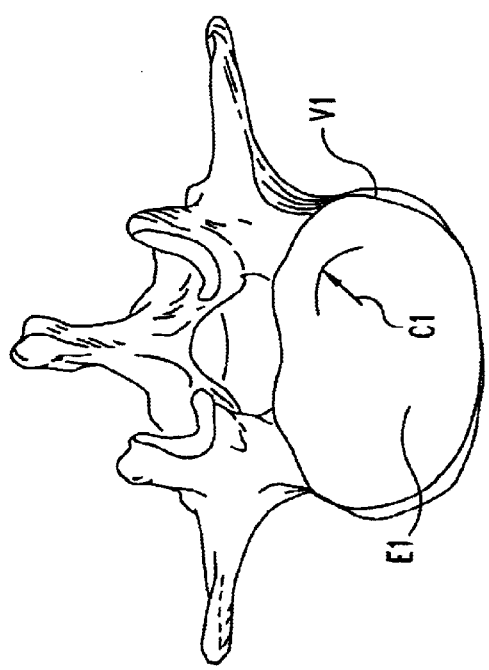

With reference to FIGS. 53a–53c, the vertebral endplate anatomical geometry will be discussed with reference to vertebrae V1 and V2 positioned on opposite sides of a disc space D. It is contemplated that vertebrae V1, V2 form part of the lumbar or sacral region of the spine; however, the principles of the present invention also have application in the cervical and thoracic regions of the spine. Vertebra V1 has an endplate E1 and vertebra V2 has an endplate E2. Endplate E1 has a cortical rim around its perimeter that surrounds a concave portion of cancellous or thin cortical bone in the middle of endplate E1. When distractor tip 900 is used in an anterior approach to the spine, distal end surface 932 is located in the posterior region of endplates E1 and E2 with distractor tip 900 inserted into the disc space.

The junction of the cortical rim and concave portion of the endplate defines a curvature C1 in the axial plane between the lateral portion of the cortical rim and the posterior portion of the cortical rim. In the coronal plane of FIG. 53b, endplate E1 has an inner cortical rim curvature C2 at the junction between the concave portion and the cortical rim. In the sagittal plane of FIG. 53c, the inner cortical rim of endplate E1 has a curvature C3 at the junction between the concave portion and the cortical rim along the posterior portion of the cortical rim. End plate E2 has inner cortical rim at the junctions between its concave portion and cortical rim defining similar curvatures.

Figure 47:
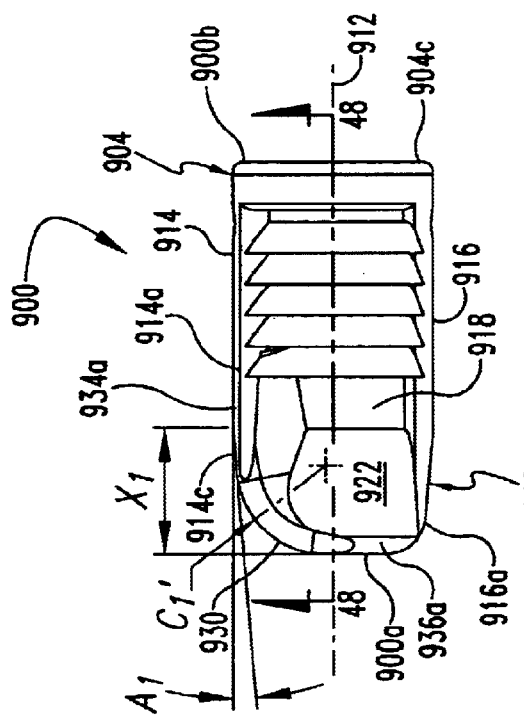
FIG. 47 is a plan view of the distractor tip of FIG. 46.
Figure 46:
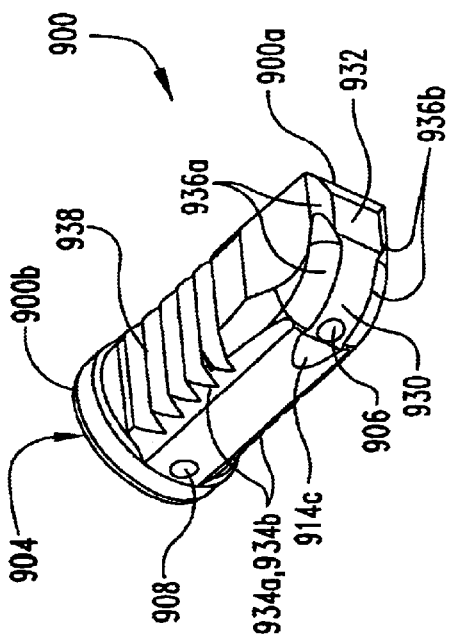
FIG. 46 is a perspective view of a distractor tip according to another aspect of the present invention.

As shown in FIG. 47 and FIG. 54, body 902 includes a first transition surface 930 between distal end surface 932 and lateral surface 914 having a configuration that takes into account the vertebral endplate anatomy. First transition surface 930 has a curvature C1' in the axial plane that generally conforms to curvature C1 in the axial plane of the inner cortical rim where it transitions between the lateral portion of the cortical rim and the posterior portion of the cortical rim. In one specific embodiment, curvature C1' is defined by a radius of curvature of 9 millimeters.

Lateral surface 914 has a proximal portion 914a extending generally parallel with central axis 912. At a distance X1 from distal end surface 932, lateral surface 914 bends at an angle A1 from proximal portion 914a towards central axis 912 to form a tapered portion 914c that blends into the curved transition surface 930. In one specific embodiment, this distance X is 10 millimeters and angle A1 is 10 degrees. Medial surface 916 can be similarly configured with a taper angle A1 to form a tapered portion 916a. Medial tapered surface 916a extends further distally than lateral tapered surface 914c, and blends into distal end surface 932 by radius R1. Tapered surfaces 914c and 916a provide an overall reduced width at distal end 900a.

As shown in FIG. 51, lateral surface 914 has a generally linear central region 914b. Extending from this central region between the upper and lower proximal surfaces 918, 920 and the upper and lower distal surfaces 922, 924 are upper and lower second transition surfaces 934a, 934b, respectively. Second transition surfaces 934a, 934b each have a curvature C2' that conforms to the inner cortical rim along the lateral portion thereof in the coronal plane, such as shown in FIG. 55. Second transition surfaces 934a, 934b have a height X2 from the respective upper or lower proximal surfaces to the central region 914b. In one specific embodiment, height X2 is 3 millimeters, and curvature C2' is defined by a radius of curvature of 8 millimeters.

Figure 48:
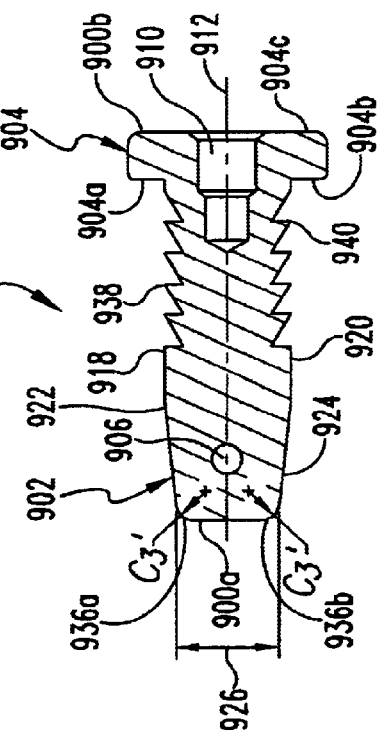
FIG. 48 is a cross-sectional view through line 48—48 of FIG. 47.
Figure 52:
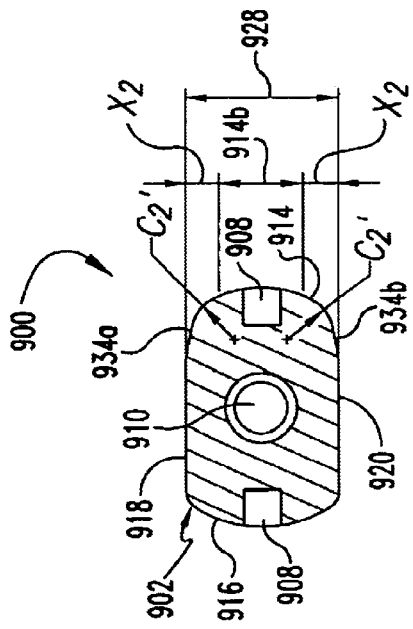
FIG. 52 is an elevational view of the proximal end of the distractor tip of FIG. 46.
Figure 49:
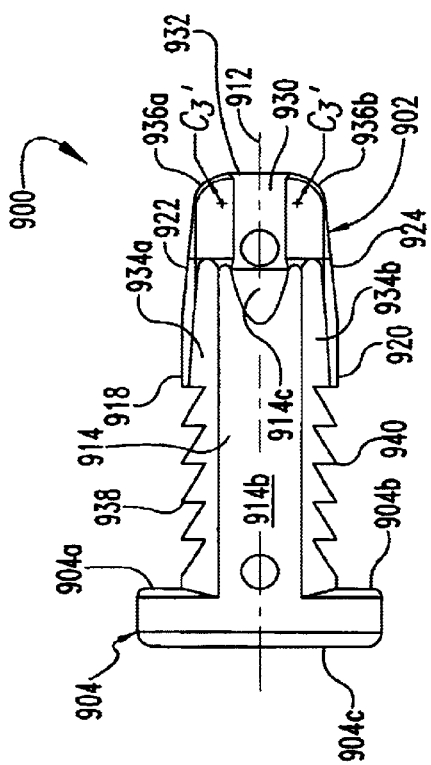
FIG. 49 is an elevational view of the lateral side of the distractor tip of FIG. 46.
Figure 50:
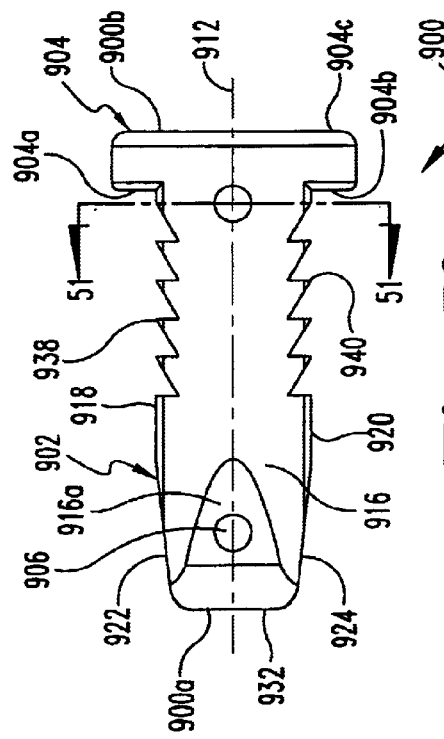
FIG. 50 is an elevational view of the medial side of the distractor tip of FIG. 46.

As shown in FIGS. 48–49, upper and lower third transition surfaces 936a, 936b extend from distal end surface 932 to distal upper surface 922 and distal lower surface 924. Upper and lower third transition surfaces 936a, 936b also extend from first transition surface 930 to the respective upper and lower distal surfaces 922, 924. Third transition surfaces 936a, 936b have a curvature C3' that blends distal end surface 932 into the upper and lower distal surfaces 922, 924. As shown in FIG. 56, curvature C3' of third transition surfaces 936a, 936b conforms to the inner cortical rim along the posterior portion of the cortical rim and its transition to the lateral portion of the cortical rim. Third transition surfaces 936a, 936b further blend first transition surface 930 into the upper and lower distal surfaces 922, 924. In one specific embodiment, curvature C3' is defined by a radius of curvature of 1.5 millimeters along distal end surface 932 and a radius of curvature of 2 millimeters along first transition surface 930.

Distractor tip 900 having the above features generally corresponds to the anatomical geometry of the vertebral endplates E1 and E2, and, in particular, the endplate curvatures C1, C2 and C3. As such, distractor tip 900 is self-locating in the spinal disc space to the location where its geometrical configuration most closely matches that of the vertebral endplates. Furthermore, upon insertion distractor tip 900 will be located in the disc space in contact with the inner cortical rim, and any tendency for distractor tip 900 to move laterally or distally in the disc space is resisted by contact between the cortical rim and body 904.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A spinal disc space distractor, comprising:
   a body positionable in a spinal disc space between adjacent vertebrae, said body having a distal end surface, a proximal end and a central axis extending therebetween, said body including:
      a lateral surface extending generally in the direction of said central axis;
      a medial surface opposite said lateral surface and extending generally in the direction of said central axis;
      an upper surface extending generally in the direction of said central axis;
      a lower surface opposite said upper surface and extending generally in the direction of said central axis;
      a first transition surface extending between said distal end surface and said lateral surface, said first transition surface having a first curvature generally corresponding to a curvature of an inner portion of a cortical rim of vertebral endplates in an axial plane;
      a second upper transition surface extending between said lateral surface and said upper surface and a second lower transition surface extending between said lateral surface and said lower surface, said second upper and lower transition surfaces each having a second curvature generally corresponding to a curvature of an inner portion of a cortical rim of vertebral endplates in a coronal plane; and
      a third upper transition surface extending between said distal end surface and said upper surface and a third lower transition surface extending between said distal end surface and said lower surface, said third upper and lower transition surfaces each having a third curvature generally corresponding to a curvature of an inner portion of a cortical rim of vertebral endplates in a sagittal plane.

2. The distractor of claim 1, wherein said third upper transition surface extends between said first transition surface and said upper surface and said third lower transition surface extends between said first transition surface and said lower surface.

3. The distractor of claim 1, wherein said upper and lower surfaces each include a plurality of teeth formed therein.

4. The distractor of claim 1, wherein said upper surface includes a proximal portion and a distal portion and said lower surface includes a proximal portion and a distal portion, said proximal portions being generally parallel with one another and said distal portions tapering toward one another from said proximal portions toward said distal end surface.

5. The distractor of claim 1, wherein the distractor includes a proximal end wall adjacent said proximal end and said body extends distally from said proximal end wall.

6. The distractor of claim 5, wherein said proximal end wall includes an inner surface extending above said upper surface and an inner surface extending below said lower surface, said inner surfaces capable of contacting adjacent vertebrae to limit insertion depth of said body in the spinal disc space.

7. The distractor of claim 5, wherein said proximal end wall and said body include a bore extending distally therein from said proximal end wall.

8. The distractor of claim 7, further comprising a shaft attachable to said bore.

9. The distractor of claim 1, wherein said body is made from radiolucent material and said body further includes at least one radiographic marker.

10. The distractor of claim 1, wherein said distal end surface is linear and orthogonal to said central axis.

11. The distractor of claim 1, wherein said lateral surface includes a central linear region extending parallel to the central axis, said second upper and lower transition surfaces extending between said central region and said upper surface and said lower surface, respectively.

12. A spinal disc space distractor, comprising:
    a body positionable in a spinal disc space between adjacent vertebrae, said body having a central axis extending therethrough, said body including:
       a distal end surface;
       a lateral surface extending generally in the direction of said central axis;
       a medial surface opposite said lateral surface and extending generally in the direction of said central axis;
       an upper surface extending generally in the direction of said central axis;
       a lower surface opposite said upper surface and extending generally in the direction of said central axis; and at least a first transition surface extending between said distal end surface and said lateral surface, said first transition surface having a first curvature generally corresponding to a curvature of an inner portion of a cortical rim of vertebral endplates in an axial plane.

13. The distractor of claim 12, wherein said body further includes a second upper transition surface extending between said lateral surface and said upper surface and a second lower transition surface extending between said lateral surface and said lower surface, said second upper and lower transition surfaces each having a second curvature generally corresponding to a curvature of an inner portion of a cortical rim of vertebral endplates in a coronal plane.

14. The distractor of claim 13, wherein said lateral surface includes a central linear region extending parallel to the central axis, said second upper and lower transition surfaces extending between said central region and said upper surface and said lower surface, respectively.

15. The distractor of claim 13, wherein said first curvature is defined by a radius of curvature of 9 millimeters and said second curvature is defined by a radius of curvature of 8 millimeters.

16. The distractor of claim 13, a third upper transition surface extending between said distal end surface and said upper surface and a third lower transition surface extending between said distal end surface and said lower surface, said third upper and lower transition surfaces each having a third curvature generally corresponding to a curvature of an inner portion of a cortical rim of vertebral endplates in a sagittal plane.

17. The distractor of claim 16, wherein said third upper transition surface extends between said first transition surface and said upper surface and said third lower transition surface extends between said first transition surface and said lower surface.

18. The distractor of claim 12, wherein said upper surface includes a proximal portion and a distal portion and said lower surface includes a proximal portion and a distal portion, said proximal portions being generally parallel with one another and said distal portions tapering toward one another from said proximal portions toward said distal end surface.

19. The distractor of claim 12, wherein said first curvature is defined by a radius of curvature of 9 millimeters.

* * * * *